US009216162B2

(12) United States Patent
Goldstein

(10) Patent No.: US 9,216,162 B2
(45) Date of Patent: Dec. 22, 2015

(54) N-ACETYLCYSTEINE AMIDE (NAC AMIDE) IN THE TREATMENT OF DISEASES AND CONDITIONS ASSOCIATED WITH OXIDATIVE STRESS

(71) Applicant: Glenn A. Goldstein, New York, NY (US)

(72) Inventor: Glenn A. Goldstein, New York, NY (US)

(*) Notice: Subject to any disclaimer, the term of this patent is extended or adjusted under 35 U.S.C. 154(b) by 0 days.

(21) Appl. No.: 14/632,089

(22) Filed: Feb. 26, 2015

(65) Prior Publication Data
US 2015/0164830 A1 Jun. 18, 2015

Related U.S. Application Data

(63) Continuation of application No. 13/952,028, filed on Jul. 26, 2013, now Pat. No. 8,993,627, which is a continuation-in-part of application No. 12/707,092, filed on Feb. 17, 2010, now Pat. No. 8,937,099, which is a continuation of application No. 11/912,293, filed as application No. PCT/US2006/015548 on Apr. 21, 2006.

(60) Provisional application No. 60/705,967, filed on Aug. 5, 2005, provisional application No. 60/673,561, filed on Apr. 21, 2005.

(51) Int. Cl.
A01N 37/12 (2006.01)
A01N 37/44 (2006.01)
A61K 31/16 (2006.01)
C07C 323/41 (2006.01)
C07C 323/60 (2006.01)
C07C 233/18 (2006.01)
C07C 233/36 (2006.01)
C07C 233/26 (2006.01)
(Continued)

(52) U.S. Cl.
CPC .................. *A61K 31/16* (2013.01); *A61K 9/007* (2013.01); *A61K 9/0014* (2013.01); *A61K 9/0019* (2013.01); *A61K 9/0043* (2013.01); *A61K 31/167* (2013.01); *A61K 31/375* (2013.01); *C07C 233/18* (2013.01); *C07C 233/26* (2013.01); *C07C 233/36* (2013.01); *C07C 323/41* (2013.01); *C07C 323/60* (2013.01)

(58) Field of Classification Search
CPC ..................................................... A61K 31/16
See application file for complete search history.

(56) References Cited

U.S. PATENT DOCUMENTS 4,520,134 A * 5/1985 Rosen .......................... 514/625
5,691,380 A 11/1997 Mason et al.
(Continued)

FOREIGN PATENT DOCUMENTS

AU 2006238888 11/2006
CA 2606053 11/2008
(Continued)

OTHER PUBLICATIONS

Watt et al. (A pilot study of N-acetylcysteine as adjunctive therapy for severe malaria, QJM (2002) 95(5) 285-290).
(Continued)

*Primary Examiner* — Benjamin Packard
(74) *Attorney, Agent, or Firm* — Lathrop & Gage LLP

(57) ABSTRACT

Methods and compositions comprising N-acetylcysteine amide (NAC amide) and derivatives thereof are used in treatments and therapies for human and non-human mammalian diseases, disorders, conditions and pathologies. Pharmaceutically or physiologically acceptable compositions of NAC amide or derivatives thereof are administered alone, or in combination with other suitable agents, to reduce, prevent, or counteract oxidative stress and free radical oxidant formation and overproduction in cells and tissues, as well as to provide a new source of glutathione.

25 Claims, 6 Drawing Sheets

N-Acetylcysteine (NAC)

N-Acetylcysteine amide (NACA)

(51) Int. Cl.
A61K 9/00 (2006.01)
A61K 31/167 (2006.01)
A61K 31/375 (2006.01)

(56) References Cited

U.S. PATENT DOCUMENTS

| | | | |
|---|---|---|---|
| 5,733,535 | A | 3/1998 | Hollingshead et al. |
| 5,874,468 | A | 2/1999 | Atlas et al. |
| 5,962,421 | A | 10/1999 | Esteras et al. |
| 6,369,106 | B1 | 4/2002 | Atlas et al. |
| 6,420,429 | B1 | 7/2002 | Atlas et al. |
| 6,573,257 | B2 | 6/2003 | Malfroy-Camine et al. |
| 6,623,754 | B2 | 9/2003 | Guo et al. |
| 6,719,969 | B1 | 4/2004 | Hogaboam et al. |
| 2002/0142991 | A1* | 10/2002 | Herzenberg et al. ........... 514/49 |
| 2003/0083266 | A1 | 5/2003 | Atlas et al. |
| 2004/0259732 | A1 | 12/2004 | Asrar et al. |
| 2005/0034196 | A1 | 2/2005 | Klessig et al. |
| 2006/0211628 | A1 | 9/2006 | Atlas et al. |
| 2008/0200548 | A1 | 8/2008 | Goldstein |
| 2008/0274888 | A1 | 11/2008 | Goldstein |
| 2010/0120920 | A1 | 5/2010 | Goldstein |
| 2010/0137441 | A1 | 6/2010 | Goldstein |

FOREIGN PATENT DOCUMENTS

| | | |
|---|---|---|
| EP | 1877044 | 1/2008 |
| WO | 2006116034 | 11/2006 |
| WO | 2006116353 | 11/2006 |
| WO | 2006132712 | 12/2006 |
| WO | 2006132712 A3 | 12/2006 |

OTHER PUBLICATIONS

Extended European Search Report, Application No. EP06751310.1, Date: Jul. 30, 2009.
International Preliminary Report, Applicatio No. PCT/US2006/015015, Date: Oct. 23, 2007.
International Search Report, Application No. PCT/US2006/015015, Date: Aug. 24, 2006.
International Search Report, Application No. PCT/US2006/015021, Date: Oct. 24, 2007.
International Preliminary Report, Application No. PCT/US2006/015548, Date: Oct. 24, 2007.
Examination Report, Application No. NZ563006, Date: Oct. 8, 2008.
Petras et al (Toxicology 121 (1997) pp. 41-49).
Weiss et al. (Protection against ionizing radiation by antioxidant nutrients an dphytochemicals, Toxicity 189 (2003) 1-20).
Bahat-Stroomza Merv et al. (2005), "A novel thoiol antioxidant that crosses the blood brain barrier protects dopaminergic neurons in experimental models of Parkinson's disease," European Journal of Neuroscience, 21 (3):637-646.
Elsayed et al. (2000), "Antioxidant loading reduces oxidative stress induced by high-energy impulse noice (blast) exposure," Toxicology, 155(1-3):91-00. PubMed PMID: 11154801.
Elsayed et al. (2003), "Interplay between high energy impulse noise (blast) and antioxidants in the lung," Toxicology, 189 (1-2):63-74. Review: PubMed PMID:12821283.
Grinberg et al. (2005), "N-acetylcysteine amide, a novel cell-permeating thiol, restores cellular glutathione and protects human red blood cells from oxidative stress," Free Radical Biology & Medicine, 38:136-145.
Kersick et al. (2005), "The Antioxidant Role of Glutathione and N-Acetyl Cysteine Supplements and Exercise-Induced Oxidative Stress," Journal of the International Society of Sports Nutrition, 2(2):38-44.
Offen Daniel et al. (2004), "A low nuilecular weight copper chealtor crosses the blood-brain barrier and attenuates experimental autoimmune encephalomyelitis," Journal of Neurochemistry, 89(5):1241-1251.
Prasad et al. (2004), "Radiation protection in humans: extending the concept of as low as reasonably achievable (ALARA) from dose to biological damage," The British Journal of Radiology, 77:97-99.
Ramasamy et al. (1999), "Modulation of Expression of Endothelial Nitric Oxide Syntahse by Nordihydroguaiaretic Acid, a Phenolic Antioxidant in Cultured Endothelial Cells," Molecular Pharmacology, 56(1):116-123.
Staal et al. (1992), "Glutathione deficiency and human immunodeficiency virus infection," The Lancet, 339:909-912.
Yossi Gilgun-Sherki et al. (2005), "Analysis of Gene Expression in MOG-Induced Experimental Autoimmune Encephalomyelitis After Treatment With a Novel Brain-Penetrating Antioxidant," Journal of Molecular Neuroscience, 27 (1):125-136.
Sohwellenbach, (2010) "Alleged traumatic brain injury research misconduct investigated by Pentagon," www.publicintegrity.org, Jul. 30, 2010.
Toledo et al. (2012), "The young brain and concussion: Imaging as a biomarker for diagnosis and prognosis," Neurosci. Biobehav. Rev., 36(6): 1510-1531.
Ates et al. (2008), "Antioxidant and free radical scavenging properties of N-acetylcysteine amide (NACA) and comparison with N-acetylcysteine (NAC)," Free Radical Res., 42(4): 372 377.

* cited by examiner

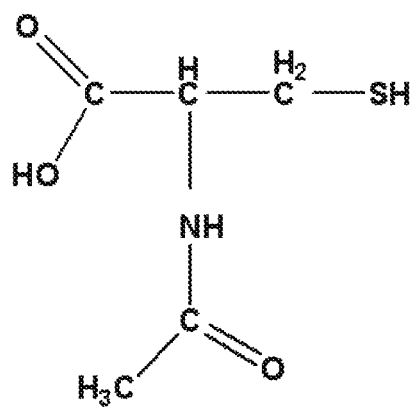
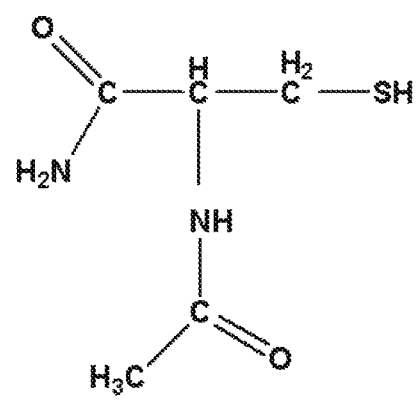
N-Acetylcysteine (NAC)  N-Acetylcysteine amide (NACA)
FIG. 1A  FIG. 1B

FIG. 2A
FIG. 2B
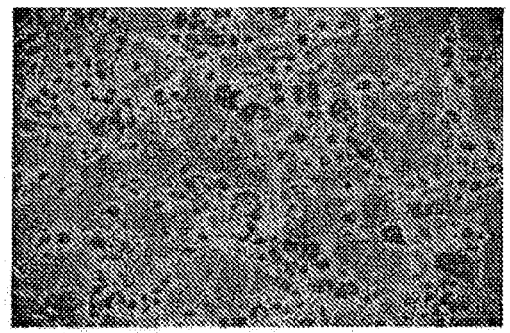
Control
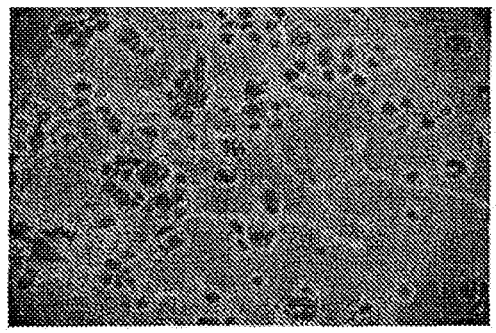
NACA only (750 µM)
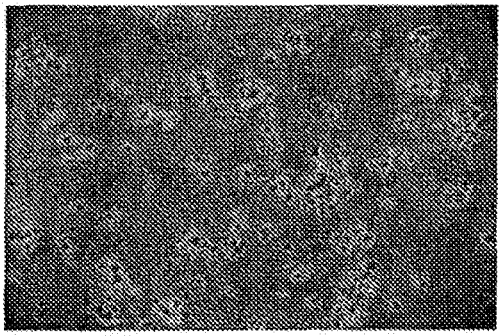
Glutamate only (10 mM)
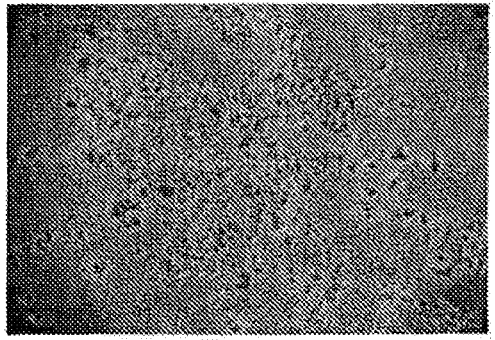
Glutamate (10 mM) + NACA (750 µM)
FIG. 2C
FIG. 2D

N-ACETYLCYSTEINE AMIDE (NAC AMIDE) IN THE TREATMENT OF DISEASES AND CONDITIONS ASSOCIATED WITH OXIDATIVE STRESS

RELATED APPLICATIONS

This application is a continuation of U.S. patent application Ser. No. 13/952,028, filed on Jul. 26, 2013, which is a continuation-in-part of U.S. patent application Ser. No. 12/707,092, filed on Feb. 17, 2010, now U.S. Pat. No. 8,937,099, issued on Jan. 20, 2015, which is a continuation of U.S. patent application Ser. No. 11/912,293, filed on Apr. 25, 2008, which is a national stage entry of International Patent Application No. PCT/US2006/015548, filed on Apr. 21, 2006, which claims priority from U.S. Provisional Patent Application No. 60/673,561, filed on Apr. 21, 2005 and U.S. Provisional Patent Application No. 60/705,967, filed on Aug. 5, 2005, each of which is incorporated by reference herein in its entirety.

FIELD OF THE INVENTION

The present invention generally relates to the treatment of mammalian, including human, diseases with antioxidants. More particularly, the invention relates to treatments and therapies of a variety of diseases and conditions involving the administration of N-acetylcysteine amide (NAC amide) or a derivative thereof, alone or in combination with another agent, to a mammal in need thereof.

BACKGROUND OF THE INVENTION

Oxidative stress plays an important role in the progression of neurodegenerative and age-related diseases, causing damage to proteins, DNA, and lipids. Low molecular weight, hydrophobic antioxidant compounds are useful in treating conditions of peripheral tissues, such as acute respiratory distress syndrome, amyotrophic lateral sclerosis, atherosclerotic cardiovascular disease, multiple organ dysfunctions and central nervous system neurodegenerative disorders, e.g., Parkinson's disease, Alzheimer's disease and Creutzfeldt-Jakob's disease. Oxidative stress has been causally linked to the pathogenesis of Parkinson's disease, Alzheimer's disease and Creutzfeldt-Jakob's disease, as well as other types of disorders. (U.S. Pat. No. 6,420,429 to D. Atlas et al.).

A deficiency of cellular antioxidants may lead to excess free radicals, which cause macromolecular breakdown, lipid peroxidation, buildup of toxins and ultimately cell death. Because of the importance of antioxidant compounds in preventing this cellular oxidation, natural antioxidants, such as glutathione (GSH) (γ-glutamyl cysteinyl glycine) are continuously supplied to the tissues. GSH is synthesized by most cells and is one of the primary cellular antioxidants responsible for maintaining the proper oxidation state within the body. When oxidized, GSH forms a dimer, GSSG, which may be recycled in organs producing glutathione reductase. In human adults, reduced GSH is produced from GSSG, primarily in the liver, and to a smaller extent, by skeletal muscle and red and white blood cells, and is distributed through the blood stream to other tissues in the body.

However, under certain conditions, the normal, physiologic supplies of GSH are insufficient, its distribution is inadequate or local oxidative demands are too high to prevent cellular oxidation. Under other conditions, the production of and demand for cell antioxidants, such as GSH, are mismatched, thus leading to insufficient levels of these molecules in the body. In other cases, certain tissues or biological processes consume the antioxidants so that their intracellular levels are suppressed. In either case, increased serum levels of antioxidant, e.g., glutathione, leads to increased amounts of the antioxidant that can be directed into cells. In facilitated transport systems for cellular uptake, the concentration gradient that drives uptake is increased.

Glutathione N-acetylcysteine amide (NAC amide), the amide form of N-acetylcysteine (NAC), is a low molecular weight thiol antioxidant and a $Cu^{2+}$ chelator. NAC amide provides protective effects against cell damage. NAC amide was shown to inhibit tert.-butylhydroxyperoxide (BuOOH)-induced intracellular oxidation in red blood cells (RBCs) and to retard BuOOH-induced thiol depletion and hemoglobin oxidation in the RBCs. This restoration of thiol-depleted RBCs by externally applied NAC amide was significantly greater than that found using NAC. Unlike NAC, NAC amide protected hemoglobin from oxidation. (L. Grinberg et al., Free Radic Biol Med., 2005 Jan. 1, 38(1):136-45). In a cell-free system, NAC amide was shown to react with oxidized glutathione (GSSG) to generate reduced glutathione (GSH). NAC amide readily permeates cell membranes, replenishes intracellular GSH, and, by incorporating into the cell's redox machinery, protects the cell from oxidation. Because of its neutral carboxyl group, NAC amide possesses enhanced properties of lipophilicity and cell permeability. (See, e.g., U.S. Pat. No. 5,874,468 to D. Atlas et al.). NAC amide is also superior to NAC and GSH in crossing the cell membrane, as well as the blood-brain barrier.

NAC amide may function directly or indirectly in many important biological phenomena, including the synthesis of proteins and DNA, transport, enzyme activity, metabolism, and protection of cells from free-radical mediated damage. NAC amide is a potent cellular antioxidant responsible for maintaining the proper oxidation state within the body. NAC amide can recycle oxidized biomolecules back to their active reduced forms and may be as effective, if not more effective, than GSH as an antioxidant.

Glutamate, an excitatory amino acid, is one of the major neurotransmitters in the central nervous system (CNS). Elevated levels of extracellular glutamate have been shown to be responsible for acute neuronal damage as well as many CNS disorders, including hyperglycemia, ischemia, hypoxia (Choi, D. W., Neuron, 1(8):623-34, 1988), and chronic disorders such as Huntington's, Alzheimer's, and Parkinson's diseases (Meldrum B. and Garthwaite J., Trends Pharmacol Sci., 11(9):379-87, 1990; and Coyle J. T. and Puttfarcken P., Science, 262(5134):689-95, 1993). Two mechanisms have been proposed for glutamate toxicity. The first mechanism explains the excitotoxicity of glutamate as being mediated through three types of excitatory amino acid receptors (Monaghan D. T. et al., Annu Rev Pharmacol Toxicol., 29:365-402, 1989). In addition to receptor-mediated glutamate excitotoxicity, it has also been proposed that elevated levels of extracellular glutamate inhibits cystine uptake, which leads to a marked decrease in cellular GSH levels, resulting in the induction of oxidative stress (Murphy T. H. et al., Neuron, 2(6):1547-58, 1989).

Cysteine is a critical component for intracellular GSH synthesis. Because of redox instability, almost all of the extracellular cysteine is present primarily in its oxidized state, cystine, which is taken up by cells via a cystine/glutamate transporter, the X c-system. Studies indicate that glutamate and cystine share the same transporter; therefore, elevated levels of extracellular glutamate competitively inhibit cystine transport, which leads to depletion of intracellular GSH. (Bannai S. and Kitamura E., J Biol Chem. 255(6):2372-6, 1980; and Bannai S., Biochem Biophys Acta., 779(3):289-306, 1984). Depletion of reduced glutathione results in decreased antioxidant capacity of the cell, accumulation of ROS (reactive oxygen species), and ultimately apoptotic cell death. Several studies have demonstrated the induction of oxidative stress by glutamate in various cell lines including immature cortical neurons (Murphy T. H. et al., FASEB J., 4(6):1624-33, 1990; and Sagara J. et al., J Neurochem., 61(5):1667-71, 1993), oligodendroglia (Oka A. et al., J Neurosci., 13(4):1441-53, 1993), cultured rat astrocytes (Cho Y. and Bannai S., J Neurochem., 55(6):2091-7, 1990), neuroblastoma cells (Murphy T. H. et al., Neuron., 2(6):1547-58, 1989), and PC12 cells (Froissard P. and Duval D., Neurochem Int., 24(5):485-93, 1994).

Certain antioxidants such as NAC, lipoic acid (LA), (Han D. et al., Am J Physiol., 273:1771-8, 1997), tocopherol (Pereira C. M. and Oliveira C. R., Free Radic Biol Med., 23(4):637-47, 1997), and probucol (Naito M. et al., Neurosci Lett., 186(2-3):211-3, 1995) can protect against glutamate cytotoxicity, mostly by replenishing GSH. However, in certain neurological diseases, such as cerebral ischemia and Parkinson's disease, enhancement of tissue GSH in brain regions cannot be attained, because these antioxidant agents have been obstructed by the blood-brain barrier (Panigrahi M. et al., Brain Res., 717(1-2):184-8, 1996; and Gotz M. E. et al., J Neural Transm Suppl., 29:241-9, 1990).

In addition to neurodegenerative diseases, such as those which affect the brain and/or peripheral nervous tissues, other diseases, such as asthma, respiratory-related diseases and conditions, e.g., acute respiratory distress syndrome (ARDS), amyotrophic lateral sclerosis (ALS or Lou Gerhig's disease), atherosclerotic cardiovascular disease and multiple organ dysfunction, are related to the overproduction of oxidants or reactive oxygen species by cells of the immune system.

A number of other disease states have been specifically associated with reductions in the levels of antioxidants such as GSH. Depressed antioxidant levels, either locally in particular organs or systemically, have been associated with a number of clinically defined diseases and disease states, including HIV/AIDS, diabetes and macular degeneration, all of which progress because of excessive free radical reactions and insufficient antioxidants. Other chronic conditions may also be associated with antioxidant deficiency, oxidative stress, and free radical formation, including heart failure and associated conditions and pathologies, coronary arterial restenosis following angioplasty, diabetes mellitus and macular degeneration.

Clinical and pre-clinical studies have demonstrated the linkage between a range of free radical disorders and insufficient antioxidant levels. It has been reported that diabetic complications are the result of hyperglycemic episodes that promote glycation of cellular enzymes and thereby inactivate the synthetic pathways of antioxidant compounds. The result is antioxidant deficiency in diabetics, which may be associated with the prevalence of cataracts, hypertension, occlusive atherosclerosis, and susceptibility to infections in these patients.

High levels of antioxidants, such as GSH, have been demonstrated to be necessary for proper functioning of platelets, vascular endothelial cells, macrophages, cytotoxic T-lymphocytes, and other immune system components. Recently it has been discovered that patients infected with the human immunodeficiency virus, HIV, exhibit low GSH levels in plasma, other body fluids, and in certain cell types, such as macrophages. These low GSH levels do not appear to be due to defects in GSH synthesis. Antioxidant deficiency has been implicated in the impaired survival of patients with HIV. (1997, PNAS USA, Vol. 94, pp. 1967-1972). Raising antioxidant levels in cells is widely recognized as being important in HIV/AIDS and other disorders, because the low cellular antioxidant levels in these disease types permit more and more free radical reactions to fuel and exacerbate the disorders.

HIV is known to start pathologic free radical reactions, which lead to the destruction of antioxidant molecules, as well as their exhaustion and the destruction of cellular organelles and macromolecules. In mammalian cells, oxidative stresses, e.g. low intracellular levels of reduced antioxidants and relatively high levels of free radicals, activate certain cytokines, including NF-κB and TNF-α, which, in turn, activate cellular transcription of the DNA to mRNA, resulting in translation of the mRNA to a polypeptide sequence. In a virus-infected cell, the viral genome is transcribed, resulting in viral RNA production, generally necessary for viral replication of RNA viruses and retroviruses. These processes require a relatively oxidized state of the cell, a condition which results from stress, low antioxidant levels, or the production of reduced cellular products. The mechanism which activates cellular transcription is evolutionarily highly conserved, and therefore it is unlikely that a set of mutations would escape this process, or that an organism in which mutated enzyme and receptor gene products in this pathway would be well adapted for survival. Thus, by maintaining a relatively reduced state of the cell (redox potential), viral transcription, a necessary step in late stage viral replication, is impeded.

The amplification effect of oxidative intracellular conditions on viral replication is compounded by the actions of various viruses and viral products, which degrade antioxidants, such as GSH. For example, gp120, an HIV surface glycoprotein having a large number of disulfide bonds, is normally present on the surface of infected cells. gp120 oxidizes GSH, resulting in reduced intracellular GSH levels. On the other hand, GSH reduces the disulfide bonds of gp120, thus reducing or eliminating its biological activity that is necessary for viral infectivity. Antioxidants such as GSH therefore interfere with the production of such oxidized proteins and degrade them once formed. In a cell that is actively replicating viral gene products, a cascade of events may occur which can allow the cell to pass from a relatively quiescent stage with low viral activity to an active stage with massive viral replication and cell death. This is accompanied by a change in redox potential. By maintaining adequate levels of antioxidant, this cascade may be impeded.

HIV is transmitted through two predominant routes, namely, contaminated blood and/or sexual intercourse. In pediatric cases, approximately one half of the newborn individuals are infected in utero and one half are infected at delivery. This circumstance permits a study of prevention of transmission since the time of spread is known. Initially, there is an intense viral infection simulating a severe case of the flu, with massive replication of the virus. Within weeks, this acute phase passes spontaneously as the body mounts a largely successful immune defense. Thereafter, the individual has no outward manifestations of the infection. However, the virus continues to replicate within immune system cells and tissues, e.g., lymph nodes, lymphoid nodules, macrophages and certain multidendritic cells that are found in various body cavities.

Such stealthy and widespread infection is not just a viral problem. The virus, in addition to replicating, causes excessive production of various free radicals and various cytokines in toxic or elevated levels. The cytokines are normally occurring biochemical substances that signal numerous reactions and that typically exist in minuscule concentrations. Eventually, after an average of 7-10 years of seemingly quiescent HIV infection, the corrosive free radicals and the toxic levels of cytokines begin to cause outward symptoms in infected individuals and failures in the immune system begin. Substances like 15-HPETE are immunosuppressive and TNF-α causes muscle wasting, among other toxic factors. The numbers of viral particles increase and the patient develops the Acquired Immune Deficiency Syndrome, AIDS, which may last 2 to 4 years before the individual's demise. AIDS, therefore, is not merely a virus infection, although the viral infection is believed to be an integral part of the etiology of the disease.

Further, HIV has a powerful ability to mutate. It is this capability that makes it difficult to create a vaccine or to develop long-term, antiviral pharmaceutical treatments. As more people fail to be successfully treated by the present complex regimens, the number of resistant viral strains is increasing. Resistant strains of HIV are a particularly dangerous population of the virus and pose a considerable health threat. These resistant HIV mutants also add to the difficulties in developing vaccines that will be able to inhibit the activity of highly virulent viral types. Further, the continuing production of free radicals and cytokines that may become largely independent of the virus perpetuate the dysfunctions of the immune system, the gastrointestinal tract, the nervous system, and many other organs in patients with AIDS. The published scientific literature indicates that many of these diverse organ system dysfunctions are due to systemic deficiencies of antioxidant compounds that are engendered by the virus and its free radicals. For example, GSH is consumed in HIV infections because it is the principal, bulwark antioxidant versus free radicals. An additional cause of erosion of GSH levels is the presence of numerous disulfide bonds in HIV proteins, such as the gp120 cell surface protein. Disulfide bonds react with GSH and oxidize it. Thus, there is a need for other antioxidants to be used to replace antioxidants such as GSH whose normal function is adversely affected by HIV infection.

The current HIV/AIDS pharmaceuticals take good advantage of the concept of pharmaceutical synergism, wherein two different targets in one process are affected simultaneously. The effect is more than additive. The drugs now in use were selected to inhibit two very different points in the long path of viral replication. The pathway of viral replication as understood by skilled practitioners in the art is described in U.S. Pat. No. 6,420,429. New anti-HIV/AIDS therapies include additional drugs in the classes of Reverse Transcriptase inhibitors and protease inhibitors. Also, drugs are in development to block the integrase enzyme of the virus, which integrates the HIV DNA into the infected cell's DNA, analogous to splicing a small length of wire into a longer wire. Vaccine development also continues, although prospects seem poor because HIV appears to be a moving target and seems to change rapidly. Vaccine development is also impaired by the immune cell affinity of the virus.

Individuals infected with HIV have lowered levels of serum acid-soluble thiols and antioxidants such as GSH in plasma, peripheral blood monocytes and lung epithelial lining fluid. In addition, it has been shown that $CD4^+$ and $CD8^+$ T cells with high intracellular GSH levels are selectively lost as HIV infection progresses. This deficiency may potentiate HIV replication and accelerate disease progression, especially in individuals with increased concentrations of inflammatory cytokines, because such cytokines stimulate HIV replication more efficiently in cells in which antioxidant compounds are depleted. In addition, the depletion of antioxidants, such as GSH, is also associated with a process known as apoptosis, or programmed cell death. Thus, intercellular processes which artificially deplete GSH may lead to cell death, even if the process itself is not lethal.

Diabetes mellitus ("diabetes") is found in two forms: childhood or autoimmune (Type I, IDDM) and late-onset or non-insulin dependent (Type II, NIDDM). Type I constitutes about 30% of the cases of diabetes. The rest of the cases are represented by Type II. In general, the onset of diabetes is sudden for Type I and insidious or chronic for Type II. Symptoms include excessive urination, hunger and thirst, with a slow and steady loss of weight associated with Type I. Obesity is often associated with Type II and has been thought to be a causal factor in susceptible individuals. Blood sugar is often high and there is frequent spilling of sugar in the urine. If the condition goes untreated, the victim may develop ketoacidosis with a foul-smelling breath similar to some who has been drinking alcohol. The immediate medical complications of untreated diabetes can include nervous system symptoms, and even diabetic coma.

Because of the continuous and pernicious occurrence of hyperglucosemia (very high blood sugar levels), a non-enzymatic chemical reaction, called glycation, frequently occurs inside cells and causes a chronic inactivation of essential enzymes. One of the most critical enzymes, γ-glutamyl-cysteine synthetase, is glycated and readily inactivated. This enzyme is involved in a critical step in the biosynthesis of glutathione in the liver. The net result of this particular glycation is a deficiency in the production of GSH in diabetics.

GSH is in high demand throughout the body for multiple, essential functions, for example, within all mitochondria, to produce chemical energy called ATP. With a deficiency or absence of GSH, brain cells, heart cells, nerve cells, blood cells and many other cell types are not able to function properly and can be destroyed through apoptosis associated with oxidative stress and free radical formation. GSH is the major antioxidant in the human body and the only one that can be synthesized de novo. It is also the most common small molecular weight thiol in both plants and animals. Without GSH the immune system cannot function, and the central and peripheral nervous systems become aberrant and then cease to function. Because of the dependence on GSH as the carrier of nitric oxide, a vasodilator responsible for control of vascular tone, the cardiovascular system does not function well and eventually fails. Since all epithelial cells seem to require GSH, without GSH, intestinal lining cells also do not function properly and valuable micronutrients are lost, nutrition is compromised, and microbes are given portals of entry to cause infections.

In diabetes, the use of GSH precursors cannot help to control GSH deficiency due to the destruction of the rate-limiting enzyme by glycation. As GSH deficiency becomes more profound, the well-known sequelae of diabetes progress in severity. The complications that develop in diabetics are essentially due to runaway free radical damage since the available GSH supplies in diabetics are insufficient. For example, a diabetic individual becomes more susceptible to infections because the immune system approaches collapse when GSH levels fall, analogous to the situation in HIV/AIDS. In addition, peripheral vasculature becomes comprised and blood supply to the extremities is severely diminished because GSH is not available in sufficient amounts to stabilize nitric oxide to effectively exert its vascular dilation (relaxation) property. Gangrene is a common sequel and successive amputations often result in later years. Peripheral neuropathies, the loss of sensation commonly of the feet and lower extremities develop and are often followed by aberrant sensations like uncontrollable burning or itching. Retinopathy and nephropathy are later events that are actually due to microangiopathy, i.e., excessive budding and growth of new blood vessels and capillaries, which often will bleed due to weakness of the new vessel walls. This bleeding causes damage to the retina and kidneys with resulting blindness and renal shutdown, which requires dialysis treatment. Further, cataracts occur with increasing frequency as the GSH deficiency deepens. Large and medium sized arteries become sites of accelerated severe atherosclerosis, with myocardial infarcts at early ages, and of a more severe degree. If coronary angioplasty is used to treat the severe atherosclerosis, diabetics are much more likely to have re-narrowing of cardiac vessels, termed restenosis.

Macular degeneration as a cause of blindness is a looming problem as the population ages. Age-related macular degeneration (ARMD) is characterized by either a slow (dry form) or rapid (wet form) onset of destruction and irrevocable loss of rods and cones in the macula of the eye. The macula is the approximate center of the retina wherein the lens of the eye focuses its most intense light. The visual cells, known as the rods and cones, are an outgrowth and active part of the central nervous system. They are responsible and essential for the fine visual discrimination required to see clear details such as faces and facial expression, reading, driving, operation of machinery and electrical equipment and general recognition of surroundings. Ultimately, the destruction of the rods and cones leads to functional, legal blindness. Since there is no overt pain associated with the condition, the first warnings of onset are usually noticeable loss of visual acuity. This may already signal late stage events. It is now thought that one of the very first events in this pathologic process is the formation of a material called "drusen", which first appears as either patches or diffuse drops of yellow material deposited upon the surface of the retina in the macula lutea or yellow spot. This is the area of the retina where sunlight is focused by the lens and which contains the highest density of rods for acuity. Although cones, which detect color, are lost as well in this disease, it is believed to be loss of rods, which causes the blindness. Drusen has been chemically analyzed and found to be composed of a mixture of lipids that are peroxidized by free radical reactions.

It is believed that the loss of retinal pigmented epithelial (RPE) cells occurs first in ARMD. Once an area of the retinal macula is devoid of RPE cells, loss of rods, and eventually some cones, occurs. Finally, budding of capillaries begins and typical microangiopathy associated with late stage ARMD occurs. It is also known that RPE cells require large quantities of GSH for their proper functioning. When GSH levels drop severely in cultures of RPE cells, the RPE cells begin to die. When cultures of these cells are supplemented with GSH in the medium, they thrive. There is increasing evidence that progression of the disease is paced by a more profound deficiency in GSH within the retina and probably within these cells, as indicated by cell culture studies.

It is generally believed that "near" ultraviolet (UVB) and visual light of high intensity primarily from sunlight is a strong contributing factor of ARMD. People with light-colored irises constitute a high risk population for macular degeneration, as do those with jobs that keep them outdoors and those in equatorial areas where sunlight is most intense. Additional free radical insults, e.g., smoking, adds to the risk of developing ARMD. Several approaches have been unsuccessfully tested to combat ARMD, including chemotherapy. Currently, there is no effective therapy to treat ARMD. Laser therapy has been developed which has been used widely to slow the damage produced in the slow onset form of the disease by cauterizing neovascular growth. However the eventual outcome of the disease, once it has started to progress, is certain.

The importance of thiols and especially of GSH to lymphocyte function has been known for many years. Adequate concentrations of GSH are required for mixed lymphocyte reactions, T-cell proliferation, T- and B-cell differentiation, cytotoxic T-cell activity, and natural killer cell activity. Adequate GSH levels have been shown to be necessary for microtubule polymerization in neutrophils. Intraperitoneally administered GSH augments the activation of cytotoxic T-lymphocytes in mice, and dietary GSH was found to improve the splenic status of GSH in aging mice, and to enhance T-cell mediated immune responses. The presence of macrophages can cause a substantial increase of the intracellular GSH levels of activated lymphocytes in their vicinity. Macrophages consume cystine via a strong membrane transport system, and generate large amounts of cysteine, which they release into the extracellular space. It has been demonstrated that macrophage GSH levels (and therefore cysteine equivalents) can be augmented by exogenous GSH. T-cells cannot produce their own cysteine, and it is required by T-cells as the rate-limiting precursor of GSH synthesis. The intracellular GSH level and the DNA synthesis activity in mitogenically-stimulated lymphocytes are strongly increased by exogenous cysteine, but not cystine. In T-cells, the membrane transport activity for cystine is ten-fold lower than that for cysteine. As a consequence, T-cells have a low baseline supply of cysteine, even under healthy physiological conditions. The cysteine supply function of the macrophages is an important part of the mechanism which enables T-cells to shift from a GSH-poor to a GSH-rich state.

The importance of the intracellular GSH concentration for the activation of T-cells is well established. It has been reported that GSH levels in T-cells rise after treatment with GSH; it is unclear whether this increase is due to uptake of the intact GSH or via extracellular breakdown, transport of breakdown products, and subsequent intracellular GSH synthesis. Decreasing GSH by 10-40% can completely inhibit T-cell activation in vitro. Depletion of intracellular GSH has been shown to inhibit the mitogenically-induced nuclear size transformation in the early phase of the response. Cysteine and GSH depletion also affects the function of activated T-cells, such as cycling T-cell clones and activated cytotoxic T-lymphocyte precursor cells in the late phase of the allogeneic mixed lymphocyte culture. DNA synthesis and protein synthesis in IL-2 dependent T-cell clones, as well as the continued growth of preactivated CTL precursor cells and/or their functional differentiation into cytotoxic effector cells are strongly sensitive to GSH depletion.

Glutathione status is a major determinant of protection against oxidative injury. GSH acts on the one hand by reducing hydrogen peroxide and organic hydroperoxides in reactions catalyzed by glutathione peroxidases, and on the other hand by conjugating with electrophilic xenobiotic intermediates capable of inducing oxidant stress. The epithelial cells of the renal tubule have a high concentration of GSH, no doubt because the kidneys function in toxin and waste elimination, and the epithelium of the renal tubule is exposed to a variety of toxic compounds. GSH, transported into cells from the extracellular medium, substantially protects isolated cells from intestine and lung against t-butylhydroperoxide, menadione or paraquat-induced toxicity. Isolated kidney cells also transport GSH, which can supplement endogenous synthesis of GSH to protect against oxidant injury. Hepatic GSH content has also been reported to increase (i.e. to double) in the presence of exogenous GSH. This may be due either to direct transport, as has been reported for intestinal and alveolar cells, or via extracellular degradation, transport, and intracellular resynthesis.

The nucleophilic sulfur atom of the cysteine moiety of GSH serves as a mechanism to protect cells from harmful effects induced by toxic electrophiles. It is well established that glutathione S-conjugate biosynthesis is an important mechanism of drug and chemical detoxification. GSH conjugation of a substrate generally requires both GSH and glutathione-S-transferase activity. The existence of multiple glutathione-S-transferases with specific, but also overlapping, substrate specificities enables the enzyme system to handle a wide range of compounds. Several classes of compounds are believed to be converted by glutathione conjugate formation to toxic metabolites. For example, halogenated alkenes, hydroquinones, and quinones have been shown to form toxic metabolites via the formation of S-conjugates with GSH. The kidney is the main target organ for compounds metabolized by this pathway. Selective toxicity to the kidney is the result of the kidney's ability to accumulate intermediates formed by the processing of S-conjugates in the proximal tubular cells, and to bioactivate these intermediates to toxic metabolites.

The administration of morphine and related compounds to rats and mice results in a loss of up to approximately 50% of hepatic GSH. Morphine is known to be biotransformed into morphinone, a highly hepatotoxic compound, which is 9 times more toxic than morphine in mouse by subcutaneous injection, by morphine 6-dehydrogenase activity. Morphinone possesses an $\alpha,\beta$-unsaturated ketone, which allows it to form a glutathione S-conjugate. The formation of this conjugate correlates with loss of cellular GSH. This pathway represents the main detoxification process for morphine. Pretreatment with GSH protects against morphine-induced lethality in the mouse.

The deleterious effects of methylmercury on mouse neuroblastoma cells are largely prevented by co-administration of GSH. GSH may complex with methylmercury, prevent its transport into the cell, and increase cellular antioxidant capabilities to prevent cell damage. Methylmercury is believed to exert its deleterious effects on cellular microtubules via oxidation of tubulin sulfhydryls, and by alterations due to peroxidative injury. GSH also protects against poisoning by other heavy metals such as nickel and cadmium.

Because of its known role in renal detoxification and its low toxicity, GSH has been explored as an adjunct therapy for patients undergoing cancer chemotherapy with nephrotoxic agents such as cisplatin, in order to reduce systemic toxicity. In one study, GSH was administered intravenously to patients with advanced neoplastic disease, in two divided doses of 2,500 mg, shortly before and after doses of cyclophosphamide. GSH was well tolerated and did not produce unexpected toxicity. The lack of bladder damage, including microscopic hematuria, supports the protective role of this compound. Other studies have shown that co-administration of GSH intravenously with cisplatin and/or cyclophosphamide combination therapy, reduces associated nephrotoxicity, while not unduly interfering with the desired cytotoxic effect of these drugs.

GSH has an extremely low toxicity, and oral $LD_{50}$ measurements are difficult to perform due to the sheer mass of GSH, which has to be ingested by the animal in order to see any toxic effects. GSH can be toxic, especially in cases of ascorbate deficiency, and these effects may be demonstrated in, for example, ascorbate deficient guinea pigs given 3.75 mmol/kg daily (1,152 mg/kg daily) in three divided doses, whereas in non-ascorbate deficient animals, toxicity was not seen at this dose, but were seen at double this dose.

There is a need in the art for other compounds and therapeutic aspects to treat a number of diseases that are linked to oxidative stress and the presence of free oxygen radicals and associated disease pathogenesis in cells and tissues. Needed are antioxidant compounds, other than GSH, that are safe and even more potent, to overcome high oxidative stress in the pathogenesis of diseases. Ideally, such compounds should readily cross the blood-brain barrier and easily permeate the cell membrane. Antioxidants such as vitamins E and C are not completely effective at decreasing oxidative stress, particularly because, in the case of vitamin E, they do not effectively cross through the cell membrane to reach the cytoplasm so as to provide antioxidant effects.

SUMMARY OF THE INVENTION

The present invention provides the use of a potent antioxidant N-acetylcysteine amide (NAC amide) or derivatives thereof, or a physiologically acceptable derivative, salt, or ester thereof, in new applications to treat disorders, conditions, pathologies and diseases that result from, or are associated with, the adverse effects of oxidative stress and/or the production of free radicals in cells, tissues and organs of the body. NAC amide and its derivatives are provided for use in methods and compositions for improving and treating such disorders, conditions, pathologies and diseases.

As used herein, a "subject" within the context of the present invention encompasses, without limitation, mammals, e.g., humans, domestic animals and livestock including cats, dogs, cattle and horses. A "subject in need thereof" is a subject having one or more manifestations of disorders, conditions, pathologies, and diseases as disclosed herein in which administration or introduction of NAC amide or its derivatives would be considered beneficial by those of ordinary skill in the art.

In an aspect of the present invention, methods and compositions comprising NAC amide provide an antioxidant to cells and tissues to reduce oxidative stress, and the adverse effects of cellular oxidation, in an organism. The invention provides a method of reducing oxidative stress associated with the conditions, diseases, pathologies as described herein, by administering a pharmaceutically acceptable formulation of NAC amide or derivatives thereof to a human or non-human mammal in an amount effective to reduce oxidative stress.

In another aspect of the present invention, NAC amide and its derivatives are provided to treat an organism having a disorder, condition, pathology, or disease that is associated with the overproduction of oxidants and/or oxygen free radical species. According to this invention NAC amide treatment can be prophylactic or therapeutic.

"Therapeutic treatment" or "therapeutic effect" means any improvement in the condition of a subject treated by the methods of the present invention, including obtaining a preventative or prophylactic effect, or any alleviation of the severity of signs or symptoms of a disorder, condition, pathology, or disease or its sequelae, including those caused by other treatment methods (e.g., chemotherapy and radiation therapy), which can be detected by means of physical examination, laboratory, or instrumental methods and considered statistically and/or clinically significant by those skilled in the art.

"Prophylactic treatment" or "prophylactic effect" means prevention of any worsening in the condition of a subject treated by the methods of the present invention, as well as prevention of any exacerbation of the severity of signs and symptoms of a disorder, condition, pathology, or disease or its sequelae, including those caused by other treatment methods (e.g., chemotherapy and radiation therapy), which can be detected by means of physical examination, laboratory, or instrumental methods and considered statistically and/or clinically significant by those skilled in the art.

In another aspect of the present invention, NAC amide is used in the treatment and/or prevention of cosmetic conditions and dermatological disorders of the skin, hair, nails, and mucosal surfaces when applied topically. In accordance with the invention, compositions for topical administration are provided that include (a) NAC amide, or derivatives thereof, or a suitable salt or ester thereof, or a physiologically acceptable composition containing NAC amide or its derivatives; and (b) a topically acceptable vehicle or carrier. The present invention also provides a method for the treatment and/or prevention of cosmetic conditions and/or dermatological disorders that entails topical administration of NAC amide- or NAC-amide derivative-containing compositions to an affected area of a patient.

In yet another of its aspects the present invention provides methods and compositions useful for cancer and pre-cancer therapy utilizing NAC amide or a derivative thereof, or its pharmaceutically acceptable salts or esters. The present invention particularly relates to methods and compositions comprising NAC amide or a derivative thereof in which apoptosis is selectively induced in cells of cancers or precancers.

In another aspect, the present invention provides compositions and methods comprising NAC amide or a derivative thereof for the suppression of allograft rejection in recipients of allografts.

In another aspect, the present invention provides a NAC amide or a derivative thereof in a method of supporting or nurturing the growth of stem cells for stem cell transplants, particularly stem cells cultured in vitro prior to introduction into a recipient animal, including humans.

In another aspect, the present invention provides methods of inhibiting, preventing, treating, or both preventing and treating, central nervous system (CNS) injury or disease, traumatic brain injury, neurotoxicity or memory deficit in a subject, involving the administration of a therapeutically effective amount of NAC amide, or derivative thereof or a pharmaceutically acceptable composition thereof.

In another of its aspects, the present invention provides a method of killing or inhibiting the growth of microorganisms by providing NAC amide in an amount effective to increase cellular levels of HIF-1 or HIF-1α to enhance the capacity of white blood cells to kill or inhibit the growth of the microorganisms. Also in accordance with the invention, NAC amide is used as a countermeasure for biodefensive purposes, e.g., in killing or growth inhibiting microorganisms, viruses, *mycoplasma*, etc., and in treating resulting diseases and conditions, as further described herein.

In another aspect, the present invention provides a method of preventing tissue destruction resulting from the effects of metalloproteinases, such as MMP-3, which has been found to cause normal cells to express the Rac1b protein, an unusual form of Rho GTPase that has previously been found only in cancers. Rac1b stimulates the production of highly reactive oxygen species (ROS), which can promote cancer by activating major genes that elicits massive tissue disorganization. In accordance with the present invention NAC amide is used to block the effects of Rac1b-induced ROS production by administering or introducing NAC amide to cells, tissues, and/or the body of a subject in need thereof, to target molecules in the pathways leading to tissue damage and degradation. Thus, NAC amide can be used to inhibit MMP-3 and its adverse functions, to target ROS indirectly or directly via the processes by which ROS activates genes to induce the EMT.

Another aspect of the present invention provides a method of stimulating endogenous production of cytokines and hematopoietic factors, comprising administering or introducing NAC amide to cells, tissues, and/or a subject in need thereof for a period of time to stimulate the endogenous production. NAC amide can be used to stimulate production of cytokines and hematopoietic factors, such as but not limited to, TNF-α, IFN-α, IFN-β, IFN-γ, IL-1, IL-2, IL-6, IL-10, erythropoietin, G-CSF, M-CSF, and GM-CSF, which are factors that modulate the immune system and whose biological activities are involved in various human diseases, such as neoplastic and infectious diseases, as well as those involving hematopoiesis and immune depressions of various origin (such as, without limitation, erythroid, myeloid, or lymphoid suppression). Stimulation of endogenous production of these cytokines and hematopoietic factors by NAC amide is particularly advantageous, since exogenous administration of these cytokines and hematopoietic factors have limitations associated with the lack of acceptable formulations, their exorbitant cost, short half-life in biological media, difficulties in dose-determination, and numerous toxic and allergic effects.

In another embodiment, the present invention encompasses methods and composition comprising NAC amide for detecting NAC-amide responsive changes in gene expression in a cell, tissue, and/or a subject, comprising administering or introducing NAC amide or derivative of NAC amide to the cell, tissue, and/or subject for a period of time to induce changes in gene expression and detecting the changes in gene expression. NAC amide and derivatives thereof can induce changes in gene expression such as genes involved in apoptosis, angiogenesis, chemotaxis, among others.

In another aspect, the present invention provides directed delivery of NAC amide to cells, such as cancer cells that express high levels of receptors for folic acid (folate) or glutathione. According to this aspect, NAC amide ("NACA") is coupled to a ligand for the receptor (e.g., folic acid or glutathione) to form a conjugate, and then this NACA-ligand conjugate is coated or adsorbed onto readily injectable nanoparticles using procedures known to those skilled in the art. According to this aspect, the nanoparticles containing NAC amide ("nano-NACA particles") may be preferentially taken up by cancer or tumor cells where the NAC amide will exert its desired effects. Accordingly, the present invention provides a method of directed delivery of NAC amide to host cells expressing high levels of surface receptor for a ligand, in which the method involves (a) coupling NAC amide to the surface receptor ligand to form a NAC amide-ligand conjugate; (b) adsorbing the NAC amide-ligand conjugate onto nanoparticles; and (c) introducing the nanoparticles of (b) into the host. The invention further provides a method of directed delivery of NAC amide to host cells expressing high levels of surface receptor for a ligand, in which the method involves (a) conjugating acetylated dendritic nanopolymers to a ligand; (b) coupling the conjugated ligand of (a) to NAC amide to form NAC amide-ligand nanoparticles; and c) introducing the nanoparticles of (b) into the host.

Another aspect of the present invention provides a compound of the formula I:

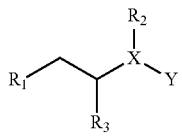

wherein: $R_1$ is OH, SH, or S—S—Z; X is C or N; Y is $NH_2$, OH, $CH_3$—C=O, or NH—$CH_3$; $R_2$ is absent, H, or =O $R_3$ is absent or

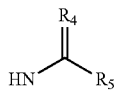

wherein: $R_4$ is NH or O; $R_5$ is $CF_3$, $NH_2$, or $CH_3$ and wherein: Z is

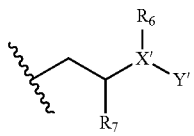

with the proviso that if $R_1$ is S—S—Z, X and X' are the same, Y and Y' are the same, $R_2$ and $R_6$ are the same, and $R_3$ and $R_7$ are the same.

The present invention also provides a NAC amide compound and NAC amide derivatives comprising the compounds disclosed herein.

In another aspect, a process for preparing an L- or D-isomer of the compounds of the present invention are provided, comprising adding a base to L- or D-cystine diamide dihydrochloride to produce a first mixture, and subsequently heating the first mixture under vacuum; adding a methanolic solution to the heated first mixture; acidifying the mixture with alcoholic hydrogen chloride to obtain a first residue; dissolving the first residue in a first solution comprising methanol saturated with ammonia; adding a second solution to the dissolved first residue to produce a second mixture; precipitating and washing the second mixture; filtering and drying the second mixture to obtain a second residue; mixing the second residue with liquid ammonia and an ethanolic solution of ammonium chloride to produce a third mixture; and filtering and drying the third mixture, thereby preparing the L- or D-isomer compound.

In some embodiments, the process further comprises dissolving the L- or D-isomer compound in ether; adding to the dissolved L- or D-isomer compound an ethereal solution of lithium aluminum hydride, ethyl acetate, and water to produce a fourth mixture; and filtering and drying the fourth mixture, thereby preparing the L- or D-isomer compound.

Another aspect of the invention provides a process for preparing an L- or D-isomer of the compounds disclosed herein, comprising mixing S-benzyl-L- or D-cysteine methyl ester hydrochloride or O-benzyl-L- or D-serine methyl ester hydrochloride with a base to produce a first mixture; adding ether to the first mixture; filtering and concentrating the first mixture; repeating steps (c) and (d), to obtain a first residue; adding ethyl acetate and a first solution to the first residue to produce a second mixture; filtering and drying the second mixture to produce a second residue; mixing the second residue with liquid ammonia, sodium metal, and an ethanolic solution of ammonium chloride to produce a third mixture; and filtering and drying the third mixture, thereby preparing the L- or D-isomer compound.

Yet another aspect of the invention provides a process for preparing a compound as disclosed herein, comprising mixing cystamine dihydrochloride with ammonia, water, sodium acetate, and acetic anhydride to produce a first mixture; allowing the first mixture to precipitate; filtering and drying the first mixture to produce a first residue; mixing the second residue with liquid ammonia, sodium metal, and an ethanolic solution of ammonium chloride to produce a second mixture; filtering and drying the second mixture, thereby preparing the compound.

The present invention also provides a food additive comprising NAC amide or a NAC amide derivative as disclosed herein.

Additional aspects, features and advantages afforded by the present invention will be apparent from the detailed description and exemplification hereinbelow.

BRIEF DESCRIPTION OF THE FIGURES

FIG. 1A presents the structure of N acetyl cysteine. FIG. 1B presents the structure of N-acetylcysteine amide (NAC amide).

FIGS. 2A-2D show the cytotoxic response of PC12 cells to glutamate and protection by NAC amide. PC12 cells were plated at a density $25 \times 10^3$ cells/well in a 24 well plate and grown for 24 h in culture medium. They were treated or not (control) with 10 mM Glu with or without NAC amide, as described in Example 1. Twenty-four hours later, cells were examined and photographed. FIG. 2A: Control; FIG. 2B: NAC amide (NACA) only; FIG. 2C: Glutamate only; FIG. 2D: Glutamate and NACA.

DETAILED DESCRIPTION OF THE INVENTION

Figure 3:
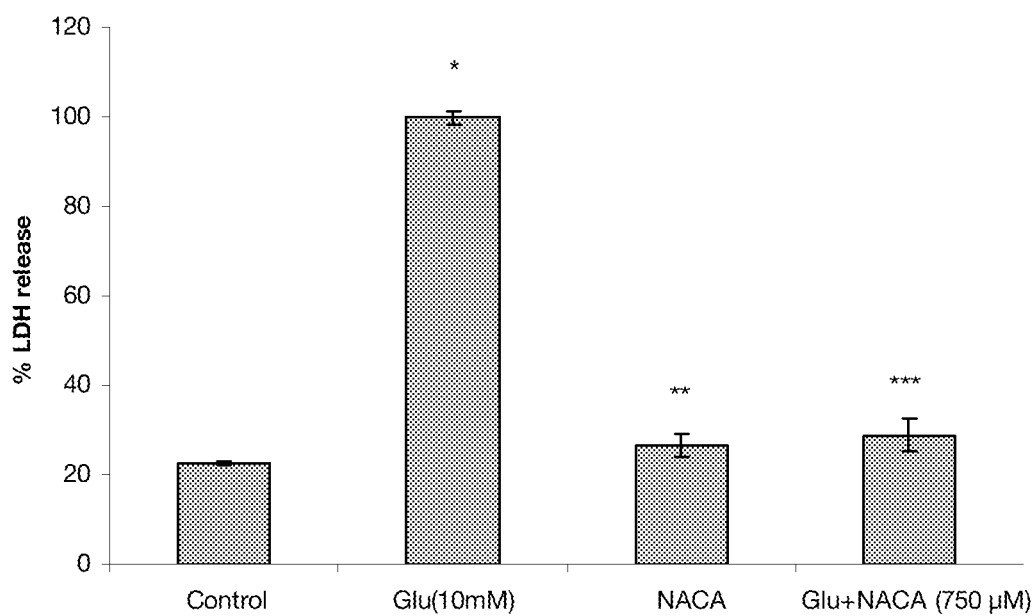
FIG. 3 shows the protective effect of NAC amide against glutamate cytotoxicity. Cells were plated and grown for 24 hours in a culture medium; then they were treated or not (control) with 10 mM Glu, with or without NAC amide. Twenty-four hours later, the % LDH release was determined using LDH analysis. Values represent means±SD. Statistically different values of *P<0.0001 and P<0.05 were determined, compared to control. *P<0.0001 compared to glutamate-treated group.

The present invention involves the use of an effective and potent antioxidant, glutathione N-acetylcysteine amide (NAC amide), (FIG. 1), or a physiologically or pharmaceutically acceptable derivative or salt or ester thereof, for use in a variety of disorders, conditions, pathologies and diseases in which oxidative stress and/or free radical formation cause damage, frequently systemic damage, to cells, tissues and organs of the body. The invention encompasses a pharmaceutically acceptable composition comprising NAC amide, e.g., water-soluble NAC amide, or physiologically acceptable derivatives, salts, or esters thereof, which can be used in treatment and therapeutic methods in accordance with this invention.

Glutathione N-acetylcysteine amide (NAC amide), the amide form of N-acetylcysteine (NAC), is a novel low molecular weight thiol antioxidant and a $Cu^{2+}$ chelator. NAC amide provides protective effects against cell damage in its role as a scavenger of free radicals. In mammalian red blood cells (RBCs), NAC amide has been shown to inhibit tert.-butylhydroxyperoxide (BuOOH)-induced intracellular oxidation and to retard BuOOH-induced thiol depletion and hemoglobin oxidation in the RBCs. This restoration of thiol-depleted RBCs by externally applied NAC amide was significantly greater than that found using NAC. Unlike NAC, NAC amide protected hemoglobin from oxidation. (L. Grinberg et al., Free Radic Biol Med., 2005 Jan. 1, 38(1):136-45). In a cell-free system, NAC amide was shown to react with oxidized glutathione (GSSG) to generate reduced glutathione (GSH). NAC amide readily permeates cell membranes, replenishes intracellular GSH, and, by incorporating into the cell's redox machinery, protects the cell from oxidation. Because of its neutral carboxyl group, NAC amide possesses enhanced properties of lipophilicity and cell permeability. (See, e.g., U.S. Pat. No. 5,874,468 to D. Atlas et al.). NAC amide is also superior to NAC and GSH in crossing the cell membrane, as well as the blood-brain barrier. NAC amide can be prepared as described in U.S. Pat. No. 6,420,429 to D. Atlas et al., the contents of which are incorporated by reference herein.

NAC amide may function directly or indirectly in many important biological phenomena, including the synthesis of proteins and DNA, transport, enzyme activity, metabolism, and protection of cells from free-radical mediated damage. NAC amide is a potent cellular antioxidant responsible for maintaining the proper oxidation state within cells. NAC amide is synthesized by most cells and can recycle oxidized biomolecules back to their active reduced forms. As an antioxidant, NAC amide may be as effective, if not more effective, than GSH.

In one embodiment, the present invention encompasses methods and compositions comprising NAC amide for preventing, reducing, protecting, or alleviating glutamate-induced cytotoxicity in neurodegenerative diseases, particularly in neuronal cells and tissues (See, e.g., Example 1). In this embodiment, NAC amide can protect cells of the nervous system from the effects of oxidative toxicity induced by glutamate. Without wishing to be bound by theory, NAC amide treatment can function to supply GSH as a substrate for GSH peroxidase activity in affected cells. In accordance with the present invention, NAC amide can inhibit lipid peroxidation, scavenge for reactive oxygen species (ROS) and enhance intracellular levels of GSH to combat and overcome oxidative stress. In addition, NAC amide can chelate lead and protect against lead-induced oxidative stress. NAC amide is particularly beneficial and advantageous for neurological disorders and diseases affecting the brain and associated parts thereof, because it more readily crosses the blood-brain barrier to enter the brain and provide its antioxidant effects.

Different neurodegenerative conditions and diseases that can be treated according to this embodiment include cerebral ischemia, Parkinson's disease. NAC amide can be used in the reduction of brain damage during seizures; to provide resistance to induced epileptic seizures; for protection during traumatic brain injury through the effect on mitochondrial function, reduction of inflammation and attenuation of and improvement in re-profusion with decreased re-profusion injury; for reduction of traumatic brain injury; and for treating prion disease, such as Creutzfeldt-Jakob disease and mad cow disease, by acting as an NMDA receptor antagonist, by enhancing intracellular levels of the anti-apoptotic protein Bcl-2; and by increasing antioxidants to glutathione. NAC amide can be used in neural protection, mitochondrial preservation and therapy potential after nerve injury, particularly to prevent primary sensory neuronal death.

Traumatic brain injury includes concussion, contusion or laceration. Traumatic brain injury can be of any severity. The traumatic brain injury can be mild, moderate or severe. The traumatic brain injury can be accompanied by cerebral hemorrhage. Cerebral hemorrhage includes epidural hematoma, subdural hematoma, subarachnoid hemorrhage, and intraventricular hemorrhage. Symptoms of traumatic brain injury include headache, vomiting, nausea, lack of motor coordination, dizziness, difficulty balancing, lightheadedness, blurred vision or tired eyes, ringing in the ears, bad taste in the mouth, fatigue or lethargy, changes in sleep patterns, convulsions, an inability to awaken, dilation of one or both pupils, slurred speech, aphasia, dysarthria, weakness or numbness in the limbs, loss of coordination, confusion, restlessness, agitation, changes in appropriate social behavior, deficits in social judgment, cognitive changes, problems with sustained attention, processing speed, and executive functioning and alexithymia. NAC amide can be used to treat any of these types of traumatic brain injuries and to improve any of the symptoms associated with traumatic brain injury.

In another embodiment, the invention embraces methods and compositions comprising NAC amide for protecting cells and tissues from radiation-induced oxidative stress. In accordance with this embodiment, NAC amide is superior to NAC in protecting tissues from radiation-induced oxidative stress. (Example 2). The medical crisis following the Chernobyl incident and the threat of a terrorist nuclear attack have raised awareness that high-dose total body irradiation may occur and result in death due to the induction of three potentially lethal cerebrovascular, gastrointestinal and hematopoietic clinical syndromes, which result from high dose radiation exposure. The combination of the prodromal syndrome followed by the gastrointestinal syndrome and bone marrow death induces dehydration, anemia, and infection that lead to irreversible shock. Current treatment for the subacute gastrointestinal and hematopoietic syndromes includes supportive therapy such as plasma volume expansion, platelets, and antibiotics to prevent dehydration and infection and promote bone marrow repopulation. Human total body exposure to a radiation dose above 10 Gy has been regarded as uniformly fatal. With therapeutic intervention, survival may be possible up to 15 Gy of total body irradiation, but beyond 20 Gy the symptoms would not be manageable.

The systemic damage observed following irradiation is partially due to the overproduction of reactive oxygen species (ROS), which disrupt the delicate pro-oxidant/antioxidant balance of tissues leading to protein, lipid and DNA oxidation. For example, oxidation of the glucosamine synthetase active site sulfhydryl groups is a key factor in the toxicity of the gastrointestinal syndrome. Polyunsaturated fatty acids, when exposed to ROS, can also be oxidized to hydroperoxides that decompose in the presence of metals to hydrocarbons and aldehydes such as malondialdehyde (MDA). This lipid peroxidation can cause severe impairment of membrane function through increased membrane permeability and membrane protein oxidation. DNA oxidation can lead to strand breakage and consequent mutation or cell death. GSH is the principal intracellular thiol responsible for scavenging ROS and maintaining the oxidative balance in tissues, such as plasma, brain, kidney, liver and lung. In accordance with this embodiment, NAC amide significantly improves GSH levels in these tissues after radiation exposure. (Example 2). The prevention of spinal cord damage resulting from radiation exposure is also encompassed by the use of NAC amide.

In another embodiment, the present invention encompasses methods and compositions comprising NAC amide for stimulating endogenous production of cytokines and hematopoietic factors, comprising administering or introducing NAC amide to cells, tissues, and/or a subject in need thereof for a period of time to stimulate the endogenous production. NAC amide can be used to stimulate production of cytokines and hematopoietic factors, such as but not limited to, TNFB-α, IFN-α, IFN-β, IFN-γ, IL-1, IL-2, IL-6, IL-10, erythropoietin, G-CSF, M-CSF, and GM-CSF, which are factors that modulate the immune system and whose biological activities are involved in various human diseases, such as neoplastic and infectious diseases, as well as those involving hematopoiesis and immune depressions of various origin (such as, without limitation, erythroid, myeloid, or lymphoid suppression).

As used herein, "endogenous" means naturally occurring within a cell, tissue, or organism, or within a subject.

In another embodiment, the present invention encompasses methods and composition comprising NAC amide for detecting NAC-amide responsive changes in gene expression in a cell, tissue, and/or a subject, comprising administering or introducing NAC amide or derivative of NAC amide to the cell, tissue, and/or subject for a period of time to induce changes in gene expression and detecting the changes in gene expression. The cell can be an endothelial cell, smooth muscle cell, immune cell such as erythroid, lymphoid, or myeloid cell, progenitors of erythroid, lymphoid, or myeloid cells, epithelial cell, fibroblasts, neuronal cell and the like. The tissue can be any tissue of the subject, such as hair, skin, or nail tissue, vascular tissue, brain tissue, among many others. Preferably, the changes in gene expression are detected by microarray analysis, but other detection means can encompass, without limitation, reverse-transcription polymerase chain reaction (RT-PCR), Northern Blotting, immunofluorescence, immunoblotting, or enzyme-linked immunosorbent assay, all of which are familiar techniques to those skilled in the art.

NAC amide and derivatives of NAC amide can induce changes in, for example, endothelial cells that are indicative of an anti-angiogenic effect. NAC has been shown to inhibit chemotaxis of endothelial cells in culture, and produce anti-angiogenic effects, such as modulation of genes responsible for blood vessel growth and differentiation, through its antioxidant effects and upregulation of angiostatin (Pfeffer, U. et al, (2005) Mut. Res. 591: 198-211). Thus, NAC amide and NAC amide derivatives can be used to inhibit angiogenesis as an anti-cancer agent, for example, by preventing or inhibiting tumor growth and metastasis.

Cells, tissues, and/or a subject can be exposed to stimuli in the presence of NAC amide or derivatives of NAC amide. Stimuli include, for example, cells cultured in the presence of chemotactic or chemoattractant agents, like chemokines CXCL1-16, CCL1-27, XCL1, XCL2, RANTES, MIP 1-5 (alpha, beta, and gamma isoforms), MCP-1 through 5, and the like. Cells, tissues, and subjects can also be stimulated with pharmaceutical agents, drugs, or treatment modalities. After stimulation, DNA, RNA, or protein can be isolated from the cells, tissues, and/or subject, and changes in gene expression can be detected. For example, total RNA can be isolated from cells according to standard techniques known in the art and resultant cDNAs can be synthesized and subsequently hybridized to a solid support, such as a silicon chip for microarray analysis. Expression data and changes in the expression of genes in response to the stimuli can then be analyzed using computer software programs, such as Gene-Spring (Silicon Genetics).

Non-limiting examples of such genes that exhibit changes in their expression include genes involved in or pertaining to cellular adhesion, apoptosis, chemokine and cytokine biosynthesis, synthesis of extracellular matrix components, endothelium, inflammation, MAP kinases, metalloproteinases, NF-κB, nitric oxide, transforming growth factor (TGF) signaling, and blood vessels. Pfeffer et al reported that a plurality of NAC-responsive genes that are modulated (i.e., up- or downregulated) include HSP40 (heat shock protein 40; DnaJ homolog), SERCA2 (Ca2+ transporting ATPase in cardiac muscle), MKP2 (MAP kinase phosphatase), TIP30 (HIV-1 Tat interactive protein 2), BTG1 (B-cell translocation gene 1), TXL (thioredoxin-like), CRADD (Death receptor adaptor protein), WSX1 (Class I cytokine receptor), EMAP2 (endothelial monocyte-activating protein), Jagged 1 (ligand for Notch receptor), MEAS (hyaluronoglucosaminidase), VRNA (Integrin αV), COL4A1 (Type IV collagen α1), uPA (urokinase plasminogen activator), CPE (carboxypeptidase E), TSPAN-6 (transmembrane 4 superfamily member 6), FGFB (basic fibroblast growth factor), I-TRAF (TRAF interacting factor), CDHH (cadherin 13), IL10RB (Interleukin-10 receptor β), MAP-1 (modulator of apoptosis 1), hCOX-2 (cyclooxygenase-2), CAS-L (Cas-like docking protein), CED-6 (CED-6 protein), CX37 (gap junction protein α4), ABCG1 (ATP-binding cassette protein, subfamily G), TRAIL (TNF ligand superfamily member 10), and ESEL (endothelial adhesion molecule 1; Selectin E), as well as CHOP (DNA-damage-inducible transcript 3), PIM2 (pim-2 oncogene, MIF-1 (homocysteine-inducible protein), PIG-A (phosphatidylinositol glycan, class A), KIAA0062, HK2 (hexokinase 2), UDPGDH (UDP-glucose dehydrogenase), ERF2 (Zinc finger protein 36, C3H type-like 2), RAMP (Zinc finger protein 198), Doc1 (Downregulated in ovarian cancer 1), GBP-1 (Guanylate-binding protein 1, interferon-inducible), GR (glucocorticoid receptor), ENH (LIM protein—enigma homolog), Id-2H (Inhibitor of DNA binding 2), BPGM (2,3-bisphosphoglycerate mutase), HOXA4 (Homeobox A10), EFNB2 (ephrin-B2), ART4 (Dombrock blood group), KIAA0740 (Rho-related BTB domain containing protein 1).

In another embodiment, the present invention encompasses methods and compositions comprising NAC amide for stimulating macrophages and neutrophils to phagocytize infectious agents and other foreign bodies and to eliminate microorganisms, mediated by reactive oxygen species and proteases. NAC amide can be used to improve macrophage function by increasing glutathione availability, which, in turn, will improve alveolar function in fetal alcohol syndrome and to augment premature alveolar macrophage function.

In another embodiment, the invention encompasses methods and compositions comprising NAC amide to increase levels of intracellular reduced glutathione levels, which blocks the formation of irreversibly sickled cell red blood cells. Methods involving the administration of NAC amide to prevent and treat sickle cell anemia and thalassemia are provided.

In another embodiment, the invention encompasses methods and compositions comprising NAC amide to treat *leishmania* through the mechanism of histopathological modulation, in which cytokine pattern is modified as demonstrated by a sustained higher frequency of interferon-γ (IFN-γ) and tumor necrosis factor alpha producing cells. NAC amide is used in the modulation of effector responses in animals, in conjunction with bi-glutathione.

In an embodiment, NAC amide is used to down-regulate cytokine synthesis, activation and downstream processes and/ or to exert an antagonistic effect on pro-inflammatory signals. Such an effect is beneficial in the treatment of many diseases in which cytokines participate in the pathophysiology of the disease. For example, cytokines, which are mediators of oxidative stress, can alter the redox equilibrium by affecting GSH/oxidized glutathione disulfide (GSSG) shuttling and recycling. (For a review of the glutathione-mediated regulation of cytokines and the role of antioxidants, see, J. J. Haddad, 2005, Mol. Immunol., 42(9):987-1014; and J. J. Haddad, 2002, Cellular Signalling, 14(11):879-897). Additionally, liver injury related to the administration of certain drugs can be initiated or intensified by inflammation states that stimulate unregulated production of proinflammatory cytokines or growth factors, such as interferon γ, which leads to the downregulation of enzymes and proteins involved in drug metabolism and elimination. NAC amide, or derivative thereof as an agent that can decrease proinflammatory cytokine levels, is thus useful for preventing and/or managing drug-induced hepatocytoxicity.

In another embodiment, the invention encompasses methods and compositions comprising NAC amide or a derivative thereof for use as a chemoprotectant against bone marrow toxicity after or during chemotherapy, including alkylators with or without glutathione depletion.

In another embodiment, the invention encompasses methods and compositions comprising NAC amide or a derivative thereof to treat various aspects of sepsis, particularly bacterial sepsis and septic shock, including gram-negative septic shock. NAC amide and its derivatives can act as an inhibitor of the nuclear factor NF-κB, which prevents staphylococcal enterotoxin A (SCC) fever by acting through the human peripheral blood mononuclear cells to block the stimulation and synthesis or release pyrogenic cytokines and to block inflammatory sponsors through the regulation of genes in coding for proinflammatory cytokines. In accordance with this embodiment, NAC amide or a derivative thereof is used to block lipid peroxidation and to improve the disease status in children with acute purulent meningitis and encephalitis. NAC amide and its derivatives can be used to block pertussis toxin secretion by *Bordetella pertussis* and for the treatment of lethal sepsis by limiting inflammation and potentiating host defense. Because decreased bacterial colonies improve survival, migration of neutrophils to the site of infection and to a distant site is upregulated and optimal GSH levels are important for an efficient response to sepsis. In addition, ROS release by immune cells are important mediators in sepsis and septic shock. During a normal immune response antioxidant serves to down-regulate the ongoing immune response mostly through modulation of proinflammatory mediators.

In another embodiment, methods and compositions comprising NAC amide or a derivative thereof can be used in the treatment of infection and disease caused by microorganisms and the like, such as bacteria, parasites, nematodes, yeast, fungi, plasmodia, *mycoplasma*, spores, and the like, e.g., malarial infections and tuberculosis and *rickettsia* infection. In a related aspect, it has recently been found that infection by a number of types of bacteria, such as *Streptococcus, Staphylococcus, Salmonella, Bacillus* (*Tubercule bacillus*) etc., which cause diseases in humans, induce a direct response by leukocytes (i.e., white blood cells) in the body, to increase their levels of hypoxia inducible transcription factor-1, or HIF-1. The HIF-1 protein binds to cellular DNA and activates specific genes to help cells function in a low oxygen environment. HIF-1, in turn, stimulates the white blood cells to produce and release antimicrobial compounds, e.g., small proteins, enzymes and nitric oxide, that work together to kill bacteria. In addition, it has been found that low oxygen levels, which occur at the site of an infection, activate HIF-1 in macrophages and neutrophils, which typically ingest and destroy invading microorganisms. The greater the increase in HIF-1 levels in the white blood cells, the greater their antibacterial activity. In accordance with this aspect of the invention and in view of the influence of HIF-1 in regulating the killing functions of white blood cells, an alternative to the direct killing of bacteria, etc. is to use agents, e.g., small molecules, that promote HIF-1 activity in white blood cells to boost their bacterial killing ability, thereby promoting a resolution to infection through the actions of the immune system's natural defense mechanisms. One such agent is NAC amide, which can be used in a method of killing or inhibiting the growth of microorganisms by increasing cellular levels of HIF-1, i.e., HIF-la, thereby enhancing the capacity of white blood cells, such as macrophages, to kill the microorganisms. Because N-acetyl-L-cysteine, NAC, a glutathione (GSH) precursor and a ROS scavenger, which does not possess the enhanced properties of lipophilicity and cell permeability of NAC amide, has been shown to induce HIF-1α in epithelial cells (J. J. E. Haddad et al., 2000, J. Biol. Chem., 275:21130-21139), the use of NAC amide to modulate HIF-la production in white blood cells in order to activate the bacterial killing potential of these cells is embraced as an improved antioxidant treatment provided by the present invention. The present invention is further directed to the use of NAC amide or a derivative thereof as a bacteriostatic agent when used as a treatment for bacterial infection, particularly antibiotic resistant, or multi-antibiotic resistant bacteria such as tuberculosis-causing microorganisms.

In a related embodiment, the present invention is directed to the use of NAC amide or a derivative thereof as a biodefensive agent for inducing the killing of infecting or contaminating microorganisms. These types of microorganisms may pose a severe health threat if they should be disseminated to the public and/or genetically altered so as to be antibiotic resistant. The following lists set forth categories of microorganisms, viruses, diseases and agents for which NAC amide or its derivative is provided as a suitable countermeasure, used alone, or in combination with other active compounds, agents and substances to treat affected organisms and/or cells thereof:

Infectious Diseases: Aflatoxins, Alphavirus Eastern equine encephalitis virus, Alphavirus Venezuelan equine encephalitis virus, Antibiotic-resistant *Mycobacterium tuberculosis*, Arenavirus Junin Virus, Arenavirus Lassa Virus, *Ascaris lumbricoides* (roundworm), Avian influenza, *Bacillus anthracis* (anthrax), *Borrelia, Brucella, Burkholderia mallei* (glanders), *Chlamydia psittaci* (parrot fever), *Chlamydia trachiomitis* (Trachoma), *Clostridium botulinum* (botulism), *Clostridium perfringens* (gas gangrene), *Coccidioidomycosis immitis, Coxiella burnetti* (Q fever), *Cryptosporidium par-*

*vum*, Dinoflagellate neurotoxin (Paralytic Shellfish Toxin), *Drancunculus medianensis* (guinea worm), Ebola virus, *Entamoeba histolytica* (amoebiasis), Epsilon toxin of *Clostridium perfringens, Escherichia coli*, Flavivirus Yellow Fever virus (e.g., West Nile virus, Dengue), *Francisella tularensis* (tularemia), *Giardia lamblia* (giardiasis), Hantavirus, Henipavirus Nipah virus (Nipa encephalitis), HIV and AIDS, Influenza, *Leishmania donovane*, Marburg virus, Methicillin-resistant *staphylococcus aureus* (MRSA), *Mycobacterium leprea* (leprosy), *Mycobacterium ulcerans* (Burulu ulcer), Nairo virus Crimean-Congo hemorrhagic fever virus, *Necator Americanus/Ancylostoma duodenale* (hookworm), *Onchocerca volvulus* (river blindness), Orthopox virus, Pathogenic *Haemophilus*, Pathogenic *Salmonella*, Pathogenic *Shigella*, Pathogenic *Streptococcus*, Phlebovirus Rift Valley fever virus, *Plasmodium falciparum, P. ovale, P. vivax, P. malariae* (malaria), Ricin toxin (castor bean oil), *Rickettsia rickettsii* (Rocky Mountain Spotted Fever), *Rickettsia typhi* (typhus), *Salmonella typhi* (typhoid fever), *Schistosoma mansoni, S. haematobium, S. japonicum, Shigella dysenteriae*, Smallpox, *Staphylococcus* enterotoxin B, Tickborne encephalitis virus, Tickborne hemorrhagic fever viruses, *Toxoplasma gondii, Treponema*, Trichothecene Mycotoxins, *Trichuris trichiura* (whipworm), *Trypanosoma brucei, T. gambiense* or *T. rhodesiense, Vibrio* species (cholera), *Wuchereria bancrofti* and *Brugia malayi, Yersinia pestis* (black death).

Other Threats: Blister agents, including Lewisite, nitrogen and sulfur mustards; Blood agents, including hydrogen cyanide and cyanogens chloride; Exotic agents, including hybrid organisms, genetically modified organisms, antibiotic-induced toxins, autoimmune peptides, immune mimicry agents, binary bioweapons, stealth viruses and bioregulators and biomodulators; Heavy metals, including arsenic, lead and mercury; incapacitating agents, including BZ; nerve agents, including Tabun, Sarin, Soman, GF, VX, V-gas, third generation nerve agents, organophosphate pesticides and carbamate insecticides; nuclear and radiological materials, pulmonary agents, including phosgene and chorine vinyl chloride; volatile toxins, including benzene, chloroform and trihalomethanes. In accordance with the present invention, NAC amide or derivatives thereof can serve as an innovative treatment for known and emerging natural infectious disease threats, as well as trauma, e.g., excessive bleeding and other events, associated with and/or resulting from an act of bioterrorism.

Illustratively, *Rickettsia*, which causes the pathogenesis of typhus and spotted fever rickettsioses, results in serious adverse vascular and hemorrhagic conditions, (e.g., increased vascular permeability and edema) notably in the brain and lung, following its entry into vascular endothelial cells. *R. rickettsii*-infected endothelial cells produce ROS causing peroxidative damage to cell membranes. (D. J. Silverman et al., 1990, Ann. N.Y. Acad. Sci., 590:111-117; D. H. Walker et al., 2003, Ann. N.Y. Acad. Sci., 990:1-11). Because the oxidative-stress mediated damage to *R. rickettsii*-infected endothelial cells is associated with the depletion of host components such as GSH and levels of catalase that act as host defenses against ROS-induced damage, the concentration of hydrogen peroxide and ROS increase in the cells to cause ROS-induced cellular damage. In a similar manner, cells, e.g., fibroblasts that are infected with *Mycoplasma* (e.g., *Mycoplasma pneumoniae*) also produce increased intracellular levels of hydrogen peroxide and decreased levels of catalase, resulting in oxidative stress that can lead to death of the infected cells. (M. Almagor et al., 1986, Infect. Immun., 52(1):240-244). To provide an ameliorating effect of oxidative stress induced in cells by infecting microorganisms such as *Rickettsia, Mycoplasma*, etc., NAC amide or a derivative thereof is provided to an infected host as an antioxidant therapeutic. NAC amide administration to cells and/or organisms (e.g., infected host mammals) in accordance with the present invention, alone or in combination with other agents and/or antioxidants, can limit the amount and/or extent of oxidative damage that is induced by microbial infection.

In another embodiment, the invention encompasses methods and compositions comprising NAC amide or a derivative thereof for use in preventing periventricular leukomalacia (PVL). NAC amide or a derivative thereof may provide neural protection and attenuate the degeneration of OPCs against LPS evoked inflammatory response in white matter injury in developing brain. Moreover, NAC amide or a derivative thereof may be used as a treatment for placental infection as a means of minimizing the risk of PVL and cerebral palsy (CP).

In another embodiment, the invention encompasses methods and compositions comprising NAC amide or a derivative thereof for the treatment of osteoporosis. The tumor necrosis factor member RANKL regulates the differentiation, activation and survival of osteoclasts through binding of its cognate receptor, RANK. RANK can interact with several TNF-receptor-associated factors (TRAFs) and activate signaling molecules including Akt, NF-κB and MAPKs. Although the transient elevation of reactive oxygen species by receptor activation has been shown to act as a cellular secondary messenger, the involvement of ROS in RANK signal pathways has not been characterized. RANKL can stimulate ROS generation and osteoclasts. According to this embodiment, NAC amide can be used to pretreat or treat osteoclasts so as to achieve a reduction in RANKL-induced Akt, NF-κB, and ERK activation. The reduced NF-κB activity by NAC amide may be associated with decreased IKK activity and IκBα phosphorylation. Pretreatment with NAC amide or a derivative thereof can be used to reduce RANKL-induced actin ring formation required for bone resorbing activity and osteoclast survival. The methods and compositions comprising NAC amide or a derivative thereof can be used for the improvement of osteoporosis through blockage and interference with osteoclasts, and to lower reactive oxidative stress levels so as to have beneficial effects on preventing bone loss by reducing RANKL-induced cellular function.

In a related embodiment, NAC amide or a derivative thereof is used in the treatment of osteoporosis by blockage of thiol thioredoxin-1, which mediates osteoclast stimulation by reactive oxidation species (ROS), as well as blockage of TNF-α, which causes loss of bone, particularly in circumstances of estrogen deficiency.

In another embodiment, the invention embraces methods and compositions comprising NAC amide or a derivative thereof are used for the treatment of polycystic ovary syndrome. NAC amide or a derivative thereof may also be used as a therapeutic agent to ameliorate the homocysteine and lipid profiles in PCOS-polycystic ovary syndrome.

In another embodiment, the invention encompasses the use of NAC amide or a derivative thereof in treatments and therapies for toxin exposure and conditions related thereto, e.g., sulfur mustard (HD-induced lung injury). Treatment of individuals having been exposed to toxins or suffering from toxin exposure with NAC amide or a derivative thereof may reduce neutrophil counts to achieve a decreased inflammatory response. NAC amide and its derivatives may be useful as a treatment compound for patients having sulfur mustard vapor exposure induced lung injury. Administration of NAC amide or a derivative thereof can be either orally or as a bronchioalveolar lavage. As an agent having anti-glutamate toxin activity, NAC amide and its derivatives are useful in methods and compositions for the blockage of brain and/or lung damage and cognitive dysfunction in mechanical warfare agents including CW, vesicants, sulfur mustard, nitrogen mustards, chloroethyl amine, lewisite, nerve agents O-ethyl S-(2-[diisopropylamino]ethyl) methyl phosphorothioate (VX), tabun (GA) and sarin (GB) and soman DG and the blood agents cuianogenchloride, and in the prevention of organophosphate induced convulsions and neuropathological damage.

In another embodiment, the present invention encompasses methods and compositions comprising NAC amide for use in the treatment of burn trauma. NAC amide or a derivative thereof can block NF-κB, which has been shown to reduce burn and burn sepsis. NAC amide or a derivative thereof can be used to protect microvascular circulation, reduce tissue lipid peroxidation, improve cardiac output and reduce volume of required fluid resuscitation. NAC amide or a derivative thereof can be used in the prevention of burn related cardiac NF-κB nuclear migration, and improve cardiomyocyte secretion of TNF-α, IL-1β, and IL-6 and to improve cardiac malfunction. An association between cellular oxidative stress and burn-mediated injury provides an avenue for administering NAC amide or a derivative thereof as an antioxidant that can inhibit free radical formation and/or scavenge free radicals to protect tissues and organs in patients with burn injury.

In another embodiment, the present invention encompasses methods and compositions comprising NAC amide or a derivative of NAC amide for use in the prevention of lung injury due to the adverse effects of air pollution and diesel exhaust particles.

In another embodiment, the present invention encompasses methods and compositions comprising NAC amide or a derivative thereof for use in the treatment and therapy of cardiovascular disease and conditions. NAC amide and its derivatives can be used as a blocker of angiotensin-converting enzyme. In acute myocardial infarction, NAC amide or a derivative thereof can be used to decrease oxidative stress, and to cause more rapid re-profusion, better left ventricular preservation, reduced infarct size, better preservation of global and regional left ventricular function and modification of QSR complex morphology and ECG. NAC amide or a derivative thereof can also be used in the treatment of focal cerebral ischemia with protection of the brain and reduction of inflammation in experimental stroke. NAC amide can be used in the treatment of reperfusion injuries, as well as apoptosis of myocardial endothelial cells and interstitial tissue. As a nutriceutical, NAC amide or a derivative thereof may assist in the elevation of nitric oxide levels, play an important role in the management of cardiovascular disease, reduce chronic inflammation in cardiovascular disease and prevent restenosis of cardiovascular stents placed in coronary arteries and carotid arteries. NAC amide and its derivatives can be used in the prevention of cardiac failure following MI and cardiomyopathy due to prevention of oxidative stress and improvement of left ventricular remodeling. Use of NAC amide or a derivatives of NAC amide in this capacity supports the involvement of oxidative stress in myocardial vascular dysfunction and hypertension and provides a role for antioxidant strategies to preserve the myocardial microvasculature. NAC amide or a derivative thereof can also be used in the prevention of oxidized proteins in muscles.

In another embodiment of the present invention, method and compositions comprising NAC amide or a derivative thereof can be used to treat arterial sclerosis and to increase high density lipoprotein (HDL)-cholesterol serum levels in hyperlipidemic and normal lipidemic individuals with documented coronary stenosis. NAC amide or a derivative thereof can also be used to decrease coronary and alpha-beta stress; to prevent further myocardial infarctions; and to cause a reduction in body fat thereby improving glucose tolerance, particularly in overweight or obese individuals. NAC amide or a derivative thereof be used to improve muscular performance and decrease levels of tumor necrosis factor in old age.

In other embodiments, the present invention is directed to the use of method and compositions comprising NAC amide or a derivative thereof in the treatment of thalassemic blood by ameliorating oxidative stress in platelets. The activation of platelets causes thromboembolic consequences and produces a hypercoagulable state that is amenable to treatment by the antioxidant NAC amide or a derivative thereof. In an embodiment, NAC amide or a derivative thereof is useful as a wound dressing to permit enhancement of neutrophil function. In an embodiment, NAC amide or a derivative thereof is used to block the effects of leptin, which is a cardiovascular risk factor in diabetic patients. In an embodiment, NAC amide or a derivative thereof is used in the treatment of total plasma homocysteine and cysteine levels with increased urinary excretion, as well as in the treatment for hyperhomocysteinemic conditions, to improve oxidative stress. It has been found that elevated levels of homocysteine pose a significant risk in vascular disease, such as atherosclerosis, venous thrombosis, heart attack and stroke, as well as neural tube defects and neoplasia. Homocysteine promotes free radical reactions. In patients with defective homocysteine metabolism, relatively high levels of homocysteine are present in the blood. Thus, in accordance with this invention, NAC amide or a derivative thereof is administered to patients with elevated homocysteine levels. In an embodiment, NAC amide or a derivative thereof is used as a chemoprotectant against bone marrow toxicity after or during chemotherapy, e.g., alkylators, with or without accompanying glutathione depletion. In an embodiment, NAC amide or a derivative thereof is used in the treatment of lithium induced renal failure. In an embodiment, NAC amide or a derivative thereof is used in the treatment of pro static inflammation, which may contribute to pro static carcinogenesis and inflammation.

In another embodiment, NAC amide or a derivative thereof is used in pulmonary disease medicine, particularly in oxygen-mediated lung disease. NAC amide or a derivative thereof can improve oxygenation in cardiopulmonary bypass during coronary artery surgery and is useful in the treatment of chronic obstructive pulmonary disease and pulmonary hypertension. In an embodiment, NAC amide or a derivative thereof is used in the treatment of injury in the lung due to high-energy impulse noise-blasts, which can induce antioxidant depletion. Thus, the administration of NAC amide or its derivatives provide an advantageous antioxidant source. NAC amide or a derivative thereof is particularly useful if provided as a supplement prior to noise blast exposure. NAC amide or a derivative thereof is useful in the treatment of asthma with increased oxidative stress. NAC amide or a derivative thereof is useful for the treatment of adult respiratory distress syndrome; in the treatment of pulmonary fibrosis, in the treatment of idiopathic pulmonary fibrosis and asbestos exposure; and in the treatment of chronic lung rejection. Further, NAC amide or a derivative thereof is contemplated for use in occupational isocyanate exposure and the development of isocyanate allergy, which is believed to develop by two processes, namely, isocyanate-protein conjugation and airway epithelial cell toxicity. More specifically, NAC amide or a derivative thereof can serve to protect against hexamethylene diisocyanate (HDI) conjugation to cellular proteins and to reduce HDI toxicity to human airway epithelial cells following isocyanate exposure. Thus, NAC amide or a derivative thereof can help to prevent the development of allergic sensitization and asthma that are associated with this occupational hazard.

In another embodiment, the present invention encompasses the use of NAC amide or a derivative thereof to inhibit HIV replication in chronically and acutely infected cells. NAC amide can be used in GSH replacement therapy, as NAC amide and its derivatives may interfere with the expression of the integrated HIV genome, thus, attacking the virus in a manner that is different from that of the currently employed anti-retrovirals, e.g., AZT, ddI, ddC or D4T. NAC amide or a derivative thereof can also be beneficial in countering the excess free radical reactions in HIV infection, which may be attributable to: 1) the hypersecretion of TNF-α, by B-lymphocytes in HIV infection, and 2) the catalysis of arachidonic acid metabolism by the gp120 protein of HIV. The physiologic requirements for antioxidants by key cell types of the immune system, and the ability of macrophages to take up intercellular antioxidants, as well as to metabolically interact with T-lymphocytes to indirectly cause their antioxidant levels to increase, offer additional reasons that NAC amide or a derivative thereof is useful for correcting antioxidant deficiency in patients with HIV/AIDS. NAC amide and its derivatives can serve as a suppressant of viral and bacterial species in vaginal tissues by the use of intravaginal placement of gel induced thiol.

Because HIV is known to start pathologic free radical reactions which lead to the destruction of antioxidant molecules, as well as the exhaustion of GSH and destruction of cellular organelles and macromolecules, NAC amide and its derivatives can be used to restore antioxidant levels in a mammal in need thereof, to arrest the replication of the virus at a unique point, and specifically prevent the production of toxic free radicals, prostaglandins, TNF-α, interleukins, and a spectrum of oxidized lipids and proteins that are immunosuppressive and cause muscle wasting and neurological symptoms. The administration of NAC amide or a derivative thereof to elevate or replace antioxidant levels could slow or stop the diseases progression safely and economically.

Because certain viral infections, such as infection by HIV, are associated with reduced antioxidant levels, an aspect of this invention is to increase intracellular levels of antioxidant in infected cells, as well as to increase extracellular of antioxidant, by introducing or administering AD3 so as to interfere with the replication of HIV and to prevent, delay, reduce or alleviate the cascade of events that are associated with HIV infection. Because AIDS may also be associated with reduced GSSG levels, providing an amount of NAC amide to cells and/or to an individual in need thereof, can overcome any interference with de novo synthesis of antioxidant such as GSH, as well as the oxidation of existing GSH, which may occur in HIV infected cells. In accordance with the present invention NAC amide or a derivative thereof is used to inhibit cytokine-stimulated HIV expression and replication in acutely infected cells, chronically infected cells, and in normal peripheral blood mononuclear cells. NAC amide or derivatives thereof can be used to effect concentration-dependent inhibition of HIV expression induced by TNF-α or IL-6 in chronically infected cells. Due to NAC amide's superior ability to cross cellular membranes and enhanced lipophilic properties, NAC amide and derivatives thereof can be used at lower concentrations as compared to NAC or GSH, such as 2-fold, 5-fold, 10-fold, 100-fold, 1000-fold, 10,000-fold or lower, concentrations.

Further, the depletion of antioxidants by HIV in infected cells is also associated with a process known as apoptosis, or programmed cell death. By providing NAC amide or a derivative thereof to HIV infected individuals and/or cells, the intercellular processes, which artificially deplete GSH and which may lead to cell death can be prevented, interrupted, or reduced. Similarly, the NAC amide thiol can be used as a blocker of bio-replication from West Nile Virus and protection of cells from the cytopathic effect after infection of West Nile Virus, as well as other RNA and DNA virus infections.

In accordance with the invention, NAC amide or a derivative thereof may be administered by several routes that are suited to the treatment or therapy method, as will be appreciated by the skilled practitioner. Nonlimiting examples of routes and modes of administration for NAC amide and its derivatives include parenteral routes of injection, including subcutaneous, intravenous, intramuscular, and intrasternal. Other modes of administration include, but are not limited to, oral, inhalation, topical, intranasal, intrathecal, intracutaneous, ophthalmic, vaginal, rectal, percutaneous, enteral, injection cannula, timed release and sublingual routes. Administration of NAC amide and its derivatives may also be achieved through continuous infusion. In one embodiment of the present invention, administration of NAC amide and its derivatives may be mediated by endoscopic surgery. For the treatment of various neurological diseases or disorders that affect the brain, NAC amide or a derivative thereof can be introduced into the tissues lining the ventricles of the brain. The ventricular system of nearly all brain regions permits easier access to different areas of the brain that are affected by the disease or disorder. For example, for treatment, a device, such as a cannula and osmotic pump, can be implanted so as to administer a therapeutic compound, such as NAC amide, or derivative thereof as a component of a pharmaceutically acceptable composition. Direct injection of NAC amide and its derivatives are also encompassed. For example, the close proximity of the ventricles to many brain regions is conducive to the diffusion of a secreted or introduced neurological substance in and around the site of treatment by NAC amide.

For administration to a recipient, for example, injectable administration, a composition or preparation formulated to contain water-soluble NAC amide or a derivative thereof is typically in a sterile solution or suspension. Alternatively, NAC amide or a derivative thereof can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Nonlimiting examples of excipients suitable for use include water, phosphate buffered saline (pH 7.4), 0.15M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures.

Formulations comprising NAC amide or a derivative thereof for topical administration may include but are not limited to lotions, ointments, gels, creams, suppositories, drops, liquids, sprays and powders. NAC amide or a derivative thereof may be administered to mucous membranes in the form of a liquid, gel, cream, and jelly, absorbed into a pad or sponge. Conventional pharmaceutical carriers, aqueous, powder or oily bases, thickeners and the like may be necessary or desirable. Compositions comprising NAC amide or a derivative thereof for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include, but are not limited to, sterile solutions, which may also contain buffers, diluents and other suitable additives.

The present invention also provides a food additive comprising NAC amide or a derivative thereof for mammalian, preferably human, consumption. NAC amide and other cysteine derivatives have been detected in many different food products, including but not limited to, garlic, peppers, turmeric, asparagus, and onions. See, for example, Hsu, C. C., et al, (2004) J. Nutr. 134:149-152 and Demirkol, O. et al, (2004) J. Agric. Food Chem. 52. The food additive can comprise NAC amide or its derivative in a liquid or solid material intended to be added to a foodstuff. The food additives can be added to "food compositions" including any products—raw, prepared or processed—which are intended for human consumption in particular by eating or drinking and which may contain nutrients or stimulants in the form of minerals, carbohydrates (including sugars), proteins and/or fats, and which have been modified by the incorporation of a food additive comprising NAC amide or a derivative of NAC amide as provided herein. The present modified food compositions can also be characterized as "functional foodstuffs or food compositions". "Foodstuffs" can also be understood to mean pure drinking water.

The term "food additive" is understood to mean any a liquid or solid material intended to be added to a foodstuff. This material can, for example, have a distinct taste and/or flavor, such as a salt or any other taste or flavor potentiator or modifier. It is to be noted, however, that the food additive comprising NAC amide or a NAC amide derivative does not necessarily have to be an agent having a distinct taste and/or flavor.

Other food additives that can be added in combination with NAC amide, or in food additive formulations of NAC amide include, but are not limited to, acids which are added to make flavours "sharper", and also act as preservatives and antioxidants, such as vinegar, citric acid, tartaric acid, malic acid, fumaric acid, lactic acid, acidity regulators, anti-caking agents, antifoaming agents, antioxidants such as vitamin C and tocopherols such as vitamin E, bulking agents, such as starch are additives, food coloring, color retention agents, emulsifiers flavors, flavor enhancers, humectants, preservatives, propellants, stabilizers, thickeners and gelling agents, like agar or pectin, and sweeteners.

Doses, amounts or quantities of NAC amide, or derivative thereof as well as the routes of administration used, are determined on an individual basis, and correspond to the amounts used in similar types of applications or indications known to those having skill in the art. As is appreciated by the skilled practitioner in the art, dosing is dependent on the severity and responsiveness of the condition to be treated, but will normally be one or more doses per day, with course of treatment lasting from several days to several months, or until a cure is effected or a diminution of disease state is achieved. Persons ordinarily skilled in the art can easily determine optimum dosages, dosing methodologies and repetition rates. For example, a pharmaceutical formulation for orally administrable dosage form can comprise NAC amide, or a pharmaceutically acceptable salt, ester, or derivative thereof in an amount equivalent to at least 25-500 mg per dose, or in an amount equivalent to at least 50-350 mg per dose, or in an amount equivalent to at least 50-150 mg per dose, or in an amount equivalent to at least 25-250 mg per dose, or in an amount equivalent to at least 50 mg per dose. NAC amide or a derivative thereof can be administered to both human and non-human mammals. It therefore has application in both human and veterinary medicine.

Examples of suitable esters of NAC amide include alkyl and aryl esters, selected from the group consisting of methyl ester, ethyl ester, hydroxyethyl ester, t-butyl ester, cholesteryl ester, isopropyl ester and glyceryl ester.

As described herein, a number of conditions, diseases and pathologies are believed to be associated with reduced intracellular antioxidant levels, including AIDS, diabetes, macular degeneration, congestive heart failure, cardiovascular disease and coronary artery restenosis, lung disease, asthma, virus infections, e.g., toxic and infectious hepatitis, rabies, HIV; sepsis, osteoporosis, toxin exposure, radiation exposure, burn trauma, prion disease, neurological diseases, blood diseases, arterial disease, muscle disease, tumors and cancers. Many of these diseases and conditions may be due to insufficient glutathione levels. Further, exposure to toxins, radiation, medications, etc., may result in free radical reactions, including types of cancer chemotherapy. Accordingly, the present invention provides NAC amide or a derivative thereof as an agent that can treat these diseases and conditions in a convenient and effective formulation, particularly for oral administration. The administration of exogenous NAC amide or a derivative thereof can serve to supplement or replace the hepatic output of GSH and to assist in the maintenance of reduced conditions within the organism. The failure to alleviate free radical reactions allows an undesirable cascade that can cause serious damage to macromolecules, as well as lipid peroxidation and the generation of toxic compounds. Maintaining adequate levels of GSH is necessary to block these free radical reactions. When natural GSH levels are debilitated or jeopardized, NAC amide or a derivative thereof is able to provide efficient and effective remedial action.

NAC amide can form chelation complexes with copper and lead. NAC amide may also form circulating complexes with copper in the plasma. Thus, NAC amide or a derivative thereof can be administered to treat metal toxicity. NAC amide-metal complexes will be excreted, thus reducing the metal load. Thus, NAC amide or a derivative thereof may be administered for the treatment of toxicity associated with various metals, e.g., iron, copper, nickel, lead, cadmium, mercury, vanadium, manganese, cobalt, transuranic metals, such as plutonium, uranium, polonium, and the like. It is noted that the chelation properties of NAC amide are independent from its antioxidant properties. However, because some metal toxicities are free radical mediated, e.g., iron, NAC amide administration may be particularly advantageous for such conditions.

In order to provide high bioavailability, NAC amide or a derivative thereof can be provided in a relatively high concentration in proximity to the mucous membrane, e.g., the duodenum for oral administration. Thus, NAC amide or a derivative thereof can be administered as a single bolus on an empty stomach. The preferred dosage is between about 100-10,000 mg NAC amide or between about 250-3,000 mg NAC amide. Further, the NAC amide or NAC amide derivative formulation can be stabilized with a reducing agent, e.g., ascorbic acid, to reduce oxidation both during storage and in the digestive tract prior to absorption. The use of crystalline ascorbic acid has the added benefit of providing improved encapsulation and serving as a lubricant for the encapsulation apparatus. Capsules, e.g., a two-part gelatin capsule, are dosage forms that protect NAC amide from air and moisture, while dissolving quickly in the stomach. The capsule is preferably a standard two-part hard gelatin capsule of double-O (OO) size, which may be obtained from a number of sources. After filling, the capsules are preferably stored under nitrogen to reduce oxidation during storage. The capsules are preferably filled according to the method of U.S. Pat. No. 5,204, 114, incorporated herein by reference in its entirety, using crystalline ascorbic acid as both an antistatic agent and stabilizer. Further, each capsule preferably contains 500 mg of NAC amide and 250 mg of crystalline ascorbic acid. A preferred composition includes no other excipients or fillers; however, other compatible fillers or excipients may be added. While differing amounts and ratios of NAC amide and stabilizer may be used, these amounts are preferable because they fill a standard double-O capsule, and provide an effective stabilization and high dose. Further, the addition of calcium carbonate is avoided as it may contain impurities and may accelerate the degradation of NAC amide in the small intestine due to its action as a base, which neutralizes stomach acid.

NAC amide or a derivative thereof is advantageously administered over extended periods. Therefore, useful combinations include NAC amide or NAC amide derivatives and drugs intended to treat chronic conditions. Such drugs are well absorbed on an empty stomach and do not have adverse interactions or reduced or variable combined absorption. One particular class of drugs includes central or peripheral adrenergic or catecholenergic agonists, or reuptake blockers, which may produce a number of toxic effects, including neurotoxicity, cardiomyopathy and other organ damage. These drugs are used, for example, as cardiac, circulatory and pulmonary medications, anesthetics and psychotropic/antipsychotic agents. Some of these drugs also have abuse potential, as stimulants, hallucinogens, and other types of psychomimetics. Other free radical initiation associated drugs include thorazine, tricyclic antidepressants, quinolone antibiotics, benzodiazepines, acetaminophen and alcohol. Accordingly, NAC amide or a derivative thereof can advantageously be provided in an oral pharmaceutical formulation in an amount of between about 50-10,000 mg, along with an effective amount of a pharmacological agent that is capable of initiating free radical reactions in a mammal. The pharmacological agent is, for example, an adrenergic, dopaminergic, serotonergic, histaminergic, cholinergic, gabaergic, psychomimetic, quinone, quinolone, tricyclic, and/or steroid agent.

In the following aspects of the invention, formulations of NAC amide or a derivative thereof provide an advantageous alternative to GSH administration. NAC amide or a derivative thereof offers beneficial properties of lipophilicity and cell-permeability, allowing it to more readily enter cells and infiltrate the blood-brain barrier more readily than GSH, NAC or other compounds. The properties of NAC amide or a derivative thereof may increase its bioavailability following administration to provide an improved treatment for the various diseases, disorders, pathologies and conditions as described herein.

Hepatic glutathione is consumed in the metabolism, catabolism and/or excretion of a number of agents, including aminoglycoside antibiotics, acetaminophen, morphine and other opiates. The depletion of hepatic glutathione may result in hepatic damage or a toxic hepatitis. High dose niacin, used to treat hypercholesterolemia, has also been associated with a toxic hepatitis. The present invention therefore encompasses an oral pharmaceutical formulation comprising NAC amide or a derivative thereof in an amount between about 50-10,000 mg, administered in conjunction with an effective amount of a pharmacological agent that consumes hepatic glutathione reserves.

A number of pathological conditions result in hepatic damage. This damage, in turn, reduces the hepatic reserves of glutathione and the ability of the liver to convert oxidized glutathione to its reduced form. Other pathological conditions are associated with impaired glutathione metabolism. These conditions include both infectious and toxic hepatitis, cirrhosis, hepatic primary and metastatic carcinomas, traumatic and iatrogenic hepatic damage or resection. The present invention encompasses a pharmaceutical formulation comprising NAC amide or a derivative of NAC amide and an antiviral or antineoplastic agent. The antiviral or antineoplastic agent is, for example, a nucleoside analog.

Glutathione is degraded, and cysteine is excreted, possibly in the urine. Very high doses of glutathione may therefore result in cysteinuria, which may result in cysteine stones. Other long term toxicity or adverse actions may result. Therefore, a daily intake of greater than about 10 gm for extended period should be medically monitored. On the other hand, individual doses below about 50 mg are insufficient to raise the concentration of the duodenal lumen to high levels to produce high levels of absorption, and to provide clinical benefit. Therefore, the formulations according to the present invention have an NAC amide or NAC amide derivative content greater than 50 mg, and are provided in one or more doses totaling up to about 10,000 mg per day.

In the treatment of HIV infection, it is believed that the oral administration of a relatively high dose bolus of glutathione, i.e., 1-3 grams per day, on an empty stomach, will have two beneficial effects. First, HIV infection is associated with a reduction in intracellular glutathione levels in PBMs, lung, and other tissues. It is further believed that by increasing the intracellular glutathione levels, the functioning of these cells may be returned to normal. Therefore, the administration of NAC amide or a derivative thereof according to the present invention will treat the effects of HIV infection. Oral administration of NAC amide, or derivative thereof, optionally in combination with ascorbic acid and/or with an antiretroviral agent. It is noted that the transcription mechanisms and control involved in retroviral infection is believed to be relatively conserved among the different virus types. Therefore, late stage retroviral suppression is expected for the various types of human retroviruses and analogous animal retroviruses. It has also been found in in vitro tests that by increasing the intracellular levels of glutathione in infected monocytes to the high end of the normal range, the production of HIV from these cells may be suppressed for about 35 days. This is believed to be related to the interference in activation of cellular transcription of cytokines, including NF-κB and TNF-α. Therefore, the infectivity of HIV infected persons may be reduced, helping to prevent transmission. This reduction in viral load may also allow the continued existence of uninfected but susceptible cells in the body.

NAC amide, or derivative thereof administered according to the present method, can be use in the treatment of congestive heart failure (CHF). In CHF, there are believed to be two defects. First, the heart muscle is weakened, causing enlargement of the heart. Second, peripheral vasospasm is believed to be present, causing increased peripheral resistance. NAC amide or a derivative thereof can be effective in enhancing the effects of nitric oxide, and therefore can be of benefit to these patients by decreasing vasoconstriction and peripheral vascular resistance, while increasing blood flow to the tissues. The present invention thus encompasses the oral administration of NAC amide or a derivative thereof in conjunction with a congestive heart failure medication, for example, digitalis glycosides, dopamine, methyldopa, phenoxybenzamine, dobutamine, terbutaline, aminone, isoproterenol, beta blockers, calcium channel blockers, such as verapamil, propranolol, nadolol, timolol, pindolol, alprenolol, oxprenolol, sotalol, metoprolol, atenolol, acebutolol, bevantolol, tolamolol, labetalol, diltiazem, dipyridamole, bretylium, phenyloin, quinidine, clondine, procainamide, acecainide, amiodarione, disopyramide, encainide, flecanide, lorcainide, mexiletine, tocainide, captopril, minoxodil, nifedipine, albuterol, pargyline, vasodilators, including nitroprusside, nitroglycerin, phentolamine, phenoxybenzamine, hydrazaline, prazosin, trimazosin, tolazoline, trimazosin, isosorbide dinitrate, erythrityl tetranitrate, aspirin, papaverine, cyclandelate, isoxsuprine, niacin, nicotinyl alcohol, nylidrin, diuretics, including furosemide, ethacrynic acid, spironolactone, triamterine, amiloride, thiazides, bumetanide, caffeine, theophylline, nicotine, captopril, salalasin, and potassium salts.

In another of its embodiments, the present invention embraces NAC amide or a derivative thereof to treat hepatitis of various types by oral administration. For example, both alcohol and acetaminophen are hepatotoxic and result in reduced hepatocyte glutathione levels. Therefore, these toxicities may be treated according to the present invention with the use of NAC amide or a derivative thereof. NAC amide and its derivatives may also be effective in the treatment of toxicities to other types of cells or organs, which result in free radical damage to cells or reduced glutathione levels.

Diabetes, especially uncontrolled diabetes, results in glycosylation of various enzymes and proteins, which may impair their function or control. In particular, the enzymes which produce reduced glutathione (e.g., glutathione reductase) become glycosylated and nonfunctional. Therefore, diabetes is associated with reduced glutathione levels, and in fact, many of the secondary symptoms of diabetes may be attributed to glutathione metabolism defects. According to this invention, NAC amide or a derivative thereof can be used to supplement diabetic patients in order to prevent a major secondary pathology. The present invention also encompasses an oral pharmaceutical formulation comprising NAC amide and an antihyperglycemic agent.

High normal levels of glutathione deactivate opiate receptors. Thus, the administration of NAC amide or a derivative thereof may be of benefit for treating obesity and/or eating disorders, other addictive or compulsive disorders, including tobacco (nicotine) and opiate additions. This invention also encompasses administering NAC amide or a derivative thereof in conjunction with nicotine. The physiologic effects of nicotine are well known. NAC amide or a derivative thereof may cause vasodilation and improve cerebral blood flow, thereby resulting in a synergistic cerebral function-enhancing effect.

In mammals, the levels of glutathione in the plasma are relatively low, in the micromolar range, while intracellular levels are typically in the millimolar range. Therefore, intracellular cytosol proteins are subjected to vastly higher concentrations of glutathione than extracellular proteins. The endoplasmic reticulum, a cellular organelle, is involved in processing proteins for export from the cell. It has been found that the endoplasmic reticulum forms a separate cellular compartment from the cytosol, having a relatively oxidized state as compared to the cytosol, and thereby promoting the formation of disulfide links in proteins, which are often necessary for normal activity. In a number of pathological states, cells may be induced to produce proteins for export from the cells, and the progression of the pathology is interrupted by interference with the production and export of these proteins. For example, many viral infections rely on cellular production of viral proteins for infectivity. The interruption of the production of these proteins will interfere with infectivity Likewise, certain conditions involve specific cell-surface receptors, which must be present and functional. In both cases, cells that are induced to produce these proteins will deplete reduced glutathione in the endoplasmic reticulum. It is noted that cells that consume glutathione will tend to absorb glutathione from the plasma, and may be limited by the amounts present. Therefore, by increasing plasma glutathione levels, even transiently, the reducing conditions in the endoplasmic reticulum may be interfered with, and the protein production blocked. Normal cells may also be subjected to some interference; however, in viral infected cells, or cells otherwise abnormally stimulated, the normal regulatory mechanisms may not be intact, and the redox conditions in the endoplasmic reticulum will not be controlled by the availability of extracellular glutathione. The administration of NAC amide or its derivatives may serve to replenish GSH or the effects of GSH and provide significant effects for such conditions.

Reproduction of herpes viruses, which are DNA viruses, is inhibited or reduced in cell culture by the administration of extracellular glutathione. Examples of DNA viruses include Herpes Simplex Virus I, Herpes Simplex Virus II, Herpes zoster, cytomegalovirus, Epstein Barr virus and others. Therefore, according to the present invention, DNA virus and herpes virus infections may be treated by administering NAC amide or a derivative thereof. In addition, infection by the rabies virus, an RNA virus, may be treated by the administration of glutathione. While standard treatments are available, and indeed effective when timely administered, glutathione may be useful in certain circumstances. Therefore, rabies virus infection may be treated, at least in part, by administering NAC amide or a derivative thereof according to the present invention. One available treatment for rabies is an immune serum. The present invention encompasses the parenteral administration of NAC amide, or derivative thereof separately, or in combination with one or more immunoglobulins.

Coronary heart disease risk is increased by the consumption of a high-fat diet and is reduced by the intake of antioxidant vitamins, including vitamin E and vitamin C, as well as flavonoids. High fat meals impair the endothelial function through oxidative stress, resulting in impaired nitric oxide availability. It has been found that vitamin C and vitamin E restore the vasoconstriction resulting from nitric oxide production by endothelium after a high fat meal. According to the present invention, NAC amide or a derivative thereof may be administered prophylactically to combat vascular disease.

There are known to be qualitative differences among several species of free radicals. Accordingly, their rates of formation will differ, as will the different types of inciting agents that may have to be simultaneously controlled. For example, for those with macular degeneration, continued, unprotected exposure of the eyes to strong sunlight and to tobacco smoke would limit the benefits from an antioxidant used as a therapeutic agent for control of this disease. Therefore, one aspect of the invention provides synergistic therapies to patients by increasing antioxidant levels systemically or in specific organs as well as reducing oxidative, free radical generating and ionizing influences. In this case, NAC amide therapy would be complemented with ultraviolet blocking sunglasses, and a tobacco smoking cessation plan, as necessary. NAC amide or a derivative thereof can be used in combination with alpha tocopherol succinate, if necessary. Free radicals occur in different parts or subparts of tissues and cells, with different inciting agents. For example, in trauma to the brain or spinal cord, the injurious free radicals are in the fatty (lipid) coverings that insulate nerve fibers, i.e., the myelin sheaths. Extremely high doses of a synthetic cortico steroid, 5 to 10 grams of methyl prednisolone sodium succinate (MPSS), given for just 24 hours, rapidly reach the brain and spinal cord and diffuse rapidly into the myelin, neutralizing the trauma-induced radicals. The present invention therefore provides a pharmaceutical composition comprising a combination of NAC amide or a NAC amide derivative and a glucocorticoid agent.

According to the present invention, orally administered NAC amide or a derivative thereof can raise cell levels of glutathione to inhibit a number of pathologic processes. For example, NAC amide can be used to curtail the virtually self-perpetuating, powerful biochemical cycles producing corrosive free radicals and toxic cytokines that are largely responsible for the signs and symptoms of AIDS. These biochemical cycles destroy considerable quantities of glutathione but they can eventually be brought under control, and normalized with sufficient, ongoing NAC amide therapy. A typical example is the over production of a substance, 15 HPETE (15-hydroperoxy eicosatetraenoic acid), from activated macrophages. 15 HPETE is a destructive, immunosuppressing substance and requires glutathione for conversion into a non-destructive, benign molecule. The problem is that once macrophages are activated, they are difficult to normalize. Once inside cells, GSH curtails the production of free radicals and cytokines, corrects the dysfunctions of lymphoctyes and of macrophages, reinforces defender cells in the lungs and other organs and halts HIV replication in all major infected cell types, by preventing the activation of the viral DNA by precluding the activation of NF-κB, inhibiting the TAT gene product of HIV that drives viral replication and dismantling the gp120 proteins of the virus coat. NAC amide can be provided to disrupt the gp120 protein, thereby offering a potential mode of preventing transmission of virus not only to other cells in the patient, but perhaps to others.

Besides classic antiviral or antiretroviral agents (reverse transcriptase inhibitors, protease inhibitors), a number of other therapies may be of benefit for AIDS patients, and the present invention provides combinations of NAC amide or a derivative thereof with the following drugs: cycloporin A, thalidomide, pentoxifylline, selenium, desferroxamine, 2L-oxothiazolidine, 2L-oxothiazolidine-4-carboxylate, diethyldithiocarbamate (DDTC), BHA, nordihydroguairetic acid (NDGA), glucarate, EDTA, R-PIA, alpha-lipoic acid, quercetin, tannic acid, 2'-hydroxychalcone, 2-hydroxychalcone, flavones, alpha-angelicalactone, fraxetin, curcurmin, probucol, and arcanut (*areca catechu*).

Inflammatory responses are accompanied by large oxidative bursts, resulting in large numbers of free radicals. Therefore, NAC amide and its derivatives may have application in the therapy for inflammatory diseases. NAC amide or a derivative thereof may advantageously reduce the primary insult, as well as undesired aspects of the secondary response. According to the present invention, NAC amide or a derivative thereof may be administered to patients suffering from an inflammatory disease, such as arthritis of various types, inflammatory bowel disease, etc. The present invention also provides combination pharmaceutical therapy including NAC amide or NAC amide derivative and an analgesic or anti-inflammatory agent, for example, opiate agonists, glucocorticoids or non-steroidal anti-inflammatory drugs (NSAIDS), including opium narcotics, meperidine, propoxyphene, nalbuphine, pentazocine, buprenorphine, aspirin, indomethacin, diflunisal, acetominophen, ibuprofen, naproxen, fenoprofen, piroxicam, sulindac, tolmetin, meclofenamate, zomepirac, penicillamine, phenylbutazone, oxyphenbutazone, chloroquine, hydroxychloroquine, azathiaprine, cyclophosphamide, levamisole, prednisone, prednisolone, betamethasone, triamcinolone, and methylprednisolone. NAC amide and its derivatives may also be beneficial for the treatment of parotitis, cervical dysplasia, Alzheimer's disease, Parkinson's disease, aminoquinoline toxicity, gentamycin toxicity, puromycin toxicity, aminoglycoside nephrotoxicity, paracetamol, acetaminophen and phenacetin toxicity.

NAC amide or a derivative thereof may be added to a virus-contaminated fluid or potentially contaminated fluid to inactivate the virus. This occurs, for example, by reduction of critical viral proteins. According to an embodiment, NAC amide or a derivative thereof is added to blood or blood components prior to transfusion. The added NAC amide or derivative of NAC amide is added in a concentration of between about 100 micromolar to about 500 millimolar or to a solubility limit, whichever is lower, and more preferably in a concentration of about 10-50 millimolar. Additionally, the addition of NAC amide or a derivative thereof to whole blood, packed red blood cells, or other formed blood components (white blood cells, platelets) may be used to increase the shelf like and/or quality of the cells or formed components.

In another embodiment, the present invention encompasses the use of NAC amide, or derivative thereof or a pharmaceutically acceptable salt or ester thereof, in the treatment and/or prevention of cosmetic conditions and dermatological disorders of the skin, hair, nails, and mucosal surfaces when applied topically. In accordance with the invention, compositions for topical administration are provided that include (a) NAC amide, or derivative thereof or a suitable salt or ester thereof, or a physiologically acceptable composition containing NAC amide; and (b) a topically acceptable vehicle or carrier. The present invention also provides a method for the treatment and/or prevention of cosmetic conditions and/or dermatological disorders that entails topical administration of NAC amide- or NAC amide-derivative containing compositions to an affected area of a patient. Such compositions and methods are useful in anti-aging treatments and therapies, as well as for the treatment of wrinkles, facial lines and depressions, particularly around the eyes and mouth, creases in the skin, age spots and discolorations, and the like.

In another embodiment, the present invention provides methods and compositions useful for cancer and pre-cancer therapy utilizing NAC amide, or derivative thereof or its pharmaceutically acceptable salts or esters. The present invention particularly relates to methods and compositions comprising NAC amide or a derivative thereof in which apoptosis is selectively induced in cells of cancers or precancers. In another embodiment, the present invention relates to a method of selectively inducing apoptosis of precancer cells by administering an effective amount of NAC amide or a derivative thereof to a subject. In this embodiment, NAC amide or a derivative thereof can be topically administered to the subject. In another embodiment, the present invention relates to a method of selectively inducing apoptosis in cancer cells by administering an effective amount of NAC amide or a derivative thereof to a subject. NAC amide or its derivative can be topically administered to the subject in this embodiment. Selective apoptosis refers to a situation in which corresponding normal, non-transformed cells do not undergo NAC amide-induced cell death. In yet another embodiment, the present invention relates to a method comprising reducing the number of cancer cells present in a subject by administering NAC amide or a derivative thereof to the subject as an adjunct to chemotherapy or radiation therapies such that the susceptibility of the cancer cells to apoptosis is enhanced relative to the non-cancer cells of the subject. In a further embodiment, the present invention relates to a method comprising administering an effective amount of NAC amide or a derivative thereof as an adjunct to p53 therapy, including p53 gene therapy. The cancer or precancer cells in which apoptosis is induced are generally those which exhibit at least one functional p53 allele. In certain instances, administration of NAC amide results in restoration of mutant p53 protein conformation and/or activity to a functional state. It is to be understood that an endogenous functional p53 allele is not necessary for methods comprising p53 therapy, including p53 gene therapy.

In another embodiment of the invention, methods are provided which comprise administering NAC amide or a derivative thereof to selectively induce cells which arise in hyperproliferative or benign dysproliferative disorders. Another embodiment of the present invention encompasses the use of NAC amide or a derivative thereof in methods for selective cell cycle arrest comprising contacting the cell with an amount of NAC amide or a derivative thereof to selectively arrest cells at a particular stage of the cell cycle. For example, administration of NAC amide can lead to prolonged transition through G1 phase. This cell cycle arrest may be influenced by an increase in p21 expression. The methods of the present invention can also be utilized to reduce or inhibit tumor vascularization, or to induce differentiation in cancer cells.

In another of its aspects, the present invention is directed to the use of NAC amide or a derivative thereof to treat cancers and tumors that may be induced by faulty signals from the microenvironment that result in loss of tissue organization in cancerous organs and loss of genomic stability in individual cancer cells. Loss of tissue structure may lead to certain cancers. Involved in this process are matrix metalloproteinases (MMPs), which are enzymes that are important not only during an organism's development and during wound healing, but also in promoting tumorigenesis or carcinogenesis. In particular, MMPs contribute prominently to microenvironmental signals because these proteolytic enzymes degrade structural components of the basement membrane and extracellular matrix (ECM) and digest the contacts that bind epithelial cells into sheets, thereby permitting the invasion of tumor cells and metastasis. MMPs can also release cell-bound inactive precursor forms of growth factors; degrade cell-cell and cell-ECM adhesion molecules; activate precursor zymogen forms of other MMPs; and inactivate inhibitors of MMPs and other proteases. Further, these enzymes induce the epithelial-mesenchymal transition, or EMT, a transition of one cell state to another that causes epithelial cells to disassociate from their neighbors, break free and acquire the ability to move through the body. While this process is essential for normal development in the embryo, in cancers, such as breast cancer, EMT provides mobility for tumor cells and assists tumor cells in penetrating barriers, such as wall of lymph and blood vessels, thus facilitating metastasis.

MMP-3 is a particular type of metalloproteinase that has been observed to induce transformation in mammary epithelial cells in culture and in transgenic mice. MMP-3 has been found to cause normal cells to express the Rac1b protein, an unusual form of Rho GTPase that has previously been found only in cancers. Rac1b dramatically alters the cell skeleton, which facilitates the separation and movement of epithelial cells from surrounding cells. (D. C. Radisky et al., 2005, Nature, 436:123-127). Changes in the cell skeleton induced by Rac1b stimulate the production of highly reactive oxygen molecules, called reactive oxygen species (ROS), which can promote cancer by leading to tissue disorganization and by damaging genomic DNA. The increased amounts of ROS induced by Rac1b activate major genes that control the EMT, which then begins a cascade of massive tissue disorganization and stimulates the development of cancer by directly affecting genomic DNA, for example, causing deletion or duplication of large regions of the DNA. By altering the tissue structure, MMPs can also activate oncogenes and comprising the integrity of the DNA in an organism's genome.

For treating cancers, e.g., breast cancer, especially those involving the above-described mechanisms leading to abnormal cell structure and function and loss of tissue integrity, NAC amide in accordance with the present invention can be used to block the effects of ROS. This can be achieved, for example, by administering or introducing NAC amide or a derivative thereof to cells, tissues, and/or the body of a subject in need thereof, to affect or target molecules in the pathways leading to epithelial-mesenchymal transition. Accordingly, NAC amide or a derivative thereof can be used to inhibit MMP-3 and its functions, such as MMP-3-induced downregulation of epithelial cytokeratins and upregulation of mesenchymal vimentin, as well as MMP3-induced cell motility, invasion and morphological alterations. NAC amide or a derivative thereof can also be used to target ROS indirectly or directly, and/or the processes by which ROS activate genes that induce the EMT.

In another embodiment, the present invention encompasses compositions and methods comprising NAC amide or a derivative thereof for the suppression of allograft rejection in recipients of allografts.

In another embodiment, the present invention provides a NAC amide or derivative of NAC amide in a method of supporting or nurturing the growth of stem cells for stem cell transplants, particularly stem cells cultured in vitro prior to introduction into a recipient animal, including humans.

In another embodiment, the present invention provides methods of inhibiting, preventing, treating, or both preventing and treating, central nervous system (CNS) injury or disease, neurotoxicity or memory deficit in a subject, involving the administration of a therapeutically effective amount of NAC amide, or derivative thereof or a pharmaceutically acceptable composition thereof. Examples of CNS injuries or disease include traumatic brain injury (TBI), posttraumatic epilepsy (PTE), stroke, cerebral ischemia, neurodegenerative diseases of the brain such as Parkinson's disease, Dementia Pugilistica, Huntington's disease, Alzheimer's disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, and other CNS traumas. In other related embodiments, the present invention embraces a method of treating a subject suffering from a CNS injury or disease comprising administering to the subject a composition comprising a therapeutically effective amount of NAC amide or a derivative thereof. In another embodiment, the present invention relates to a method of preventing or inhibiting a CNS injury or disease in a subject comprising administering to the subject a composition comprising a therapeutically effective amount of NAC amide or a derivative thereof. In other embodiments, the present invention embraces a method of preventing, inhibiting or treating neurotoxicity or memory deficit in a subject comprising administering to the subject a composition comprising a therapeutically effective amount of NAC amide or a derivative thereof. Where the memory deficit may be induced by electroconvulsive shock therapy for treating diseases and disorders such as depression and schizophrenia, the composition may be administered before the electroconvulsive shock therapy to mitigate memory loss. In related embodiments, the CNS injury or disease may be traumatic brain injury (TBI), posttraumatic epilepsy (PTE), stroke, cerebral ischemia, or a neurodegenerative disease. In related embodiments, CNS injury may be induced by fluid percussion, by trauma imparted by a blunt object, for example on the head of the subject, by trauma imparted by an object which penetrates the head of the subject, by exposure to radiation, ionizing or iron plasma, a nerve agent, cyanide, toxic concentrations of oxygen, CNS malaria, or an anti-malaria agent. In the embodiments of the present invention, the therapeutically effective amount of NAC amide or a derivative thereof administered to the subject is the amount required to obtain the appropriate therapeutic effect, for example, about 0.001 mg to about 20 mg per kg of the subject, preferably about 1 mg to about 10 mg per kg of the subject, more preferably about 3 mg to about 10 mg per kg of the subject. In additional embodiments, the total daily amount of NAC amide or a derivative thereof administered to the subject is about 50 mg to about 1200 mg, or about 100 mg to about 1000 mg, or about 200 mg to about 800 mg, or about 300 mg to about 600 mg.

In other embodiments, the invention encompasses a method of treating a subject (e.g., an animal, including humans) before the subject is exposed or likely to be exposed to a risk of CNS injury or damage, or before the subject is exposed to conditions likely to cause neurotoxicity or memory deficit or both, by administering NAC amide or a derivative thereof to a subject in a period of time prior to the exposure of the subject to the risk of CNS injury or damage, etc. Illustratively, conditions that may cause CNS injury or damage, neurotoxicity or memory deficit include electroconvulsive shock therapy, traumatic brain injury (TBI), posttraumatic epilepsy (PTE), stroke, cerebral ischemia, neurodegenerative diseases, fluid percussion, a blunt object impacting the head of the subject, an object penetrating the head of the subject, radiation, ionizing or iron plasma, nerve agents, cyanide, toxic concentrations of oxygen, CNS malaria, and anti-malaria agents. Other conditions that may cause CNS injury or damage, neurotoxicity or memory deficit include, without limitation, certain medical procedures or conditions associated with risk for CNS ischemia, hypoxia or embolism such as brain tumor, brain surgery, other brain-related disorders, open heart surgery, carotid endarterectomy, repair of aortic aneurysm, atrial fibrillation, cardiac arrest, cardiac or other catheterization, phlebitis, thrombosis, prolonged bed rest, prolonged stasis (such as during space travel or long trips via airplane, rail, car or other transportation), CNS injury secondary to air/gas embolism or decompression sickness. The period of time may be about 72 hours prior to the time of expected exposure, or about 48 hours prior to the time of expected exposure, or about 12 hours prior to the time of expected exposure, or about 4 hours prior to the time of expected exposure, or about 30 minutes-2 hours prior to the time of expected exposure. The administration of NAC amide may be continuous from the initial time of treatment to the end of treatment. For example, a transdermal patch or a slow-release formulation may be used to continually administer NAC amide or a derivative thereof to the subject for a given period of time. Alternatively, NAC amide or a derivative thereof may be administered to the subject periodically. For example, NAC amide or a derivative thereof may first be administered at about 24 hours before the time of expected exposure and then administered at about every 2 hours thereafter. For these embodiments of the invention, the NAC amide- or NAC amide derivative-containing composition may further comprise a pharmaceutically acceptable excipient and the composition may be administered intravenously, intradermally, subcutaneously, orally, transdermally, transmucosally or rectally.

In other embodiments, the present invention encompasses a pharmaceutical composition for treating or preventing CNS injury, disease or neurotoxicity in a subject comprising a therapeutically effective amount of NAC amide or a derivative thereof and a pharmaceutically acceptable excipient. In a further embodiment, the invention embraces a kit comprising a composition comprising a therapeutically effective amount of NAC amide or a derivative thereof. The kit may further comprise a device for administering the composition to a subject such as an injection needle, an inhaler, a transdermal patch, as well as instructions for use.

In another embodiment of the present invention, anti-cancer treatments involving NAC amide or a derivative thereof are designed to specifically target cancer and tumor cells. This embodiment is directed to the use of nano-sized particles for the in vivo and ex vivo administration of NAC amide or a derivative thereof to cancer and tumor cells. According to this embodiment, cancer cells, which display more receptors for the vitamin folic acid (or folate) and absorb more folic acid than do normal, healthy cells, are able to be preferentially targeted. To this end, core or shell nanogels, or nanoparticles, can be functionalized with folic acid or folate conjugated or linked to NAC amide or a derivative thereof without disrupting or destroying the folic acid binding site to its cell receptor. Such functionalized nanoparticles can be introduced into a subject, particularly a folate-deprived subject, with a cancer, e.g., epithelial cancer, in whom the cancer cells have excess folic acid receptors which will preferentially bind the folic acid-NAC amide (or folic acid-NAC amide derivative) nanoparticles and endocytose them. Once inside the cancer cell, NAC amide or a derivative thereof exert its therapeutic effects, for example, by inhibiting ROS and/or other target molecules that play a role in initiating, fueling, and/or maintaining cancer cells, and/or ultimately killing the cancer cells.

Illustratively, PAMAM dendritic polymers <5 nm in diameter can be used as carriers of NAC amide, as described in J. F. Kukowska-Latallo et al., 2005, Cancer Res., June 15; 65(12):5317-24, to target folic acid receptor-expressing (overexpressing) tumor and cancer cells. Acetylated dendrimers can be conjugated to folic acid as a targeting agent and then coupled to NAC amide or a derivative thereof and either fluorescein or 6-carboxytetramethylrhodamine. Alternatively, NAC amide or a derivative thereof can be coupled to folic acid to form a conjugate and the conjugate can be coupled to the nanoparticles. These conjugates can be injected i.v. into a tumor-bearing patient or mammal, especially those tumors that overexpress the folic acid receptor. The folate-conjugated nanoparticles can then concentrate in the tumor and tissue following administration, where the delivered NAC amide or NAC derivative can interact with ROS in the cells, and/or target other molecules to kill the cancer or tumor cells. The tumor tissue localization of the folate-targeted polymer may be attenuated by prior i.v. injection of free folic acid.

In a similar embodiment, polymers or nanoparticles can be functionalized to display glutathione-NAC amide or glutathione-NAC amide derivative conjugates, which can then be used to deliver NAC amide or a derivative thereof to cancer cells which display increased numbers of glutathione receptors on their cell surfaces. The NAC amide-glutathione nanoparticles can then be targeted to those cancer cells having glutathione receptors and preferentially endocytosed by the cells. In these embodiments, the present invention provides directed delivery of NAC amide or a derivative thereof to cells, such as cancer cells that express high levels of receptors for folic acid (folate) or glutathione. In accordance with these embodiments, NAC amide ("NACA") or a derivative thereof is coupled to a ligand for a cell surface receptor (e.g., folic acid or glutathione) to form a conjugate. This NACA-ligand conjugate is coated or adsorbed onto readily injectable nanoparticles using procedures known to those skilled in the art.

Accordingly, the nanoparticles containing NAC amide or a derivative thereof ("nano-NACA particles") may be preferentially taken up by cancer or tumor cells where the NAC amide will exert its desired effects.

In an embodiment, the present invention is drawn to a method of directed delivery of NAC amide or a derivative thereof to host cells expressing high levels of surface receptor for a ligand, comprising: a) conjugating acetylated dendritic nanopolymers to ligand; b) coupling the conjugated ligand of step (a) to NAC amide or a derivative thereof to form NAC amide-ligand nanoparticles; and c) injecting the nanoparticles of (b) into the host. In another embodiment, the present invention is drawn to a method of directed delivery of NAC amide or a derivative thereof to host cells expressing high levels of surface receptor for a ligand, comprising: a) coupling NAC amide or a derivative thereof to the surface receptor ligand to form a NAC amide-ligand conjugate; b) adsorbing the NAC amide-ligand conjugate onto nanoparticles; and c) injecting the nanoparticles of (b) into the host.

Another embodiment of the present invention provides a compound of the formula I:

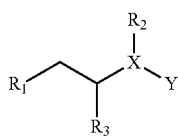

I wherein: $R_1$ is OH, SH, or S—S—Z; X is C or N; Y is $NH_2$, OH, $CH_3$—C=O, or NH—$CH_3$; $R_2$ is absent, H, or =O $R_3$ is absent or

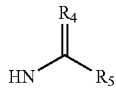

wherein: $R_4$ is NH or O; $R_5$ is $CF_3$, $NH_2$, or $CH_3$ and wherein: Z is

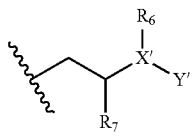

with the proviso that if $R_1$ is S—S—Z, X and X' are the same, Y and Y' are the same, $R_2$ and $R_6$ are the same, and $R_3$ and $R_7$ are the same.

In one embodiment, $R_1$ is S, X is C, Y is NH—$CH_3$, $R_2$ is H, $R_3$ is

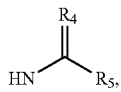

$R_4$ is O, and $R_5$ is $CH_3$. In another embodiment, $R_1$ is S, X is N, Y is $CH_3$—C=O, $R_2$ is H, and $R_3$ is absent.

The present invention also provides compounds of the formula I above, wherein $R_1$ is S, X is C, Y is $NH_2$, $R_2$ is =O, $R_3$ is

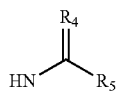

$R_4$ is O, and $R_5$ is $CF_3$. Compounds of the present invention also include compounds of formula I wherein $R_1$ is O, X is C, Y is $NH_2$, $R_2$ is =O, $R_3$ is

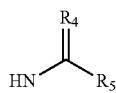

$R_4$ is O, and $R_5$ is $CH_3$. Also provided by the present invention are compounds of formula I wherein $R_1$ is S, X is C, Y is OH, $R_2$ is absent, $R_3$ is

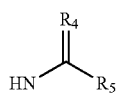

$R_4$ is O, and $R_5$ is $CH_3$, or wherein $R_1$ is S, X is C, Y is $NH_2$, $R_2$ is =O, $R_3$ is

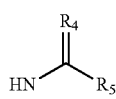

$R_4$ is NH, and $R_5$ is $NH_2$. Another embodiment of the present invention provides compounds of formula I wherein $R_1$ is O, X is C, Y is OH, $R_2$ is absent, $R_3$ is

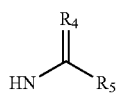

$R_4$ is O, and $R_5$ is $CH_3$; or wherein $R_1$ is S, X is C, Y is $NH_2$, $R_2$ is =O, $R_3$ is

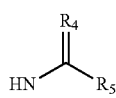

$R_4$ is O, and $R_5$ is $CH_3$. In a further embodiment, the present invention provides compounds of formula I wherein $R_1$ is S—S—Z, X is C, Y is $NH_2$, $R_2$ is =O, $R_3$ is

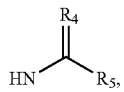

$R_4$ is O and $R_5$ is $CH_3$.

The compounds disclosed herein can be chiral, i.e., enantiomers, such as L- and D-isomers, or can be racemic mixtures of D- and L-isomers. Preferred compounds include, but are not limited to, the following:

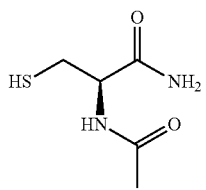
I
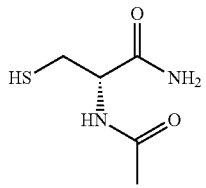
II
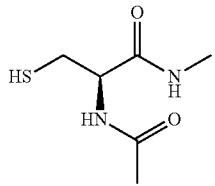
III
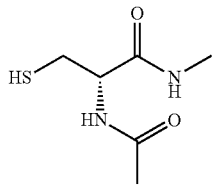
IV
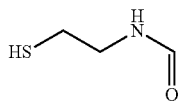
V
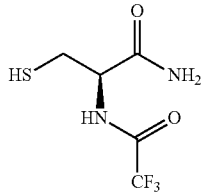
VI
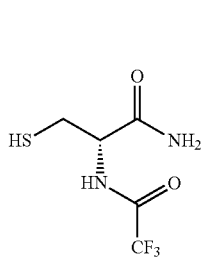
VII
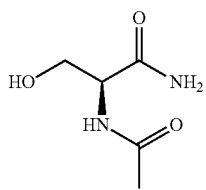
VIII
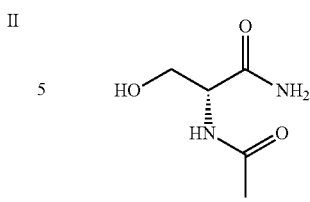
IX
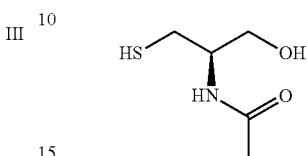
X
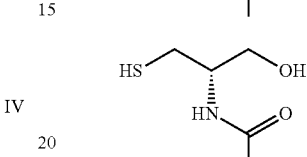
XI
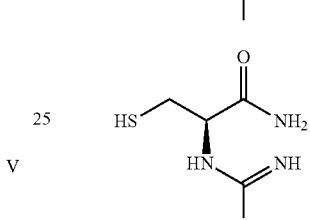
XII
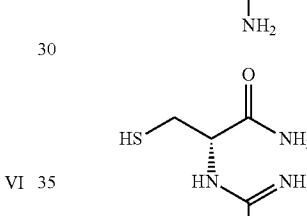
XIII
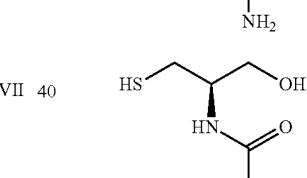
XIV
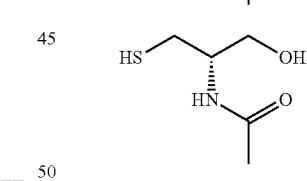
XV
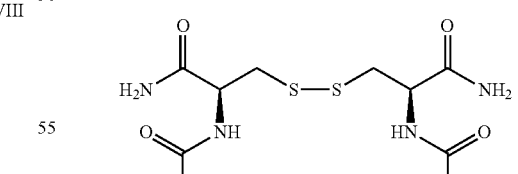
XVI
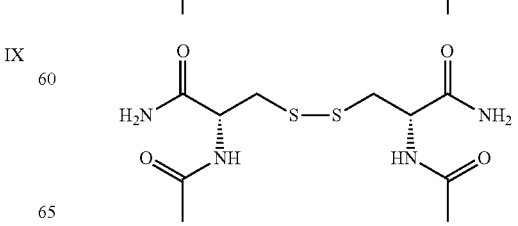
XVII
XVIII In one embodiment, Compounds I through XVIII comprise NAC amide or NAC amide derivatives.

In another embodiment, a process for preparing an L- or D-isomer of the compounds of the present invention are provided, comprising adding a base to L- or D-cystine diamide dihydrochloride to produce a first mixture, and subsequently heating the first mixture under vacuum; adding a methanolic solution to the heated first mixture; acidifying the mixture with alcoholic hydrogen chloride to obtain a first residue; dissolving the first residue in a first solution comprising methanol saturated with ammonia; adding a second solution to the dissolved first residue to produce a second mixture; precipitating and washing the second mixture; filtering and drying the second mixture to obtain a second residue; mixing the second residue with liquid ammonia, and an ethanolic solution of ammonium chloride to produce a third mixture; and filtering and drying the third mixture, thereby preparing the L- or D-isomer compound.

The base can comprise liquid ammonia or methylamine. The second solution comprises water, an acetate salt, and an anhydride, wherein the acetate salt can comprise sodium acetate or sodium trifluoroacetate, and the anhydride can comprise acetic anhydride or trifluoroacetic anhydride. Alternatively, the second solution can comprise dichloromethane, triethylamine, and 1,3-bis(benzyloxycarbonyl)-2-methyl-2-thiopseudourea. In addition to liquid ammonia and an ethanolic solution of ammonium chloride, the second residue can be further mixed with sodium metal.

In some embodiments, the process further comprises dissolving the L- or D-isomer compound in ether; adding to the dissolved L- or D-isomer compound an ethereal solution of lithium aluminum hydride, ethyl acetate, and water to produce a fourth mixture; and filtering and drying the fourth mixture, thereby preparing the L- or D-isomer compound.

The compounds of formula II and III are prepared by mixing L- or D-cystine diamide dihydrochloride with liquid ammonia; warming the mixture to remove volatiles; warming mixture in vacuo to 50° C.; adding a warm methanolic solution; filtering the solution; acidifying the filtrate with alcoholic hydrogen chloride for obtaining a first residue, dissolving the first residue in a solution of methanol saturated with ammonia; concentrating to dryness; adding water, sodium acetate and acetic anhydride; raising the temperature to 50° C.; precipitating the mixture and washing the mixture with water; filtering the crude solid; drying the mixture for obtaining a second residue, mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula IV and V are prepared by mixing L- or D-cystine diamide dihydrochloride with methylamine; warming the mixture to remove volatiles; warming mixture in vacuo to 50° C.; adding a warm methanolic solution; filtering the solution; acidifying the filtrate with alcoholic hydrogen chloride for obtaining a first residue, dissolving the first residue in a solution of methanol saturated with ammonia; concentrating to dryness; adding water, sodium acetate and acetic anhydride; raising the temperature to 50° C.; precipitating the mixture and washing the mixture with water; filtering the crude solid; drying the mixture for obtaining a second residue, mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula VII and VIII are prepared by mixing L- or D-cystine diamide dihydrochloride with ammonia; warming the mixture to remove volatiles; warming mixture in vacuo to 50° C.; adding a warm methanolic solution; filtering the solution; acidifying the filtrate with alcoholic hydrogen chloride for obtaining a first residue, dissolving the first residue in a solution of methanol saturated with ammonia; concentrating to dryness; adding water, sodium trifluoroacetate and trifluoroacetic anhydride; raising the temperature to 50° C.; precipitating the mixture and washing the mixture with water; filtering the crude solid; drying the mixture for obtaining a second residue, mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula XIII and XIV are prepared by mixing L- or D-cystine diamide dihydrochloride with ammonia; warming the mixture to remove volatiles; warming mixture in vacuo to 50° C.; adding a warm methanolic solution; filtering the solution; acidifying the filtrate with alcoholic hydrogen chloride for obtaining a first residue, dissolving the first residue in a solution of methanol saturated with ammonia; concentrating to dryness; adding dichloromethane, triethylamine, and 1,3-bis(benzyloxycarbonyl)-2-methyl-2-thiopseudourea; lowering the temperature to 0° C.; precipitating the mixture and washing the mixture with water; filtering the crude solid; drying the mixture for obtaining a second residue, mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula XI and XII are prepared by mixing L- or D-cystine diamide dihydrochloride with liquid ammonia; warming the mixture to remove volatiles; warming mixture in vacuo to 50° C.; adding a warm methanolic solution; filtering the solution; acidifying the filtrate with alcoholic hydrogen chloride for obtaining a first residue; dissolving the first residue in a solution of methanol saturated with ammonia; concentrating to dryness; adding water, sodium acetate and acetic anhydride; raising the temperature to 50° C.; precipitating the mixture; washing the mixture with water; filtering the crude solid; drying the mixture for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; dissolving the third residue in ether; slowly adding an ethereal solution of lithium aluminum hydride; slowly adding ethyl acetate; slowly adding water; filtering and separating the inorganic salts; concentrating and cooling the filtrate to obtain a fourth residue; and crystallizing the fourth residue from isopropanol.

The compounds of formula XVII and XVIII are prepared by mixing L- or D-cystine diamide dihydrochloride with liquid ammonia; warming the mixture to remove volatiles; warming mixture in vacuo to 50° C.; adding a warm methanolic solution; filtering the solution; acidifying the filtrate with alcoholic hydrogen chloride for obtaining a first residue; dissolving the first residue in a solution of methanol saturated with ammonia; concentrating to dryness; adding of water, sodium acetate and acetic anhydride; raising the temperature to 50° C.; precipitation of the mixture; washing the mixture with water; filtering the crude solid; drying the mixture for obtaining a second residue; and crystallizing the second residue from isopropanol.

Another embodiment of the invention provides a process for preparing an L- or D-isomer of the compounds disclosed herein, comprising mixing S-benzyl-L- or D-cysteine methyl ester hydrochloride or O-benzyl-L- or D-serine methyl ester hydrochloride with a base to produce a first mixture; adding ether to the first mixture; filtering and concentrating the first mixture; repeating steps (c) and (d), to obtain a first residue; adding ethyl acetate and a first solution to the first residue to produce a second mixture; filtering and drying the second mixture to produce a second residue; mixing the second residue with liquid ammonia, sodium metal, and an ethanolic solution of ammonium chloride to produce a third mixture; and filtering and drying the third mixture, thereby preparing the L- or D-isomer compound.

The base can comprise liquid ammonia or methylamine. The second solution comprises water, an acetate salt, and an anhydride, wherein the acetate salt can comprise sodium acetate or sodium trifluoroacetate, and the anhydride can comprise acetic anhydride or trifluoroacetic anhydride. Alternatively, the second solution can comprise dichloromethane, triethylamine, and 1,3-bis(benzyloxycarbonyl)-2-methyl-2-thiopseudourea.

In some embodiments, the process further comprises dissolving the L- or D-isomer compound in ether; adding to the dissolved L- or D-isomer compound an ethereal solution of lithium aluminum hydride, ethyl acetate, and water to produce a fourth mixture; and filtering and drying the fourth mixture, thereby preparing the L- or D-isomer compound.

The compounds of formula II and III are prepared by mixing S-benzyl-L- or D-cysteine methyl ester hydrochloride with a cold methanolic solution of ammonia; passing a stream of ammonia over the mixture; sealing the flask securely; concentrating the mixture; adding ether; filtering the solution; concentrating the filtrate; adding ether and filtering again, to obtain a residue; suspending the residue with ethyl acetate; adding acetic anhydride to this suspension; adding water, sodium acetate and acetic anhydride; raising the temperature to 65° C.; cooling the mixture; filtering the crude solid; washing with ethyl acetate; drying the precipitate for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula IV and V are prepared by mixing S-benzyl-L- or D-cysteine methyl ester hydrochloride with a cold methanolic solution of methylamine; passing a stream of methylamine over the mixture; sealing the flask securely; concentrating the mixture; adding ether; filtering the solution; concentrating the filtrate; adding ether and filtering again, to obtain a residue; suspending the residue with ethyl acetate; adding acetic anhydride to this suspension; adding water, sodium acetate and acetic anhydride; raising the temperature to 65° C.; cooling the mixture; filtering the crude solid; washing with ethyl acetate; drying the precipitate for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula VII and VIII are prepared by mixing S-benzyl-L- or D-cysteine methyl ester hydrochloride with a cold methanolic solution of ammonia; passing a stream of methylamine over the mixture; sealing the flask securely; concentrating the mixture; adding ether; filtering the solution; concentrating the filtrate; adding ether and filtering again, to obtain a residue; suspending the residue with ethyl acetate; adding trifluoroacetic anhydride to this suspension; adding water, sodium trifluoroacetate and trifluoroacetic anhydride; raising the temperature to 65° C.; cooling the mixture; filtering the crude solid; washing with ethyl acetate; drying the precipitate for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula IX and X are prepared by mixing O-benzyl-L- or D-serine methyl ester hydrochloride with a cold methanolic solution of ammonia; passing a stream of methylamine over the mixture; sealing the flask securely; concentrating the mixture; adding ether; filtering the solution; concentrating the filtrate; adding ether and filtering again, to obtain a residue; suspending the residue with ethyl acetate; adding acetic anhydride to this suspension; adding water, sodium acetate and acetic anhydride; raising the temperature to 65° C.; cooling the mixture; filtering the crude solid; washing with ethyl acetate; drying the precipitate for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula XIII and XIV are prepared by mixing S-benzyl-L- or D-cysteine methyl ester hydrochloride with a cold methanolic solution of ammonia; passing a stream of ammonia over the mixture; sealing the flask securely; concentrating the mixture; adding ether; filtering the solution; concentrating the filtrate; adding ether and filtering again, to obtain a residue; suspending the residue with ethyl acetate; adding acetic anhydride to this suspension; adding dichloromethane, triethylamine, and 1,3-bis(benzyloxycarbonyl)-2-methyl-2-thiopseudourea; lowering the temperature to 0° C.; precipitating the mixture; washing the mixture with water; filtering the crude solid; drying the mixture for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

The compounds of formula XI and XII are prepared by (a) mixing S-benzyl-L- or D-cysteine methyl ester hydrochloride with a cold methanolic solution of ammonia; passing a stream of ammonia over the mixture; sealing the flask securely; concentrating the mixture; adding ether; filtering the solution; concentrating the filtrate; adding ether and filtering again, to obtain a residue; suspending the residue with ethyl acetate; adding acetic anhydride to this suspension; adding of water, sodium acetate and acetic anhydride; raising the temperature to 65° C.; cooling the mixture; filtering the crude solid; washing with ethyl acetate; drying the precipitate for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; dissolving the third residue in ether; slowly adding an ethereal solution of lithium aluminum hydride; slowly adding ethyl acetate; slowly adding water; filtering and separating the inorganic salts; concentrating and cooling the filtrate to obtain a fourth residue; and crystallizing the fourth residue from isopropanol.

The compounds of formula XV and XVI are prepared by (a) mixing O-benzyl-L- or D-serine methyl ester hydrochloride with a cold methanolic solution of ammonia; passing a stream of ammonia over the mixture; sealing the flask securely; concentrating the mixture; adding ether; filtering the solution; concentrating the filtrate; adding ether and filtering again, to obtain a residue; suspending the residue with ethyl acetate; adding acetic anhydride to this suspension; adding of water, sodium acetate and acetic anhydride; raising the temperature to 65° C.; cooling the mixture; filtering the crude solid; washing with ethyl acetate; drying the precipitate for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; dissolving the third residue in ether; slowly adding an ethereal solution of lithium aluminum hydride; slowly adding ethyl acetate; slowly adding water; filtering and separating the inorganic salts; concentrating and cooling the filtrate to obtain a fourth residue; and crystallizing the fourth residue from isopropanol.

Yet another embodiment of the invention provides a process for preparing a compound as disclosed herein, comprising mixing cystamine dihydrochloride with ammonia, water, sodium acetate, and acetic anhydride to produce a first mixture; allowing the first mixture to precipitate; filtering and drying the first mixture to produce a first residue; mixing the second residue with liquid ammonia, sodium metal, and an ethanolic solution of ammonium chloride to produce a second mixture; filtering and drying the second mixture, thereby preparing the compound.

The compound of formula VI is prepared by mixing cystamine dihydrochloride with ammonia; adding water, sodium acetate and acetic anhydride; raising the temperature to 50° C.; precipitating the mixture; washing the mixture with water; filtering the crude solid; drying the mixture for obtaining a second residue; mixing the second residue with liquid ammonia; slowly adding sodium metal; removal of the solvent; slowly adding an ethanolic solution of ammonium chloride; filtering and separating the inorganic salt; concentrating and cooling the filtrate to obtain a third residue; and crystallizing the third residue from isopropanol.

EXAMPLES

Example 1

In this Example, NAC amide was assessed for its protective effects against oxidative toxicity induced by glutamate in PC12 cells.

Materials and methods: N-(1-pyrenyl)-maleimide (NPM) was purchased from Aldrich (Milwaukee, Wis., USA). N-acetylcysteine amide was obtained from Novia Pharmaceuticals, (Israel). High-performance liquid chromatography (HPLC)-grade solvents were purchased from Fisher Scientific (Fair Lawn, N.J.). All other chemicals were purchased from Sigma (St. Louis, Mo., USA).

Cell culture and toxicity studies: Stock culture of PC12 cells, purchased from ATCC, were grown in 75 cm$^2$ tissue culture flasks in RPMI 1640, supplemented with 10% (v/v) heat-inactivated horse serum, and 5% (v/v) fetal bovine serum, to which 1% (v/v) penicillin and streptomycin were added. Cultures were maintained at 37° C. in a humidified atmosphere containing 5% $CO_2$. The cells were passaged twice a week. Unless specified, all of the experiments were performed using Dulbecco's modified Eagle's medium (DMEM) as differentiation medium, supplemented with 0.5% (v/v) fetal bovine serum, 1% (v/v) penicillin and streptomycin. PC12 cells were plated at a density of $25 \times 10^3$ cells/well in a 24-well, collagen-coated plate for morphological assessment. The plate was divided into five groups in triplicate: 1) control: no glutamate, no NAC amide; 2) Nerve Growth Factor (NGF) control: NGF (100 ng/ml), no glutamate, no NAC amide; 3) NAC amide only: NGF (100 ng/ml), no glutamate, NAC amide (750 µM); 4) glutamate only: NGF (100 ng/ml), glutamate (10 mM), no NAC amide; and 5) Glu+NAC amide: NGF (100 ng/ml), glutamate (10 mM), NAC amide (750 µM). All wells received 100 ng/ml NGF every other day, except Group I. After one week, cells were treated or not (control) with 10 mM glutamate, with or without NAC amide, for 24 hours. Twenty-four hours later, the cells were fixed with 0.5% (v/v) glutaraldehyde in PBS and micropictures were taken.

LDH assay: For the lactate dehydrogenase (LDH) assay, cells were plated at a density of $2.5 \times 10^5$ cells/well in a 24 well collagen-coated culture plate and, after 24 h; the medium was replaced with fresh DMEM medium containing the desired concentration of glutamate and NAC amide. After the desired incubation period, the LDH activity released was determined using the kit as described below. For the MTS assay, cells were plated at a density of $10^5$ cells/well in a 24 well collagen-coated plate. At the end of the experiments, cell viability was assayed using the kit as described. The LDH activity assay was performed with the CytoTox96® Non-Radioactive Cytotoxicity Assay kit (Promega, Madison, Wis., USA), which quantitatively measured the activity of LDH, a stable cytosolic enzyme that is released upon cell lysis [Technical Bulletin No. 163, Promega]. LDH in culture supernatants was measured with a 30-minute coupled enzymatic assay, which resulted in the conversion of a tetrazolium salt into a red formazan product. The amount of color formed was proportional to the degree of damage to the cell membranes. Absorbance data were collected using a BMG microplate reader (BMG Labtechnologies, Inc., Durham, N.C., USA) at 490 nm. LDH leakage was expressed as the percentage (%) of the maximum LDH release in the cells treated with glutamate alone (100%), according to the formula:

$$\% \ LDH \ released = \frac{Experimental \ LDH \ release}{Maximum \ LDH \ release} \times 100$$

MTS assay: The MTS assay (Cell Titer 96® Aqueous One solution cell proliferation Assay, Promega) is a cell proliferation assay in which the administered (3-(4,5-dimethyl thiazol-2-yl)-5-(3-carboxymethoxy phenyl)-2-(4-sulfophenyl)-2H-tetrazolium, inner salt, MTS) [21] is bioreduced by viable cells to a colored formazan product that is soluble in media. Absorbance at 490 nm is proportional to the number of living cells in the culture.

GSH measurement: Cellular levels of GSH were determined by using the method as described in Winters R. A. et al., Anal Biochem., 227(1):14-21, 1995. Cells were seeded at a density of 80,000 cells/cm$^2$ on poly-D-lysine coated (0.05 mg/ml) 75 cm$^2$ flasks (5 ml/flask) for GSH measurement.

After 24 hours, the flasks were incubated with fresh medium containing glutamate (10 mM), or BSO (0.2 mM) or Glu+ BSO+NAC amide (750 µM) at 370 C for another 24 h. After the incubation period, cells were removed from the cultures and homogenized in serine borate buffer (100 mM Tris-HCl, 10 mM boric acid, 5 mM L-serine, 1 mM DETAPAC, pH 7.4). Twenty (20) µl of the diluted cell homogenate were added to 230 µl of serine borate buffer and 750 µl of NPM (1 mM in acetonitrile). The resulting solutions were incubated at room temperature for 5 min. The reaction was stopped by the addition of 5 µl of 2N HCl. The samples were then filtered through a 0.2 µm Acrodisc filter and injected onto the HPLC system.

MDA measurement: To prepare the solution, 350 µl of straight cell homogenate, 100 µl of 500 ppm BHT (butylated hydroxytoluene), and 550 µl of 10% TCA (trichloroacetic acid) were combined and boiled for 30 min. The tubes were cooled on ice and centrifuged for 10 min at 2500 rpm. Five hundred (500) µl of the supernatant were removed and 500 µl of TBA (thiobarbituric acid) were added. The tubes were boiled again for 30 min, and then cooled on ice. From this solution, 500 µl were removed, added to 1.0 ml of n-butanol, vortexed, and centrifuged for 5 min at 60 g to facilitate a phase separation. The top layer was then filtered through 0.45 µm filters and injected onto a 5 µm C18 column (250.times.4.6 mm) on a reverse phase HPLC system. The mobile phase consisted of 69.4% 5 mM sodium phosphate buffer (pH=7.0), 30% acetonitrile, and 0.6% THF (tetrahydrofuran). The excitation wavelength was 515 nm; the emission wavelength was 550 nm (Draper H. H. et al., Free Radic Biol Med., 15(4): 353-63, 1993).

Protein determination and statistical analysis: Protein levels were determined by the Bradford method with Coomassie Blue (Bio-Rad) (Bradford M. M., Anal Biochem., 72:248-54, 1976). The data were given as the mean±SD. The one-way analysis of variance test was used to analyze the significance of the differences between the control and experimental groups.

This Example shows that NAC amide protects cells against glutamate toxicity. Glutamate toxicity was evaluated by 1) morphological assessment of PC12 cells in the presence of glutamate; 2) measuring the amount of LDH released in the media 24 h after glutamate exposure; and 3) measuring cell viability using the MTS assay. As shown in FIGS. 2A-D, cells completely lost the normal morphology of their neurites in the presence of 10 mM glutamate, as compared to the control cells. To determine whether NAC amide could protect the cells from glutamate toxicity, PC12 cells were exposed to 10 mM glutamate for 24 hours in the presence of 750 µM NAC amide, and cell viability was examined by light microscopy. The addition of NAC amide protected the PC12 cells from glutamate toxicity by slightly decreasing the bleb formation on neurites.

To quantify the protection provided by NAC amide, PC12 cells were exposed to 10 mM glutamate in the presence of NAC amide for 24 hours, and then the amount of LDH released was measured using the LDH assay. As shown in FIG. 3, inclusion of 750 µM NAC amide in the assay completely protected the cells from cell damage, even in the presence of 10 mM glutamate (the % LDH released was 28.9.+−.3.7%). Similar results were obtained when cells were exposed to 10 mM glutamate in the presence of NAC amide for 24 hours, and the cell viability was assessed by the MTS assay.

The results of Example 1 demonstrate that NAC amide treatment significantly increased PC12 cell GSH levels. When cells were exposed to 10 mM glutamate, a significant reduction in GSH levels was observed (Table 1).

TABLE 1

Effect of NAC amide on intracellular GSH levels in the presence of BSO and Glutamate

| Group | GSH Levels (nM/mg protein) |
| --- | --- |
| Control | 54 ± 13.4 |
| GLU (10 mM) * | 23 ± 4.2 |
| BSO (0.2 mM) | ND |
| NAC amide (750 µM) * | 112 ± 17.8 |
| GLU + NAC amide ** | 88 ± 11.0 |
| GLU + BSO + NAC amide *** | 30 ± 4.3 |

PC12 cells were seeded and grown for 24 hours, then they were treated with either GLU (10 mM); NAC amide (750 µM); GLU (10 mM)+NAC amide (750 µM); GLU (10 mM)+BSO (0.2 mM)+NAC amide (750 µM); or BSO (0.2 mM). Twenty hours later, cells were removed and analyzed for GSH levels, as described in the text. Values represent means.+−. SD. Statistically different values of *P<0.05 were determined, compared to control. P<0.001 compared to glutamate-treated group. *P<0.05 compared to glutamate-treated group. At a 750 µM concentration and 24 hour treatment time, NAC amide increased the PC12 cell GSH level two fold, compared to the control group. Interestingly, similar results were obtained when Chinese hamster ovary (CHO) cells were incubated with NAC amide (data not shown).

The intracellular levels of GSH were determined in PC12 cells incubated with 10 mM glutamate for 24 hours, and the effects of NAC amide were analyzed. Treatment of cells with NAC amide prevented the marked decline of cellular GSH levels that normally occurs after glutamate treatment (Table 1). Glutamate inhibits cystine uptake, resulting in the loss of cellular GSH, while buthionine-sulfoximine (BSO) inhibits γ-GCS activity and thereby causes the depletion of intracellular GSH. To determine whether the increase in intracellular GSH by NAC amide was γ-GCS-dependent, cells were treated with 0.2 mM BSO. The simultaneous treatment of glutamate and BSO, depleted the cell GSH to almost undetectable levels (Table 1). Interestingly, in GSH synthesis-arrested cells, NAC amide treatment was effective and maintained 56% of the cells' GSH levels. NAC amide further protected cells against intracellular peroxide accumulation. Malondialdehyde (MDA) is a by-product of a free radical attack on lipids. Marked increase in MDA levels was observed in glutamate-exposed cells, as compared with the corresponding control cells (Table 2). Treatment with NAC amide completely protected cells against glutamate toxicity by lowering MDA levels.

TABLE 2

Effects of NAC amide on MDA levels in Glutamate-exposed PC12 cells

| Group | MDA Levels (nM/100 mg protein) |
| --- | --- |
| Control | 54 ± 14 |
| GLU (10 mM) | 247 ± 26 |
| NAC amide (750 µM) | 81 ± 22 |
| GLU + NAC amide | 88 ± 11 |

Cells were plated and grown for 24 hours, and then they were exposed to glutamate (10 mM) in the presence or absence of NAC amide (750 µM). Twenty-four hours later, the cells were harvested and malondialdehyde levels were measured. Values represent means.+−.SD. Statistically different values of *P<0.002 and P<0.05 were determined, compared to control. *P<0.05 compared to glutamate-treated group.

In this Example, it was determined that a high concentration of glutamate-induced oxidative toxicity was characterized by various potentially detrimental changes in intracellular GSH levels, MDA levels, and LDH activity, resulting in a reduction of PC12 cell viability. Treatment with NAC amide increased intracellular GSH, and reduced MDA levels, thereby attenuating glutamate-induced cytotoxicity. Evaluation was done by LDH and MTS assay. Glutamate cytotoxicity has been attributed to either excitatory action through the activation of glutamate receptors or inhibition of cystine uptake that leads to the decreased GSH levels. Although PC12 cells express NMDA receptors, toxicity exhibited by glutamate does not solely relate to the presence of these receptors, as NMDA has no effect on PC12 cell death. The disruption of intracellular redox homeostasis by high concentrations of glutamate is thought to be a major contributing mechanism of cellular damage in vivo. Under conditions such as cerebral ischemia, extracellular glutamate levels increase 800%, as compared to control, which would decrease brain GSH levels by blocking cystine uptake. GSH plays an important role in antioxidant defense, and redox regulation. GSH deficiency has been associated with various neurodegenerative diseases. Intracellular GSH levels were determined by the X c- and ASC systems. The X c-system transports cystine intracellularly in exchange for glutamate, whereas the ASC system is a Na+-dependent neutral amino acid transporter that mediates the cellular transport of cysteine. Following uptake, cystine is reduced to cysteine for intracellular glutathione synthesis. However, elevated levels of glutamate inhibit cystine uptake, and subsequent restriction of cysteine availability for the cell, leading to GSH depletion.

Figure 4:
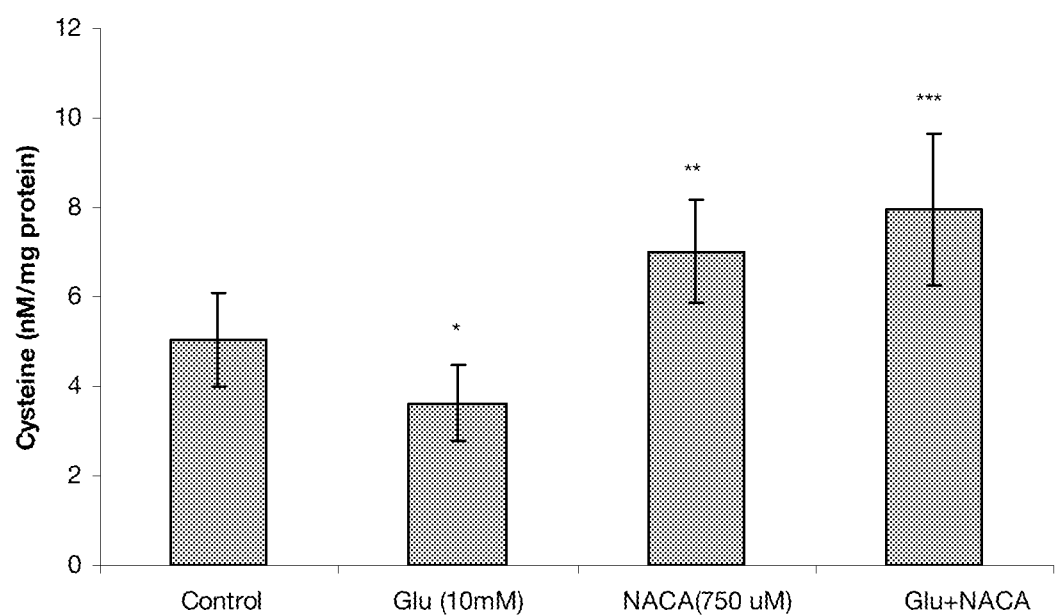
FIG. 4 shows the effect of NAC amide on glutamate-induced cytotoxicity. Cells were exposed to 10 mM Glu, with or without NAC amide, for 24 hours; the effects were compared to the control. Cell viability was quantified by the MTS assay. Values represent means±SD. Statistically different values of *P<0.0005 and P<0.05 were determined, compared to control. *P<0.05 compared to glutamate-treated group.
Figure 5:
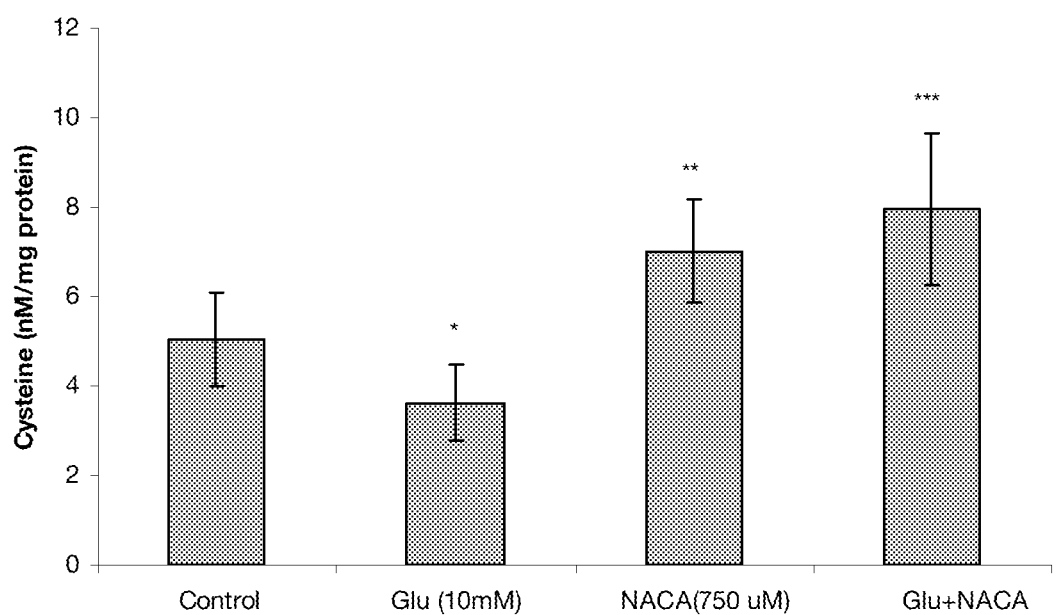
FIG. 5 shows the effects of NAC amide [NAC amide] on cysteine levels in PC12 cells. Cells were plated and grown for 24 hours, and then they were exposed to glutamate (10 mM) in the presence or absence of NAC amide (750 µM). Twenty-four hours later, the cells were harvested and cysteine levels were measured. Values represent means±SD. Statistically different values of *P<0.005 and P<0.05 were determined, compared to control. *P<0.05 compared to glutamate-treated group.

In this Example, incubation of PC12 cells with glutamate resulted in reduction of GSH (Table 1) and cysteine levels (FIG. 4), when compared to the control group. Reduced levels of cysteine indicate that the presence of excess glutamate inhibited cystine uptake, which led to decreased GSH levels. NAC amide treatment was able to increase GSH (Table 1) and cysteine levels (FIG. 5), compared to the control group, and effectively reversed the inhibitory action of glutamate. Increases in GSH and cysteine levels were also observed 30 minutes after NAC amide was administered to mice. The possible mechanism for NAC amide to facilitate the supply of cysteine may be by readily reaching the cell's interior, and becoming deacetylated to form cysteine. To understand whether NAC amide could restore the GSH levels in GSH synthesis-arrested cells, PC12 cells were incubated with glutamate (10 mM) plus BSO (0.2 mM) in the presence of NAC amide (750 µM). Results showed that NAC amide elevated intracellular GSH levels in the presence of BSO, suggesting that the effect is γ-GCS-independent. Therefore, NAC amide itself may act as a sulfhydryl group donor for GSH synthesis.

In summary, Example 1 shows that NAC amide protects PC12 cells against glutamate-induced cytotoxicity by preventing glutamate-induced loss of cellular GSH and inhibiting lipid peroxides. These studies also show that the restoration of GSH synthesis by NAC amide in GSH synthesis-arrested cells is γ-GCS-independent. Without wishing to be bound by theory, the possible mechanisms by which NAC amide can enhance GSH are 1) supplying the rate-limiting substrate cysteine to the cells and 2) reducing GSSG to GSH by a nonenzymatic thiol-disulfide exchange. Considering the protective effects of NAC amide against glutamate-induced cytotoxicity, in which oxidative stress seems to be involved, NAC amide can play a role in the treatment of neurodegenerative disorders such as cerebral ischemia and Parkinson's disease in which GSH levels are depleted in certain regions of the brain.

Example 2

This Example examines the radioprotective effects of NAC amide. To evaluate the protective effects of NAC amide against radiation exposure, the radioprotective role of NAC amide was compared with that of NAC with respect to increasing the levels of GSH and returning oxidative stress parameters to their control values.

Animal studies: The irradiation of rats was performed at the Radiation Oncology Department of the Phelps County Regional Medical Center in Rolla, Mo., using a 16 MeV beam generated by a Varian linear accelerator, model Clinac 1800, and in accordance with the standards of humane laboratory animal protocols. A 20.times.20 or 25.times.25 cm field was used and output factors were checked once a week. Twelve animals were divided into 4 groups each containing 3 animals (Control, XRT, NAC amide+XRT and NAC+XRT). The radiation (XRT) control received whole body irradiation by 6 Gy of 16 MeV electrons. The NAC amide+XRT group received 500 mg/kg/day NAC amide immediately before irradiation and for three days after until sacrifice. The rats were anesthetized and heparinized blood was collected via cardiopuncture. Following sacrifice, liver, lung, brain and spleen were removed and stored at −70° C. until homogenization.

All experiments were performed using adult Albino SASCO Sprague Dawley female rats weighing about 250 g, which were purchased from Charles River Laboratories Inc. (Portage, Mich.). Twelve rats were shipped in paper crates (4 in each crate). Rats were delivered with a certificate including serological, bacteriological, pathological parasitological information. They were divided into 4 cages (3 rats in each cage) and kept in a temperature controlled (20° C.) room equipped to maintain a 12 h light-dark cycle. Standard rat chow (Purina rat chow) and tap water were supplied in individual glass bottle and given ad libitum. Water was changed daily. Weights of the animal were taken before giving the NAC amide treatment solution and amount of food eaten and water consumed was not measured because NAC amide was given orally but not in the drinking water or food.

NAC amide was provided by Novetide Ltd (Haifa Bay, Israel) including certificate of analysis and MSDS (lot #40233-64). NAC amide feeding solution was prepared freshly each day right before the administration by weighing 1.25 g NAC amide solid sample (Type HR-120 electronic balance, A&D Company limited, Japan. S/N: 12202464) and adding into 10 ml PBS solution and put on ice. One ml of this solution was administrated (gavaged) per rat orally by using animal feeding biomedical needles and 3 ml BD Luer-Lok Tip syringes. Rats received one-dose total-body 6 Gy/16 MeV x-ray radiation and 3 rats in each group were held in a covered bucket and received radiation at the same time. Each day at the same time, 500 mg/Kg body weight of NAC amide was administrated to the animals.

All the results are normalized into values per unit (mg) of protein content for all the tissue samples.

Typical standard curves:
GSH: y=8.57544x−425.092, R2=0.9997
CYS: y=7.53294x+184.35, R2=0.9995

For GSH and CYS levels, 250 µL tissue homogenate was used to react with 750 µL NPM solution, therefore, the total volume was 1000 µL.

As an example:

The peak area for GSH in the sample is 90860.25. The GSH concentration (nM) is calculated from the standard curve. After determining the protein content (mg/ml) of the sample, for example: 16.5 mg/ml, the calculation is as follows:

[(90860.25+425.092)/8.57544 nmol/L]*[1 L/1000 mL]*[1000 μL/250 μL]/(16.5 mg/ml)=2.58 nmol GSH/mg protein MDA: y=26.6869x+370.488, R2=0.9990

For MDA levels, 350 μL tissue homogenate was used to react with 100 μL of 500 ppm BHT solution and 550 μL solution of 10% TCA solution, therefore, the total volume here was 1000 μL. After boiling the whole solution, 500 μL was taken out and react with 500 μL TBA and the total volume here was 1000 μL also.

As an example:

The peak area for MDA in the sample as 65289.23, The MDA concentration (nM) is calculated from the standard curve. After determining the protein content (mg/ml) of the sample, for example: 16.5 mg/ml, the resulting calculation is as follows: [(65289.23-370.488)/26.6869 nmol/L]*[1 L/1000 mL]*[1000 μL/350 μL]*[1000 μL/500 μL]/(16.5 mg/ml)*100=84.3 nmol MDA/100 mg protein Catalase:

Calculation for specific activity:

In assay solution, k (enzyme activity)=1/60*ln(A0/A60)* (Total Volume of reaction/volume of sample) A0—Absorbance at 0 second A60—Absorbance at 60 second In sample, K (specific activity), k/protein concentration.

Oxidative Stress Parameters in Animals: After the blood samples were drawn, the animals were perfused by a cold antioxidant buffer first and then liver, brain and kidney samples were collected aseptically, rinsed in ice-cold saline and placed in petri dishes maintained on ice. The tissue samples kept at −70° C. for the GSH, GSSG, and MDA determinations were made.

Glutathione (GSH) and Glutathione Disulfide (GSSG) Determination: Cells or tissue samples were homogenized on ice and derivatized with N-(1-pyrenyl)-maleimide (NPM). The derivatized samples were injected onto a 3 μm C18 column (Column Engineering) in a reverse phase HPLC system with a mobile phase of 35% water, 65% acetonitrile containing 1 mL/L of acetic acid and o-phosphoric acid (R. Winters, et al., Anal. Biochem., 227:14-21 (1995) and H. H. Draper et al., Free Rad. Biol. Med., 15:353-363 (1993)). Malondialdehyde (MDA) determinations were made as described in J. Gutteridge, Anal. Biochem., 69: 518-526 (1975).

Enzyme Activity Assays: Catalase (CAT) activity was determined spectrophotometrically and was expressed in kunits/mg protein and kunits/$10^6$ cells as described by M. Bradford, Anal. Biochem., 72:248-256 (1976).

Statistical Analysis: Tabulated values represent means.+−.standard deviations. InStat® by GraphPad Software, San Diego, Calif. will use One-way Analysis of Variance (ANOVA) and the Student-Newman-Keuls Multiple Comparisons Test to analyze data from experimental and control groups. The p values<0.05 is considered significant.

The results of the studies described in this Example are provided in the tables below. In these tables, AD4 is synonymous with NAC amide.

TABLE 3

GSH and CYS levels in BRAIN after 6Gy total-body x-ray radiation with AD4 or NAC administration (500 mg/kg orally)

| (n = 3) | GSH (nmol/mg) | | | CYS (nmol/mg) | | |
|---|---|---|---|---|---|---|
| | level | Mean | SD | level | Mean | SD |
| CTR-1 | 8.19 | 7.5 | 0.7 | 3.61 | 4.1 | 0.5 |
| CTR-2 | 6.75 | | | 3.88 | | |
| CTR-3 | 7.59 | | | 4.79 | | |
| XRT-1 | 6.42 | 6.6 | 0.3 | 3.48 | 3.8 | 0.5 |
| XRT-2 | 6.35 | | | 3.76 | | |
| XRT-3 | 6.89 | | | 4.36 | | |
| XRT + AD4-1 | 7.93 | 7.6** | 0.5 | 4.47 | 4.4 | 0.1 |
| XRT + AD4-2 | 7.84 | | | 4.32 | | |
| XRT + AD4-3 | 6.98 | | | 4.26 | | |
| XRT + NAC-1 | 7.32 | 7.0 | 0.3 | 4.16 | 4.1 | 0.4 |
| XRT + NAC-2 | 6.74 | | | 3.76 | | |
| XRT + NAC-3 | 7.15 | | | 4.47 | | |

TABLE 4

GSH and CYS levels in LIVER after 6Gy total-body x-ray radiation with AD4 or NAC administration (500 mg/kg orally)

| (n = 3) | GSH (nmol/mg) | | | CYS (nmol/mg) | | |
|---|---|---|---|---|---|---|
| | level | Mean | SD | level | Mean | SD |
| CTR-1 | 15.70 | 16.9 | 1.1 | 1.64 | 1.5 | 0.3 |
| CTR-2 | 17.99 | | | 1.78 | | |
| CTR-3 | 16.97 | | | 1.17 | | |
| XRT-1 | 14.54 | 14.4* | 0.2 | 1.34 | 1.4 | 0.1 |
| XRT-2 | 14.26 | | | 1.39 | | |
| XRT-3 | 14.30 | | | 1.55 | | |
| XRT + AD4-1 | 17.45 | 17.2** | 0.4 | 1.51 | 1.5 | 0.01 |
| XRT + AD4-2 | 16.73 | | | 1.53 | | |
| XRT + AD4-3 | 17.50 | | | 1.53 | | |
| XRT + NAC-1 | 15.23 | 16.3 | 1.0 | 1.25 | 1.5 | 0.2 |
| XRT + NAC-2 | 16.80 | | | 1.61 | | |
| XRT + NAC-3 | 16.93 | | | 1.51 | | |

TABLE 5

GSH and CYS levels in KIDNEY after 6Gy total-body x-ray radiation with AD4 or NAC administration (500 mg/kg orally)

| (n = 3) | GSH (nmol/mg) | | | CYS (nmol/mg) | | |
|---|---|---|---|---|---|---|
| | level | Mean | SD | level | Mean | SD |
| CTR-1 | 4.62 | 5.5 | 0.8 | 10.29 | 11.1 | 0.7 |
| CTR-2 | 6.25 | | | 11.56 | | |
| CTR-3 | 5.63 | | | 11.37 | | |
| XRT-1 | 4.91 | 4.8 | 0.3 | 8.13 | 8.7* | 0.5 |
| XRT-2 | 4.98 | | | 9.07 | | |
| XRT-3 | 4.38 | | | 8.94 | | |
| XRT + AD4-1 | 4.39 | 5.2 | 0.9 | 16.91 | 12.9** | 3.4 |
| XRT + AD4-2 | 6.22 | | | 11.09 | | |
| XRT + AD4-3 | 5.02 | | | 10.81 | | |
| XRT + NAC-1 | 5.95 | 6.2** | 0.3 | 12.23 | 11.8* | 0.7 |
| XRT + NAC-2 | 6.44 | | | 12.16 | | |
| XRT + NAC-3 | 6.33 | | | 11.03 | | |

TABLE 6

GSH and CYS levels in LUNG after 6Gy total-body x-ray radiation with AD4 or NAC administration (500 mg/kg orally)

| (n = 3) | GSH (nmol/mg) | | | CYS (nmol/mg) | | |
|---|---|---|---|---|---|---|
| | level | Mean | SD | level | Mean | SD |
| CTR-1 | 7.04 | 6.2 | 0.7 | 1.91 | 1.7 | 0.3 |
| CTR-2 | 5.87 | | | 1.85 | | |
| CTR-3 | 5.78 | | | 1.44 | | |
| XRT-1 | 5.24 | 5.1 | 0.8 | 1.26 | 1.6 | 0.3 |
| XRT-2 | 4.25 | | | 1.66 | | |
| XRT-3 | 5.93 | | | 1.83 | | |
| XRT + AD4-1 | 5.12 | 5.6 | 0.6 | 1.43 | 1.3 | 0.4 |
| XRT + AD4-2 | 5.27 | | | 1.61 | | |
| XRT + AD4-3 | 6.28 | | | 0.91 | | |
| XRT + NAC-1 | 5.19 | 5.8 | 1.3 | 1.16 | 1.9 | 0.7 |
| XRT + NAC-2 | 7.24 | | | 2.04 | | |
| XRT + NAC-3 | 4.95 | | | 2.43 | | |

TABLE 7

GSH and CYS levels in PLASMA after 6Gy total-body x-ray radiation with AD4 or NAC administration (500 mg/kg orally)

| (n = 3) | GSH (nmol/mg) | | | CYS (nmol/mg) | | |
|---|---|---|---|---|---|---|
| | level | Mean | SD | level | Mean | SD |
| CTR-1 | 7.65 | 7.4 | 0.4 | 16.03 | 15.5 | 0.4 |
| CTR-2 | 7.49 | | | 15.20 | | |
| CTR-3 | 6.92 | | | 15.39 | | |
| XRT-1 | 5.27 | 5.3* | 0.1 | 12.68 | 13.6* | 0.9 |
| XRT-2 | 5.39 | | | 13.63 | | |
| XRT-3 | 5.31 | | | 14.45 | | |
| XRT + AD4-1 | 7.10 | 7.6** | 0.4 | 16.00 | 15.6** | 0.1 |
| XRT + AD4-2 | 7.44 | | | 15.45 | | |
| XRT + AD4-3 | 7.94 | | | 15.40 | | |
| XRT + NAC-1 | 7.08 | 6.5**/*** | 0.5 | 14.64 | 14.2*** | 0.5 |
| XRT + NAC-2 | 6.18 | | | 13.75 | | |
| XRT + NAC-3 | 6.27 | | | 14.36 | | |

*P < 0.05 compared to the CTR group;
**P < 0.005 compared to the XRT only group
***P < 0.05 compared to the XRT + AD4-treated goup

TABLE 8

MDA levels in BRAIN after 6Gy total-body x-ray radiation with AD4 or NAC administration (500 mg/kg orally)

| (n = 3) | MDA (nmol/100 mg) | | |
|---|---|---|---|
| | level | Mean | SD |
| CTR-1 | 4.93 | 4.09 | 0.80 |
| CTR-2 | 3.33 | | |
| CTR-3 | 4.02 | | |
| XRT-1 | 5.64 | 5.99* | 0.68 |
| XRT-2 | 6.76 | | |
| XRT-3 | 5.55 | | |
| XRT + AD4-1 | 5.79 | 5.48 | 0.33 |
| XRT + AD4-2 | 5.53 | | |
| XRT + AD4-3 | 5.13 | | |
| XRT + NAC-1 | 6.42 | 6.15 | 0.72 |
| XRT + NAC-2 | 6.69 | | |
| XRT + NAC-3 | 5.33 | | |

TABLE 9

MDA levels in LIVER after 6Gy total-body x-ray radiation with AD4 or NAC administration (500 mg/kg orally)

| (n = 3) | MDA (nmol/100 mg) | | |
|---|---|---|---|
| | level | Mean | SD |
| CTR-1 | 4.36 | 4.62 | 0.39 |
| CTR-2 | 4.44 | | |
| CTR-3 | 5.07 | | |
| XRT-1 | 8.9 | 8.36* | 0.53 |
| XRT-2 | 8.35 | | |
| XRT-3 | 7.83 | | |
| XRT + AD4-1 | 4.14 | 4.38** | 0.26 |
| XRT + AD4-2 | 4.65 | | |
| XRT + AD4-3 | 4.36 | | |
| XRT + NAC-1 | 5.1 | 5.07**/*** | 0.04 |
| XRT + NAC-2 | 5.1 | | |
| XRT + NAC-3 | 5.02 | | |

TABLE 10

MDA levels in KIDNEY after 6Gy total-body x-ray radiation with AD4 or NAC administration (500 mg/kg orally)

| (n = 3) | MDA (nmol/100 mg) | | |
|---|---|---|---|
| | level | Mean | SD |
| CTR-1 | 1.61 | 1.69 | 0.09 |
| CTR-2 | 1.8 | | |
| CTR-3 | 1.68 | | |
| XRT-1 | 2.48 | 2.28* | 0.17 |
| XRT-2 | 2.17 | | |
| XRT-3 | 2.18 | | |
| XRT + AD4-1 | 1.5 | 1.64** | 0.28 |
| XRT + AD4-2 | 1.96 | | |
| XRT + AD4-3 | 1.45 | | |
| XRT + NAC-1 | 1.76 | 1.65** | 0.21 |
| XRT + NAC-2 | 1.78 | | |
| XRT + NAC-3 | 1.41 | | |

TABLE 11

MDA levels in LUNG after 6Gy total-body x-ray radiation with AD4 or NAC Administration (500 mg/kg orally)

| (n = 3) | MDA (nmol/100 mg) | | |
|---|---|---|---|
| | level | Mean | SD |
| CTR-1 | 1.47 | 1.54 | 0.07 |
| CTR-2 | 1.53 | | |
| CTR-3 | 1.61 | | |
| XRT-1 | 2.3 | 2.80* | 0.45 |
| XRT-2 | 2.94 | | |
| XRT-3 | 3.17 | | |
| XRT + AD4-1 | 1.72 | 1.53** | 0.22 |
| XRT + AD4-2 | 1.58 | | |
| XRT + AD4-3 | 1.28 | | |
| XRT + NAC-1 | 2.58 | 2.52** | 0.15 |
| XRT + NAC-2 | 2.34 | | |
| XRT + NAC-3 | 2.63 | | |

*P < 0.05 compared to the CTR group
**P < 0.005 compared to the XRT only group
***P < 0.05 compared to the XRT + AD4-treated group

TABLE 12

Catalase activities in KIDNEY after 6Gy total-body x-ray radiation with AD4 or NAC administration (500 mg/kg orally):

| (n = 3) | Catalase (mU/mg) | | |
|---|---|---|---|
| | level | Mean | SD |
| CTR-1 | 2.75 | 2.34 | 0.78 |
| CTR-2 | 2.84 | | |
| CTR-3 | 1.44 | | |
| XRT-1 | 8.73 | 8.69* | 1.05 |
| XRT-2 | 7.59 | | |
| XRT-3 | 9.66 | | |
| XRT + AD4-1 | 3.89 | 3.97** | 0.56 |
| XRT + AD4-2 | 3.46 | | |
| XRT + AD4-3 | 4.56 | | |
| XRT + NAC-1 | 5.85 | 4.41 | 1.48 |
| XRT + NAC-2 | 3.02 | | |
| XRT + NAC-3 | 4.36 | | |

TABLE 13

Catalase activities in LUNG after 6Gy total-body x-ray radiation with AD4 or NAC administration (500 mg/kg orally):

| (n = 3) | Catalase (mU/mg) | | |
|---|---|---|---|
| | level | Mean | SD |
| CTR-1 | 1.50 | 1.24 | 0.33 |
| CTR-2 | 0.87 | | |
| CTR-3 | 1.37 | | |
| XRT-1 | 3.53 | 2.03 | 1.43 |
| XRT-2 | 0.72 | | |
| XRT-3 | 1.83 | | |
| XRT + AD4-1 | 1.02 | 0.68** | 0.29 |
| XRT + ND4-2 | 0.50 | | |
| XRT + AD4-3 | 0.53 | | |
| XRT + NAC-1 | 2.12 | 1.13 | 0.89 |
| XRT + NAC-2 | 0.79 | | |
| XRT + NAC-3 | 0.48 | | |

TABLE 14

Catalase activities in LIVER after 6Gy total-body x-ray radiation with AD4 or NAC administration (500 mg/kg orally).

| (n = 3) | Catalase (mU/mg) | | |
|---|---|---|---|
| | level | Mean | SD |
| CTR-1 | 49.48 | 43.03 | 6.13 |
| CTR-2 | 42.39 | | |
| CTR-3 | 37.23 | | |
| XRT-1 | 89.10 | 77.44* | 10.46 |
| XRT-2 | 69.23 | | |
| XRT-3 | 74.00 | | |
| XRT + AD4-1 | 69.63 | 59.28** | 9.80 |
| XRT + AD4-2 | 57.88 | | |
| XRT + AD4-3 | 50.33 | | |
| XRT + NAC-1 | 75.22 | 71.11*** | 3.56 |
| XRT + NAC-2 | 69.09 | | |
| XRT + NAC-3 | 69.00 | | |

*P < 0.05 compared to the CTR group;
**P < 0.05 compared to the XRT only group
***P < 0.05 compared to the XRT + AD4-treated group The data presented support the finding that NAC amide functions as a strong thiol antioxidant in radiation-induced oxidative stress. NAC does not increase GSH levels in tissues, presumably because it does not cross the cell membranes. Although plasma Cys level increased significantly, this was not reflected in the liver. NAC generally provides GSH only during increased demand on the GSH pool.

Upon irradiation, reactive oxygen species are formed through oxygen's acceptance of electrons, which are involved in free radical chain reactions and are highly damaging to the cell through disruption of the cellular pro-oxidant/antioxidant balance. Normal tissue damage limits the radiation dose and treatment volume in radiotherapy. Radioprotection of normal tissue by thiols offers one way in which radiation dosage can be increased. The focus in this Example was to examine the radioprotective effects of NAC amide using a whole body radiation dose of 6 Gy, sufficient to insure that all animals should progress with lethal gastrointestinal and hematopoietic syndromes. The time point chosen for analyses, 4 days, approximates the time that the animals would begin to succumb to the gastrointestinal syndrome, but would be expected to show only early changes in the hematopoietic syndrome.

GSH, a tripeptide consisting of γ-glutamyl-cysteinyl-glycine, is the principle water-soluble intracellular free thiol and acts as a radioprotector. Several distinct mechanisms of radioprotection by GSH can be identified and include radical scavenging, hydrogen donation to damaged molecules, reduction of peroxides, and protection of protein thiol oxidative status. GSH has been shown to decrease in tissues following irradiation. Since GSH is an endogenous radioprotector, modification of GSH concentration may be useful as radiation protection. Cysteine provides the rate-limiting step in GSH synthesis since its apparent Km value for γ-glutamyl-cysteine synthetase is close to the intracellular concentration of the amino acid. However, administration of cysteine is not the ideal way to increase intracellular GSH, since it auto-oxidizes rapidly and can lead to the production of hydroxyl and thiyl radicals.

NAC, a cysteine analogue that is a mucolytic agent and a treatment for paracetamol intoxication, promotes hepatic GSH synthesis. It penetrates the cell membrane and is rapidly deacetylated to L-cysteine, while also stimulating GSSG reductase. NAC can rapidly increase the hepatic GSH levels and maintain these levels for at least 6 hours (B. Wong et al., J. Pharm. Sci., 75:878-880 (1986)). NAC has also been shown to protect Chinese hamster ovary cells from lead and .delta.-aminolevulinic acid-induced toxicity through restoration of the oxidative status of the cells by GSH replenishment. It has been demonstrated that NAC protects liver and brain of C57BL/6 mice from GSH depletion as a result of lead poisoning. Radioprotective effects of select thiols such as indomethacin, WR-2721, cysteamine, and diethyldithiocarbamate have been reported, though at higher concentrations these induce cellular toxicity. The radioprotective effect of NAC has been demonstrated in human granulocyte/macrophage-colony forming cells. However, it has also been shown that the more radioresistant SW-1573 human squamous lung carcinoma cell line was not protected from X-ray induced cell death by NAC. NAC amide is more lipophilic and able to more easily cross cell membranes than NAC. In this Example, the radioprotective function of NAC amide was compared with that of NAC in terms of increasing GSH levels and returning oxidative stress parameters to their control values.

The exposure of membrane lipids to reactive oxygen species such as the hydroxyl radical can initiate a chain reaction in polyunsaturated fatty acid moieties, which results in peroxidation and causes degradation of membrane function. MDA is a degradation product of the highly unstable lipid peroxides. As observed in this Example, irradiation of Sprague Dawley rats resulted in increased MDA levels in liver and lung. Upon treatment with NAC amide concurrent with irradiation, lung MDA levels were significantly lowered, while treatment with NAC did not change the MDA levels significantly.

It is generally accepted in the field of radiobiology that the mechanism of individual cell killing by radiation exposure is due to direct and indirect ionizing effects specifically upon DNA in the cell nucleus, although it becomes apparent that in a complex organism there are ROS effects of some potential importance on membrane lipids and proteins as well as on nucleic acids. Furthermore, acute whole body irradiation of the intact animal under conditions modeling the so called "gastrointestinal syndrome" causes changes in several tissues apart from gastrointestinal tract, and some of these effects can be ameliorated by the use of NAC amide. A given syndrome such as the "gastrointestinal syndrome" can actually involve a complex of changes in multiple tissues and organs. Radiation pneumonitis can be a serious hazard in the therapeutic irradiation of patients with lung cancer. NAC amide may be considered for use as a thiol radioprotectant to protect against such a complication. Thus, in accordance with the invention, NAC amide significantly increases thiol levels in plasma and liver and performs better than NAC as a radioprotecting agent.

Example 3

This Example describes a treatment regimen suitable for humans. NAC amide is administered between 1 and three grams per day, in two divided doses, between meals (on an empty stomach). Encapsulated NAC amide (a formulation of NAC amide comprising 500 mg NAC amide and optionally, 250 mg USP grade crystalline ascorbic acid, and not more than 0.9 mg magnesium stearate, NF grade in an OO-type gelatin capsule) is suitable for administration. The administration of exogenous NAC amide is expected to provide a dose response effect in patients, despite the production of large quantities of glutathione in the human body.

Example 4

This Example describes a combination pharmaceutical composition to ameliorate the detrimental effects of acetaminophen, a drug that consumes glutathione in the liver during metabolism and, in excess doses, causes liver damage due to oxidative damage. The composition includes 500 mg NAC amide, 250 mg crystalline ascorbic acid and 350 mg acetaminophen.

Example 5

This Example describes a combination pharmaceutical composition to ameliorate the detrimental effects of chlorpromazine, a phenothiazine drug that causes side effects, including tardive dyskinesia, which may be associated with excess free radical reactions. The composition includes 500 mg NAC amide, 250 mg crystalline ascorbic acid and 200 mg chlorpromazine.

Example 6

This Example describes a combination pharmaceutical composition to ameliorate the detrimental effects of aminoglycoside drugs (antibiotics), nonlimiting examples of which include neomycin, kanamycin, amikacin, streptomycin, gentamycin, sisomicin, netilmicin and tobramycin, a drug class which may be associated with various toxicities. This damage may be related to oxidative damage or consumption of glutathione during metabolism. The composition according to the present invention is an intravenous formulation, including the aminoglycoside in an effective amount, and NAC amide in an amount of about 10-20 mg/kg. Ascorbic acid in an amount of 5-10 mg/kg may be added as a stabilizer.

Example 7

This Example describes a urethral insert comprising NAC amide. A composition containing 200 mg NAC amide, 50 mg ascorbic acid per unit dosage is mixed with carageenan and/or agarose and water in a quick-gelling composition, and permitted to gel in a cylindrical form having a diameter of about 3 mm and a length of about 30 mm. The composition is subjected to nitric oxide to cause between 0.1-10% of the NAC amide to be converted to nitroso-NAC amide. The gelled agarose is then freeze dried under conditions that allow shrinkage. The freeze-dried gel is than packaged in a gas barrier package, such as a foil pouch or foil "bubble-pack". The freeze-dried gel may then be used as a source of nitroso-NAC amide for administration transmucosally. The cylindrical freeze-dried gel may be inserted into the male urethra for treatment of impotence, or administered sublingually for systemic vasodilation.

Example 8

This Example describes an oral formulation for prophylaxis of vascular disease, e.g., in men over 40. The composition includes 500 mg NAC amide, 250 mg USP grade crystalline ascorbic acid and 50 mg USP acetyl salicylic acid (aspirin) in an OO-type gelatin capsule. Typical administration is twice per day. The acetyl salicylic acid may be provided in enteric release pellets within the capsule to retard release.

Example 9

This Example describes an oral formulation for prophylaxis of vascular disease. The composition contains 500 mg NAC amide, 200 mg USP grade crystalline ascorbic acid, and 200 mg arginine in an OO-type gelatin capsule. Arginine is the normal starting substrate for the production of nitric oxide. Because arginine is normally in limited supply, a relative deficiency of arginine may result in impaired vascular endothelial function.

Example 10

This Example describes an oral formulation for prophylaxis of vascular disease. The composition includes 500 mg NAC amide, 200 mg USP grade crystalline ascorbic acid, and 200 mg vitamin E succinate in an OO-type gelatin capsule. Vitamin E consumption reduces the risk of heart attack and other vascular disease. Vitamin E succinate (alpha-tocopherol succinate) is a dry powder.

Example 11

This Example describes an oral formulation for prophylaxis of vascular disease. Nonspecific esterases having broad substrate specificity are present in the plasma. According to the present invention, esters are formed between agents that are useful combination therapies in order to provide for efficient administration, high bioavailability, and pharmaceutical stability. Preferred esters include alpha tocopherol-ascorbate, alpha tocopherol-salicylate, and ascorbyl-salicylate. The tocopherol ester maintains the molecule in a reduced state, allowing full antioxidant potential after ester cleavage. These esters may be administered alone or in combination with other agents, for example NAC amide. Typically, the esters are administered to deliver an effective dose of salicylate equivalent of 100 mg per day for prophylaxis, or 750-1000 mg per dose for treatment of inflammatory diseases. Tocopherol is administered in an amount of 100-500 IU equivalent. Ascorbate is administered in an amount of up to 1000 mg equivalent. In order to enhance availability, a non-specific esterase may be provided in the formulation to cleave the ester after dissolution of the capsule. Therefore, a non-specific esterase, such as a bacterial or *saccharomyces* (yeast) enzyme, or an enriched enzyme preparation, may be included in the formulation as a powder or as pellets in the capsule.

Example 12

This Example describes an oral formulation for prophylaxis of vascular disease. The composition includes 500 mg reduced NAC amide, 200 mg USP grade crystalline ascorbic acid, and 100 mg nordihydroguairetic acid, in an OO-type gelatin capsule. Typical administration is twice per day. Nordihydroguairetic acid is a known lipoxygenase inhibitor. Thus, this composition may be used to treat inflammatory processes or as prophylaxis against vascular disease.

Example 13

This Example describes a study observing the survival of rats receiving whole body, single-dose irradiation by X-rays (XRT) in the presence or absence of NAC or NAC amide (TOVA). In this experiment, thirty-nine female Sprague-Dawley rats ranging from about 150-200 g were subjected to total body, single-dose X-ray irradiation (9 Gy, 16 Mev). The same groups were designated to receive either NAC or TOVA. For the pre-treatment groups (n=6 in each group), the first treatment of NAC or TOVA was administered 30 minutes to 1 hour before irradiation. For the post-pretreatment groups (n=6 in each group), the first treatment of NAC or TOVA was administered 30 minutes to 1 hour after the irradiation. For groups receiving NAC or TOVA, the same amount (500 mg/kg NAC or TOVA daily) was administered for 4 or 5 consecutive days.

Group 1 was a control group (n=3), where rats received the same amount of saline solution daily for 5 consecutive days without XRT. Group 2 rats received NAC only (n=3) at an amount of 500 mg/kg body weight NAC daily for 5 consecutive days without XRT. Group 3 rats received TOVA only (n=3) at an amount of 500 mg/kg body weight TOVA daily for 5 consecutive days without XRT. Group 4 rats received radiation (XRT) only (n=6) and received the same amount of saline solution daily for 5 consecutive days after single dose total-body XRT irradiation.

Group 5 rats received one treatment of NAC at 500 mg/kg body weight before XRT (XRT+NAC pre-treated), which was then followed by 500 mg/kg body weight NAC daily for 4 consecutive days after XRT. Group 6 rats received XRT, followed by daily doses of NAC at 500 mg/kg body weight for 5 consecutive days after XRT (XRT+NAC post-treated). Group 7 rats received one treatment of NAC at 500 mg/kg body weight before XRT (XRT+TOVA pre-treated), which was then followed by 500 mg/kg body weight TOVA daily for 4 consecutive days after XRT. Group 8 rats received XRT, followed by daily doses of TOVA at 500 mg/kg body weight for 5 consecutive days after XRT (XRT+TOVA post-treated). All rats were then given a normal diet post-treatment.

The rats were observed twice a day, and the survival status of rats in each group will be recorded. The mean survival days were calculated for each group and compared to the survival differences of the three groups of rats at the end of the experiment. The radioprotective effects of NAC and TOVA treatment on the survival of those irradiated rats were then evaluated, as shown in the following tables.

TABLE 15

| Groups | # of animals | # of animals dead | # of animals survived | survival rate | percentage survival rate |
|---|---|---|---|---|---|
| XRT only | (n = 6)-1st time | 2 | 4 | (4 + 2)/(6 + 6) | 50% |
|  | (n = 6)-2nd time | 4 | 2 |  |  |
| XRT + NAC (pre-treated) | (n = 6)-1st time | 1 | 5 | (5 + 5)/(6 + 6) | 83.3% |
|  | (n = 6)-2nd time | 1 | 5 |  |  |
| XRT + TOVA (pre-treated) | (n = 6)-1st time | 0 | 6 | (6 + 6)/(6 + 6) | 100% |
|  | (n = 6)-2nd time | 0 | 6 |  |  |
| Control (no XRT and any treatment) | (n = 3)-1st time | 0 | 3 | (3 + 3)/(3 + 3) | 100% |
|  | (n = 3)-2nd time | 0 | 3 |  |  |
| NAC only | (n = 2)-2nd time | 0 | 2 | (2)/(2) | 100% |
| TOVA only | (n = 3)-2nd time | 0 | 3 | (3)/(3) | 100% |
| XRT + NAC (post-treated) | (n = 6)-2nd time | 4 | 2 | (2)/(6) | 33.3% |
| XRT + TOVA (post-treated) | (n = 6)-2nd time | 2 | 4 | (4)/(6) | 66.7% |

Table 16 shows the survival rate percentage of rats receiving NAC or TOVA pre- or post-XRT treatment.

TABLE 16

| Groups | percentage survival rate |
|---|---|
| XRT only | 50% |
| XRT + NAC(pre-treated) | 83.3% |
| XRT + TOVA(pre-treated) | 100% |
| Control (no XRT and any treatment) | 100% |
| NAC only | 100% |
| TOVA only | 100% |
| XRT + NAC(post-treated) | 33.3% |
| XRT + TOVA(post-treated) | 66.7% |

Figure 6:
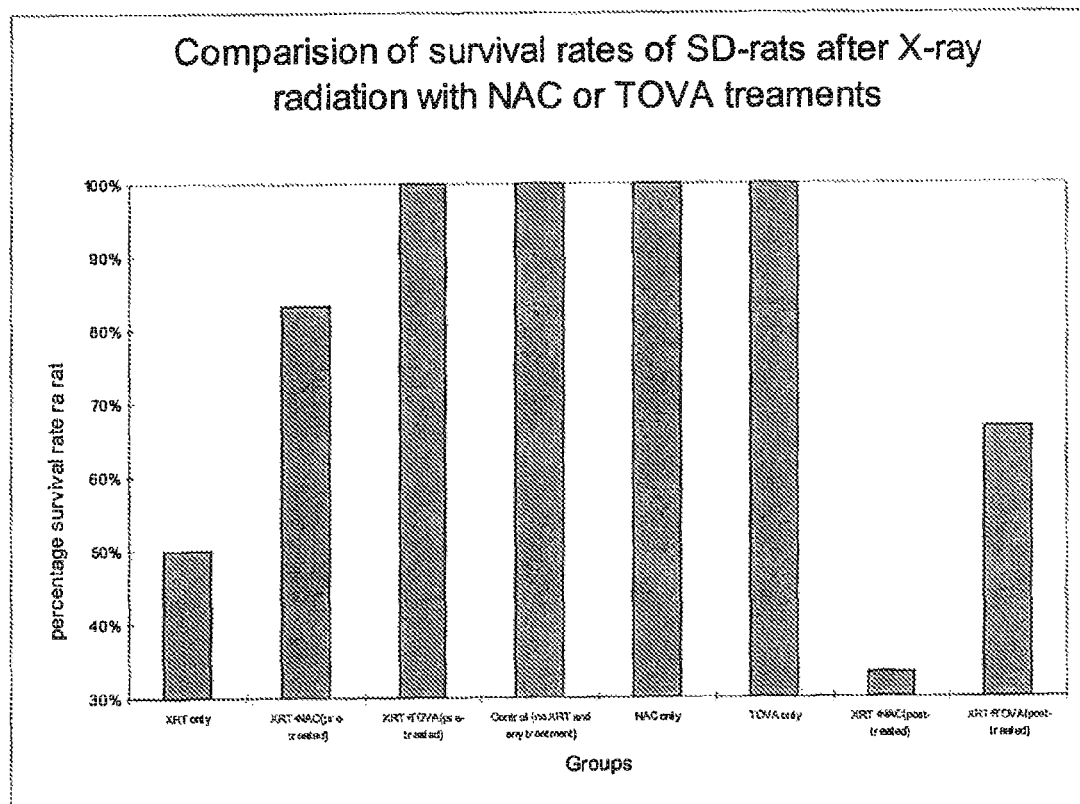
FIG. 6 is a graph depicting a comparison of survival rates of Sprague-Dawley rats after X-ray irradiation treatment in combination with pre-treatment or post-treatment with NAC or NAC amide (TOVA).

FIG. 6 is a graphical representation comparing the percentage survival rates as presented in Table 16. These results show that rats pre-treated with NAC or TOVA before XRT have a higher survival rate than those receiving XRT alone.

All patent applications, published applications, patents, texts, and literature references cited in this specification are hereby incorporated herein by reference in their entirety.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

The invention claimed is:

1. A method for blocking or reducing hepatic toxicity of acetaminophen in a human subject, comprising administering to the human subject an effective dose of N-acetylcysteine amide (NAC Amide), or a pharmaceutically acceptable salt or ester thereof, thereby blocking or reducing hepatic toxicity of acetaminophen in the human subject.

2. The method according to claim 1, wherein the NAC Amide is administered as a prophylactic.

3. The method according to claim 1, wherein the dose for administration is 50-10,000 mg per dose.

4. The method of claim 1, wherein the dose for administration is 25-500 mg per dose.

5. The method of claim 1, wherein NAC Amide is delivered orally via a capsule.

6. The method of claim 1, wherein NAC Amide is administered subcutaneously, intravenously, intramuscularly, and intrasternally and intraperitoneally.

7. The method of claim 1, wherein NAC Amide is administered orally, via inhalation, topically, or intranasally.

8. The method of claim 1, wherein NAC Amide is administered before, concurrently with, and/or after an administration of acetaminophen.

9. A method of treating a human subject for hepatic toxicity of acetaminophen, comprising administering to the human subject an effective dose of N-acetylcysteine amide (NAC Amide), or a pharmaceutically acceptable salt or ester thereof, thereby treating the human subject in need of treatment for hepatic toxicity of acetaminophen.

10. The method according to claim 9, wherein the NAC Amide is administered as a prophylactic.

11. The method according to claim 9, wherein the dose for administration is 50-10,000 mg per dose.

12. The method of claim 9, wherein the dose for administration is 25-500 mg per dose.

13. The method of claim 9, wherein NAC Amide is delivered orally via a capsule.

14. The method of claim 9, wherein NAC Amide is administered subcutaneously, intravenously, intramuscularly, and intrasternally and intraperitoneally.

15. The method of claim 9, wherein NAC Amide is administered orally, via inhalation, topically, or intranasally.

16. The method of claim 9, wherein NAC Amide is administered before after exposure to acetaminophen.

17. A combination pharmaceutical composition comprising N-acetylcysteine amide (NAC Amide), and acetaminophen.

18. The combination pharmaceutical composition of claim 17, further comprising ascorbic acid.

19. The combination pharmaceutical composition of claim 17, comprising about 500 mg NAC Amide.

20. The combination pharmaceutical composition of claim 18, comprising about 250 mg ascorbic acid.

21. The combination pharmaceutical composition of claim 17, comprising about 350 mg acetaminophen.

22. The combination pharmaceutical composition of claim 17, comprising about 50-10,000 mg NAC Amide.

23. The combination pharmaceutical composition of claim 17, comprising about 25-500 mg NAC Amide.

24. The combination pharmaceutical composition of claim 17, comprising about 500 mg NAC Amide, and about 350 mg acetaminophen.

25. The combination pharmaceutical composition of claim 18, comprising about 500 mg NAC Amide, about 250 mg ascorbic acid, and about 350 mg acetaminophen.

* * * * *